United States Patent [19]
Cech et al.

[11] Patent Number: 5,116,742
[45] Date of Patent: * May 26, 1992

[54] RNA RIBOZYME RESTRICTION ENDORIBONUCLEASES AND METHODS

[75] Inventors: Thomas R. Cech; Felicia L. Murphy, both of Boulder; Arthur J. Zaug, Louisville; Cheryl Grosshans, Denver, all of Colo.

[73] Assignee: University Patents, Inc., Westport, Conn.

[*] Notice: The portion of the term of this patent subsequent to Jan. 22, 2008 has been disclaimed.

[21] Appl. No.: 328,503

[22] Filed: Mar. 24, 1989

Related U.S. Application Data

[63] Continuation-in-part of Ser. No. 937,327, Dec. 3, 1986, Pat. No. 4,987,071.

[51] Int. Cl.⁵ ..................... C12P 19/34; C12N 15/00; C12N 9/22
[52] U.S. Cl. ................... 435/91; 435/172.3; 435/199; 435/320.1; 935/3; 935/16
[58] Field of Search ................ 435/89, 90, 91, 194, 435/172.3, 199, 320.1; 502/167; 536/27

[56] References Cited

PUBLICATIONS

Guerrier-Takada et al. (1984), Cell, vol. 38, pp. 219-224.
Kay et al. (1987), Nature, vol. 327, p. 343.
Guerrier-Takada and Altman, "Catalytic Activity of an RNA Molecule Prepared by Transcription in vitro," Science, vol. 223, No. 4631, Jan. 1984, p. 285.
Bass and Cech, Biochemistry, vol. 25, pp. 4473-4477, Aug. 1986.
Bass and Cech, "Specific Interaction Between the Self-Splicing RNA of Tetrahymena and Its Guanosine Substrate: Implications for Biological Catalysis by RNA," Nature, vol. 308, No. 5962, pp. 820-826, 1984.
Been and Cech, "One Binding Site Determines Sequence Specificity of Tetrahymena Pre-rRNA Self-Splicing, Trans-Splicing and RNA Enzyme Activity," Cell, vol. 47, 207-216, Oct. 1986.
Been and Cech, "RNA as an RNA Polymerase: Net Elongation of an RNA Primer Catalyzed by the Tetrahymena Ribozyme," Science, vol. 239, pp. 1412-1416, Mar. 1988.
Been and Cech, "Sites of Circulation of the Tetrahymena rRNA IVS are Determined by Sequence and Influenced by Position and Secondary Structure," Neculeic Acids Research, vol. 13, No. 23, 1985, p. 8389 (Dec. 9, 1985).
BRL Cataloque, pp. 17, 20, and 21, 1985.
Burke et al., "Role of Conserved Sequence Elements 9L and 2 in Self-Splicing of the Tetrahymena Ribosomal RNA Precursor," Cell, vol. 45, 167-176, Apr. 1986.
Buzayan et al., "Satellite Tobacco Ringspot Virus RNA: A Subset of the RNA Sequence is Sufficient for Autolytic Processing," Proc. Natl. Acad. Sci. U.S.A., vol. 83, pp. 8859-8862, Dec. 1986.
Cech, "A Model for the RNA-Catalyzed Replication of RNA," Proc. Natl. Acad. Sci. U.S.A., vol. 83, pp. 4360-4363, Jun. 1986.
Cech, "Mechanism of Self-Splicing of the Ribosomal RNA Precursor of Tetrahymena," Proceedings of the Robert A. Walch Foundation Conferences on Chemical Research XXIX, Nov. 1985, Houston, TX.
Cech, "Ribozymes and Their Medical Implications," J. of the American Medical Association, Nov. 1988, vol. 260, No. 20, pp. 3030-3034.
Cech, "RNA as an Enzyme," Scientific American, vol. 254, No. 11, Nov. 1986.
Cech, Science, vol. 236, pp. 1532-1539, Jun. 1987.
Cech, "Self-Splicing RNA: Implications for Evolution," International Review of Cytology, vol. 93, pp. 4-22, 1985.

(Abstract continued on next page.)

Primary Examiner—Richard A. Schwartz
Assistant Examiner—Richard M. Lebovitz
Attorney, Agent, or Firm—Lyon & Lyon

[57] ABSTRACT

New RNA endoribonuclease ribozymes are found with new conditions to prevent mismatch cleavage and able to cleave RNA after 6 different sets of ribonucleotide 4 base sequences.

22 Claims, 23 Drawing Sheets

Cech, "The Generality of Self-Splicing RNA: Relationship to Nuclear mRNA Splicing," *Cell*, vol. 44, pp. 207–210, 1096.

Cech and Bass, "Biological Catalysis by RNA," *Ann. Rev. Biochem.*, 1986, 55:599–629, Jul. 7, 1986.

Chan et al., "Stability of Group I Intron RNA in Escherichia coli and Its Potential Application in Novel Expression Vector," *Gene*, pp. 02813/1–02813/10, 1988.

Davies et al., "Making Ends Meet: A Model for RNA Splicing in Fungal Mitochondria," *Nature*, vol. 300, 23/30 Dec. 1982, p. 719.

"Designer Enzymes for Genetic Engineers," *New Scientist*, 1987, vol. 114, No. 1545, p. 35.

Forster and Symons, "Self-Cleavage of Plus and Minus RNAs of a Virusoid and a Structural Model for the Active Sites," *Cell*, vol. 49, 211–220, Apr. 1987.

Forster and Symons, "Self-Cleavage of Virsoid RNA Is Performed by the Proposed 55-Nucleotide Active Site," *Cell*, vol. 50, 9–16, Jul. 1987.

Carriga et al., "Mechanism of Recognition of the 5' Splice Site in Self-Splicing Group 1 Introns," *Nature*, vol. 322, Jul. 1986, p. 86.

Guerrier-Takada et al., "The RNA Moiety of Ribonuclease P is the Catalytic Subunit of the Enzyme," *Cell*, vol. 35, pp. 849–857, Dec. 1983.

Haseloff and Gerlach, "Simple RNA Enzymes with New and Highly Specific Endoibonuclease Activities," *Nature*, vol. 334, Aug. 1988, p. 585.

Hutchins et al., "Self-cleavage of Plug and Minus RNA Transcripts of Avocado Sunblotch Viroid," *Nucleic Acids Research*, vol. 14, No. 9, 1986, pp. 3627–3640.17.

Inoue et al., "Intermolecular Exon Ligation of the rRNA Precursor of Tetrahymena: Oligonucleotides Can Function as a 5' Exons," *Cell*, vol. 43, 431–437, Dec. 1985.

Inoue et al., "New Reactions of the Ribosomal RNA Precursor of Tetrahymena and the Mechanism of Self-Splicing," *J. Mol. Biol.*, (1986) 189.

Inoue and Cech, "Secondary Structure of the Circular Form of the Tetrahymena rRNA Intervening Sequence: A Technique for RNA Structure Analysis Using Chemical Probes and Reverse Transcriptase," *Proc. Natl. Acad. Sci. U.S.A.*, vol. 82, pp. 648–652, Feb. 1985.

Kruger et al., "Self-Splicing RNA: Autoexcision and Autocyclization of the Ribosomal RNA Intervening Sequence of Tetrahymena," *Cell*, vol. 31, 147–157, Nov. 1982.

Marsh and Pace, "Ribonuclease P Catalysis Differs from Ribonsomal RNA Self-Splicing," *Science*, vol. 229, No. 4708, Jul. 1985, p. 79.

McSwiggen and Cech, "Sterochemistry of RNA Cleavage by the Tetrahymena Ribozyme and Evidence That the Chemical Step Is Not Rate-Limiting," *Science* 244: 879 (1989).

Michel and Dujon, "Conservation of RNA Secondary Structures in Two Intron Families Including Mitochondrial-, Chloroplast- and Nuclear-Encoded Members," *The EMBO Journal*, vol. 2, No. 1, pp. 33–38, 1983.

North, "Back to the RNA World—and Beyond," *Nature*, vol. 328, Jul. 1987, pp. 18–19.

PCT Application No. 88/04300 (Jun. 16, 1988), Cech et al.

Perea and Jacq, "Role of the 5' Hairpin Structure in the Splicing Accuracy of the Fourth INtron of the Yeast Cob-Box Gene," *The EMBO Journal*, vol. 4, No. 12, pp. 3281–3288, 1985.

Price and Cech, "Coupling of Tetrahymena Ribosomal RNA Splicing to $\beta$-Galactosidase Expression in *Escherichia Coli*," *Science*, vol. 228, pp. 719–722, 1985.

Price et al., *Nuc. Acids Res.*, vol. 13, pp. 1871–1889, Mar.1985).

Prody et al., "Autolytic Processing of Dimeric Plant Virus Satellite RNA," *Science*, Mar. 1986, pp. 1577–1580.

Sullivan and Cech, "Reversibility of Cyclization of the Tetrahymena rRNA Intervening Sequence: Implication for the Mechanism of Splice Site Choice," *cell*, vol. 42, 639–648, 1985.

Szostak, "Enzymatic Activity of the Conserved Core of a Group I Self-Splicing Intron," *Nature*, vol. 322, Jul. 1986, pp. 83–86.

Tanner and Cech, "Self-catalyzed Cyclization of the Intervening Sequence RNA of Tetrahymena: Inhibition by Intercalating Dyes," *Nucleic Acids Research*, vol. 13, No. 21, 1985, p. 7741.

Tanner and Cech, "Self-catalyzed Cyclization of the Intervening Sequence RNA of Tetrahymena: Inhibition by Methidiumpropyl EDTA and Localization of the Major Dye Binding Sites," *Nucleic Acids Research*, vol. 13, No. 21, 1985, p. 7759.

Uhlenbeck, A Small Catalytic Oligoribonucleotide, *Nature*, vol. 328, Aug. 1987, p. 596.

Waring, "Splice-Site Selection by a Self-Splicing RNA of Tetrahymena," *Nature*, vol. 321, May 1986, p. 133.

Waring et al., "Close Relationship Between Certain Nuclear and Mitochondrial Introns," *J. Mol. Biol.*, (1983) 167, 595–605.

Weaver et al., *Proc. Natl. Acad. Sci.*, vol. 68, pp. 2994–2999, 1971.

Westheimer, "Polyribonucleic Acids as Enzymes," *Nature*, vol. 319, 1986, pp. 534–536.

Zaug et al., "Autocatalytic Cyclization of an Excised Intervening Sequence RNA is a Cleavage–Ligation Reaction," *Nature*, vol. 301, Feb. 1983, p. 578.

Zaug and Cech, "Oligomerization of Intervening Sequence RNA Molecules in the Absence of Proteins," *Science*, vol. 229, pp. 1060–1064, 1985.

Zaug et al., "Reactions of the Intervening Sequence of the Tetrahymena Ribosomal Ribonucleic Acid Precursor: pH Dependence of Cyclization and Site-Specific Hydrolysis," *Biochemistry*, 1985, vol. 24, No. 22, p. 6211.

Zaug and Cech, *Science*, vol. 231, pp. 470–475, Jan., 1986.

Zaug et al., *Science*, vol. 224, pp. 574–578, May 1984.

Zaug et al., "Sequence-Specific Endoribonuclease Activity of the Tetrahymena Ribozyme: Enhanced Cleavage of Certain Oligonucleotide Substrates That form Mismatched Ribozyme-Substrate Complexes," *Biochemistry*, 1988, 27, 8924–8931.

Zaug and Cech, "The Tetrahymena Intervening Sequence Ribonucleic Acid Enzyme is a Phosphotransferase and an Acid Phosphatase," *Biochemistry*, 1986, 25, 4478–4482.

Zaug et al., "The Tetrahymena Ribozyme Acts Like an RNA Restriction Endocuclease," *Nature*, 324, Dec. 1986, p. 429.

Cech, "Ribozyme self-replication?", *Nature*, vol. 339, pp. 507–508, Jun. 1989.

Rennie, "In the Beginning", *Scientific American*, pp. 28–29, Sep. 1989.

Sampson et al., "Characterization of Two RNA-catalyzed RNA Cleavage Reactions", *Cold spring Harbor Symposia on Quantitative Biology*, vol. III, pp. 267, 274 (1987).

Stryer, *Biochemistry*, 3rd Edition, 1988, pp. 113, 214, 215, 725–729.

Watson et al. *Mol. Biol. of the Gene*, 4th Edition, vol. II, 1987, 1106–1120, 1136–1137, 1161–1162.

Darnell, *Molecular Cell Biology*, 1986, pp. 355–1148.

Garriga and Lambowitz, "RNA Splicing in Neurospora Mitochondria: Self-Splicing of a Mitochondrial Intron in Vitro", *Cell*, vol. 38, 631–641, 1984.

Gerda van der Horst and Tabak, "Self-Splicing of Yeast Mitochondrial ribosomal and Messenger RNA Precursors", *Cell*, vol. 40, pp. 759–766, 1985. 4n 3070

Ehrenman et al., "Processing of Phage T4 td-encoded RNA is Analogous to the Eukaryotic group I splicing pathway", *Proc. Natl. Acad. Sci., U.S.A.*, vol. 83, pp. 5875–5879, 1986.

Lambowitz, "Infections Introns", *Cell*, vol. 56, 323–326, 1989.

Peebles et al., "A Self-Splicing RNA Excises an Intron Lariat", *Cell*, vol. 44, pp. 213–223, 1986.

R. van der Veen et al., "Excised Group II Introns in Yeast Mitochondria are Lariats and Can Be Formed by Self-splicing In Vitro", *Cell*, vol. 44, 225–234, 1986.

Jarrell et al., "Group II Intron Self-splicing", *J. Biol. Chem.*, vol. 263, No. 7, pp. 3432–3439, 1988.

Sharmeen et al., "Antigenomic RNA of Human Hepatitis Delta Virus Can Undergo Self-Cleavage", *J. of Virology*, vol. 62, No. 8, pp. 2674–2679.

Jacquier and Rosbash, "Efficient Trans-splicing of a Yeast Mitochondrial RNA Group II Intron Implicates a Strong 5' Exon-Intron Interaction", *Science*, vol. 234, pp. 1099–1104, 1986.

Jacquier and Michel, "Multiple Exon-Biding Sites in Class II SelfSplicing Introns", *Cell*, vol. 50, pp. 17–29, 1987.

Watson et al., *Mol. Biol. of the Gene*, Fourth Edition, vol. 1, 1987.

Rawn, *Biochemistry*, pp. 793–199, 1989.

Altman, "Ribonuclease P: An Enzyme with a Catalytic RNA Subunit", *Advances in Enzymology and Related Areas of Mol. Biol.*, 1989.

Zaug and Cech, "Discovery of a New RNA Enzyme", *Abstracts*, Cold Spring Harbor Lab., 1986.

Woodson and Cech, "Reverse Self-Splicing of the Tetrahymena Group I Intron: Implication for the Directionality of Splicing and for Intron Transposition", Cell, 57:335, 1989.

A. D. M. van Mansfeld et al., "Recognition sequence of bacteriophage φX174 gene A protein—an initiator of DNA replication", Nature 288:301,1980. 4n 3085

Rajagopal et al., "Stereochemical Course of Catalysis by the Tetrahymena Ribozyme", Science 244:692, 1989.

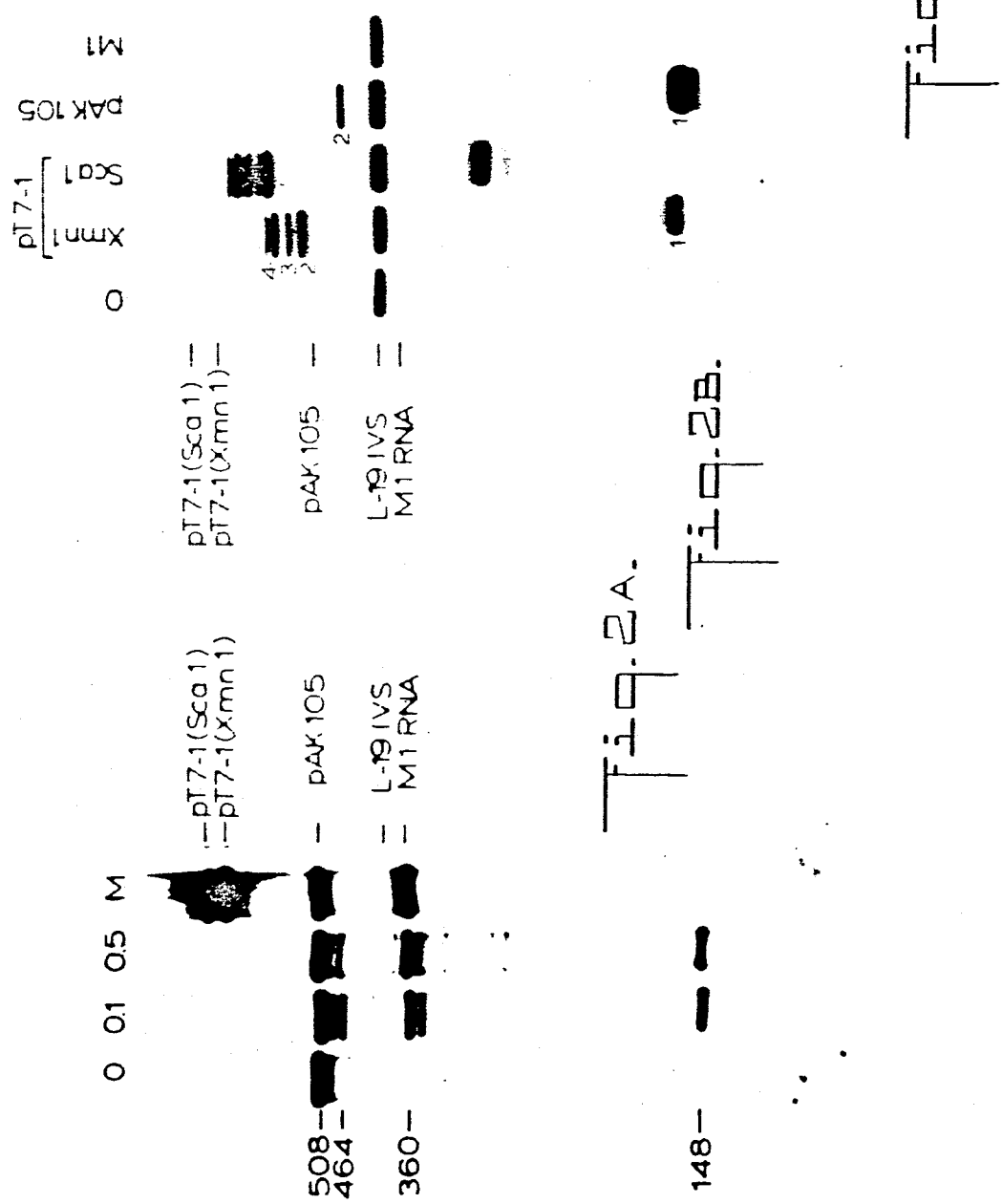

Fig. 4A.
```
          -   0   1   2   5  10  30  60  90 min
GGCCCUCUA5⁻ ▬▬▬▬▬▬▬▬▬▬▬▬▬▬▬▬▬▬
GA5⁻                           ▬   ▬   ▬
```
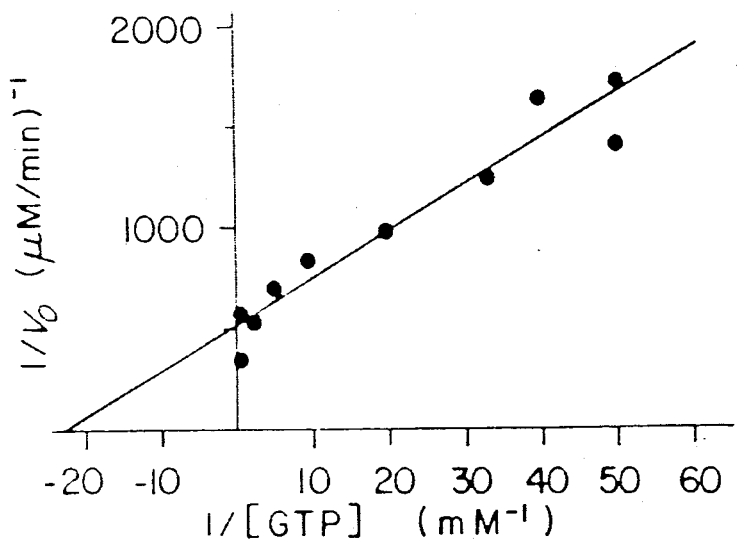
Fig. 4B.
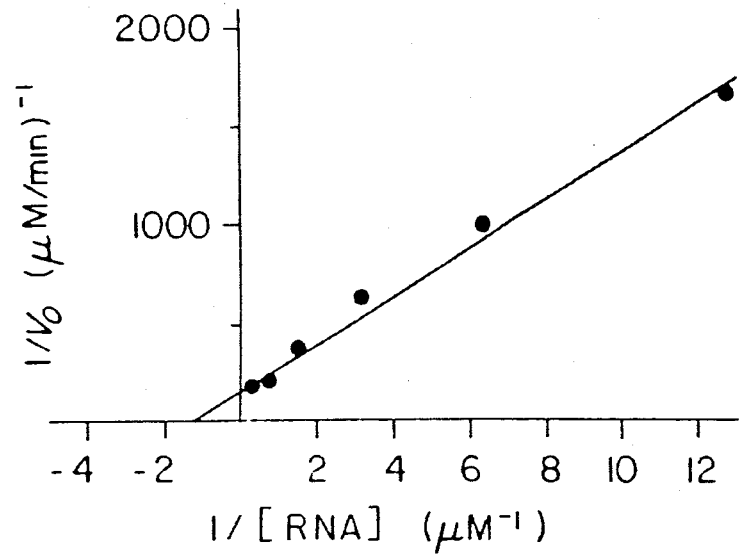
Fig. 4C.

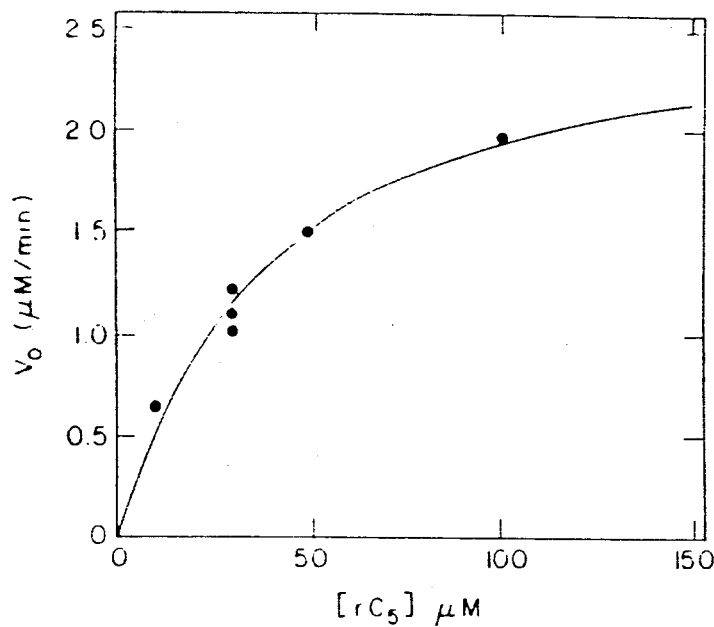

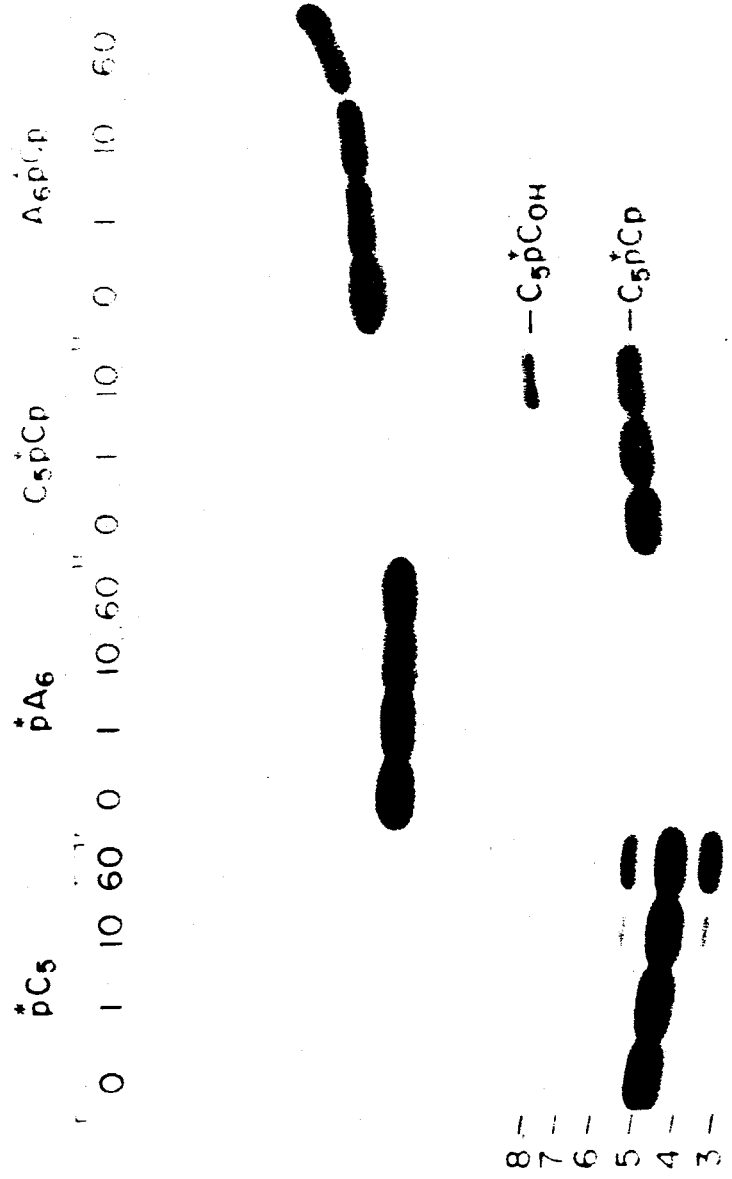
Fig. 11A.
Fig. 11B.

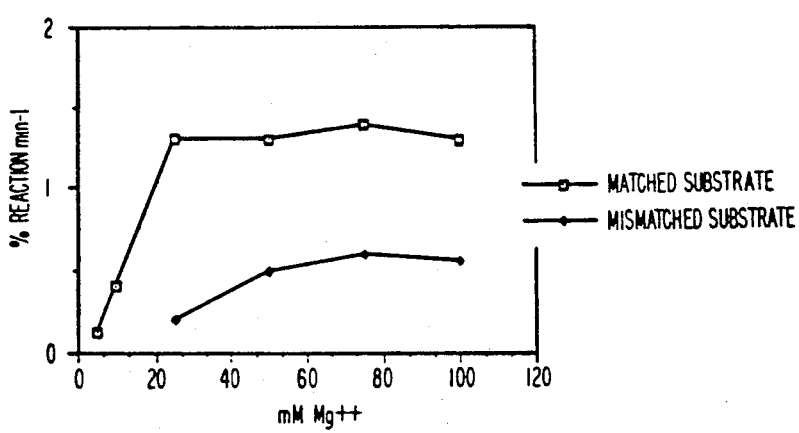
Fig. 26.
Match
Mismatch

RNA RIBOZYME RESTRICTION ENDORIBONUCLEASES AND METHODS

This application is a continuation-in-part of U.S. Ser. No. 937,327 filed Dec. 3, 1986, now U.S. Pat. No. 4,987,071.

The invention was made in part with government funds under Grant GM 28039 from the National Institutes of Health. Therefore, the U.S. Government has certain rights in the invention.

This invention concerns compositions of RNA functioning as an RNA enzyme, i.e. a ribozyme in several capacities: dephosphorylase (acid phosphatase and transphosphorylase), ribonucleotidyl transferase (polymerase activity) and sequence-specific endoribonuclease activities.

SUMMARY

It is found that purified ribonucleic acid (RNA) can serve as an enzyme acting on other RNA molecules in vitro (ribozyme) as a: 1) dephosphorylating enzyme catalyzing the removal of 3' terminal phosphate of RNA in a sequence-specific manner, 2) RNA polymerase (nucleotidyl transferase) catalyzing the conversion of oligoribonucleotides to polyribonucleotides, 3) sequence specific endoribonuclease. (This latter activity is also referred to as RNA restriction endonuclease or endoribonuclease activity.)

DESCRIPTION OF THE DRAWINGS

FIG. 2A, 2B, and 2C show products of cleavage of a variety of RNA substrates by the RNA endoribonuclease.

FIG. 4A, 4B, and 4C show the time course of oligonucleotide cleavage.

FIG. 6 shows the kinetics of conversion of $pC_5$ to larger and smaller oligonucleotides with L-19 IVS RNA.

FIG. 7A, 7B, 7C, and 7D show the enzyme-substrate intermediate of L-19 IVS RNA.

FIG. 11A and 11B show the dephosphorylation of oligo (cytidylic acid) 3-phosphate.

FIG. 17A, 17B, and 17C show increased specificity of cleavage in the presence of urea or formamide.

FIGS. 22-31 show the rate profiles of ribozymes TTC, TTA and TGT for matched and mismatched substrates by urea, $NH_4AC$ or $Mg^{++}$.

DETAILED DESCRIPTION OF THE DRAWINGS

Figure Legends

Figure 1A:
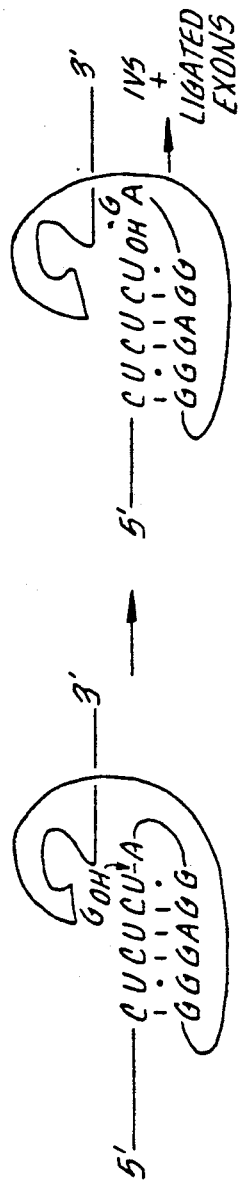
FIG. 1A and 1B compare RNA self-splicing (A) to RNA endoribonuclease activity (B).
Figure 1B:
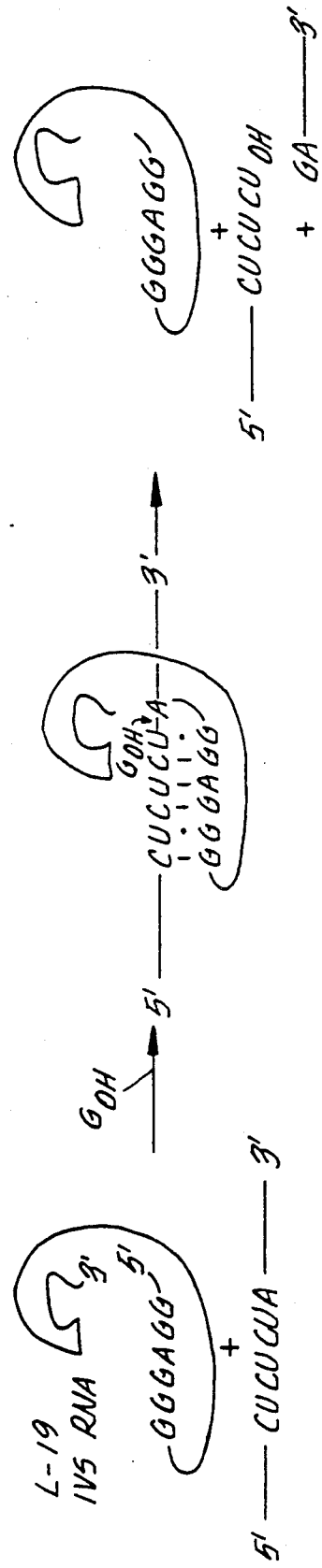

FIG. 1 A model for the L-19 IVS RNA acting like an RNA restriction endonuclease by a mechanism that is an intermolecular version of the first step of pre-rRNA self-splicing. Thin letters and lines represent IVS sequences, boldface letters and thick lines represent exon sequences (above) or substrate RNA sequences (below), and the G in italics is a free guanosine nucleotide or nucleoside.

FIG. 2 The L-19 IVS-beta RNA cleaves large RNA substrates with transfer of guanosine. a, Uniformly labeled 0.6 uM ( u =micro) pAK105 RNA (508 nt) incubated with 0.2 uM L-19 IVS-beta RNA and 0, 0.1 or 0.5 mM GTP (unlabeled) for 1 h under conditions described below. (M) Mixture of 4 substrate RNAs as molecular weight markers. b, Various tritiated RNA substrates (1 ug each) incubated with 0.2 uM L-19 IVS-beta RNA and 120 uM [alpha-$^{32}$P]GTP for 1 h under the same reaction conditions as a. Autoradiogram reveals [$^{32}$p]GTP-labeled products only. The L-19 IVS-beta RNA also becomes GTP-labeled during the incubation. c, Nucleotide sequence of the cleavage product pAK105(1) determined by the enzymatic method (Donis-Keller, H., (1980) Nucleic Acids Res. 8:3133–3142). Some nucleotides could not be assigned due to presence of a band in the untreated (control) RNA sample. G*, labeled GTP joined to the RNA during the reaction.

Methods: L-19 IVS RNA was synthesized by methods similar to those described previously (Zaug, A. J., and Cech, T. R., (1986) Science 231:470–475), except a different RNA polymerase-template system was used. Plasmid pT7-TT1A3 (which contains a T7 RNA polymerase promoter, a 42 bp 5' exon, the entire 413 bp IVS, and an 82 bp 3' exon) was cleaved with Eco RI and transcribed with bacteriophage T7 RNA polymerase (Davanloo, P., et al. (1984) Proc. Nat'l. Acad. Sci. U.S.A. 81: 2035–2039). The transcripts were incubated further under self-splicing, cyclization, and site-specific hydrolysis conditions to produce L-19 IVS RNA (Zaug, A. J., et al. (1984) Science 224:574–578; Zaug, A. J. and Cech, T. R., (1986) Science 231:470–475). The 3'-terminal guanosine was then removed by periodate oxidation and beta-elimination (Winter, G., et al. (1978) Nucleic Acids Res. 5, 3129–3139) to yield L-19 IVS-beta RNA. Substrate RNAs were produced by T7 RNA polymerase transcription of BamHI-cleaved pAK105 (Mount, S. M., et al. (1983) Cell 33:509–518), XmnI- or ScaI-cleaved pT7-1 (purchased from U.S. Biochemical Corp.), and SnaBI-cleaved pDW27, which encodes MI RNA (obtained from D. Wahl and N. Pace). Substrate RNAs were incubated with L-19 IVS-beta RNA in 5 mM $MgCl_2$, 10 mM NaCl, 50 mM Tris-HCl, pH 7.5 at 50° C.; in addition, GTP was present at the concentration indicated. Reactions were stopped by the addition of EDTA to a final concentration of 25 mM. Products were analyzed by electrophoresis in 4% polyacrylamide, 8 M urea gels and subjected to fluorography (a) or autoradiography (b).

FIG. 3 Three different ribozymes can distinguish between sequences that differ by only one single-base change within the recognition element. a, Synthesis of defined oligoribonucleotide substrates by the method of Lowary et al. (Lowary, P., et al. NATO ASI Series A, vol. 110, 69-76, 1986). DNA was transcribed with T7 RNA polymerase in the presence of [alpha-$^{32}$P]ATP to produce oligoribonucleotides labeled with $^{32}$P in the positions indicated (*). b, Proposed interactions between the three oligoribonucleotide substrates (top strands, boldface letters) and the active sites of the matched ribozymes (bottom strands). Arrows designate sites of cleavage and guanosine addition. c, Cleavage of 3 oligoribonucleotide substrates by wild-type and variant L-19 IVS RNAs, assayed by 20% polyacrylamide, 7M urea gel electrophoresis. (−), untreated substrate. In other pairs of lanes, 1.0 uM $^{32}$p-labeled substrate was incubated with 0.125 M ribozyme for 15 min (left lane) or 60 min (right lane) at 50° C. in 10 mM MgCl$_2$, 10 mM NaCl, 50 mM Tris-HCl, pH 7.5, 0.5 mM GTP (unlabeled), 2.5 M urea. Because the $^{32}$P is confined to the nucleotides downstream from the cleavage site, only the smaller of the products is apparent. The identity of the GA$_5$ product was confirmed by treatment of the substrate and reaction mixtures with RNase T$_2$ and monitoring the transfer of $^{32}$P to Gp. The band migrating above GA$_5$ in lanes 2 and 3 was not produced consistently and has not been identified.

Methods: Substrates were prepared by transcription of deoxyoligonucleotides synthesized on an Applied Biosystems DNA Synthesizer. The same promoter top strand was used in each transcription. The bottom strand, which contains promoter and template sequences, was varied to obtain the different RNA substrates. The DNA was transcribed with purified phage T7 RNA polymerase (Davanloo, P., et al. (1984) Proc. Nat'l. Acad. Sci. U.S.A. 81:2035-2039) as described (Lowary, P., et al. NATO ASI Series, vol. 110, as above). Variant ribozymes are described by Been and Cech (Been, M. D., et al. (1986) Cell, 47:207-216). The 24C ribozyme was similarly prepared from transcripts of pBG/-3G:24C. The variant ribozymes were not subjected to beta-elimination to remove their 3'-terminal G.

FIG. 4 Kinetic analysis of the RNA endoribonuclease reaction. a, The oligoribonucleotide substrate (2.5 uM) was incubated with wild-type L-19 IVS-beta RNA (0.2 uM) as in FIG. 3, except that urea was omitted. b, Kinetics of cleavage of GGCCCUCUA$_5$ as a function of GTP concentration. RNA substrate concentration was kept constant at 2.5 uM. c, Kinetics of cleavage as a function of RNA substrate concentration, with GTP concentration kept constant at 0.5 mM.

Methods: Products were separated by polyacrylamide gel electrophoresis. With the autoradiogram as a guide, each gel was cut into strips, and the radioactivity in the unreacted substrate and the GA$_5$ product was determined by liquid scintillation counting. The initial velocity of cleavage (Vo) was determined from a semilogarithmic plot of the fraction of reaction as a function of time. 1/Vo was then plotted as a function of inverse substrate concentration; the graphs are linear least-squares fits to the data points.

FIG. 5 The L-19 IVS RNA catalyzes the cleavage and rejoining of oligoribonucleotide substrates; (A) 10 uM pC$_5$ and (B) 10 uM d-pC$_5$, both with 1.6 uM L-19 IVS RNA; (C) 45 uM pC$_5$ in the absence of L-19 IVS RNA; (D) 45 uM pU$_6$ with 1.6 uM L-19 IVS RNA; (E) 10 uM pC$_5$, (F) 50 uM pC$_5$ and (G) 100 uM pC$_5$, all with 1.6 uM L-19 IVS RNA. Oligonucleotides were 5'-end labeled by treatment with [gamma-$^{32}$P]ATP and polynucleotide kinase; they were diluted with unlabeled oligonucleotide of the same sequence to keep the amount of radioactivity per reaction constant. The L-19 IVS RNA was synthesized by transcription and splicing in vitro. Supercoiled pSPTT1A3 DNA (Price, J. V., et al. (1985) Science 228:719) was cut with Eco RI and then transcribed with SP6 RNA polymerase (Butler, E. T., et al. (1982) J. Biol. Chem. 257:5772; Melton, D. A., et al. (1984) Nucleic Acids Res. 12:7035) for 2 hours at 37° C. in a solution of nucleoside triphosphates (0.5 mM each), 6 mM MgCl$_2$, 4 mM spermidine, 10 mM dithiothreitol, 40 mM tris-HCl, pH 7.5, with 100 units of SP6 RNA polymerase per microgram of plasmid DNA. Then NaCl was added to a final concentration of 240 mM and incubation was continued at 37° C. for 30 minutes to promote excision and cyclization of the IVS RNA. Nucleic acids were precipitated with three volumes of ethanol and redissolved in 50 mM CHES, pH 9.0; MgCl$_2$ was added to a final concentration of 20 mM, and the solution was incubated at 42° C. for 1 hour to promote site-specific hydrolysis of the circular IVS RNA to give L-19 IVS RNA (Zaug, A. J., et al., Science 224, 574 (1984). The reaction was stopped by the addition of EDTA to 25 mM. The L-19 IVS RNA was purified by preparative gel electrophoresis and Sephadex G-50 chromatography. Labeled oligonucleotides were incubated with unlabeled L-19 IVS RNA at 42° C. in 20 mM MgCl$_2$, 50 mM tris, pH 7.5, for 0, 1, 2, 5, 10, 30, and 60 minutes. Reactions were stopped by the addition of EDTA to a final concentration of 25 mM. Products were analyzed by electrophoresis in a 20 percent polyacrylamide, 7M urea gel, autoradiograms of which are shown.

FIG. 6 Kinetics of conversion of pC$_5$ to larger and smaller oligonucleotides with 1.6 uM L-19 IVS RNA. Products were separated by polyacrylamide gel electrophoresis. With the autoradiogram as a guide, the gel was cut into strips and the radioactivity in each RNA species was determined by liquid scintillation counting. The amount of reaction at each time was taken as the radioactivity in pC$_3$+pC$_4$+pC$_6$+pC$_7$+ ... divided by the total radioactivity in the lane. The initial velocity of product formation, V$_o$, was determined from a semilogarithmic plot of the fraction of reaction as a function of time. V$_o$ was then plotted as a function of substrate concentration; the line is a least-squares fit to the Michaelis-Menten equation. The resulting kinetic parameters are K$_m$=42 uM, V$_{max}$=2.8 uM min$^{-1}$, and k$_{cat}$=1.7 min$^{-1}$. The kinetic parameters for the first and second steps in the reaction have not yet been determined separately.

FIG. 7 Formation and resolution of the covalent enzyme-substrate intermediate. (A) To form the covalent L-19 IVS RNA-substrate intermediate, 8.5 nM C$_5$p* was treated with 0.16 uM L-19 IVS RNA under standard reaction conditions for 0 to 60 minutes. (B) p*C$_5$ (0.01 uM) was reacted with 0.16 uM L-19 IVS RNA. Cleavage occurred normally, but there was very little rejoining. (C) Labeled covalent intermediate was prepared as in (A) (60 minutes) and purified by electrophoresis in a 4 percent polyacrylamide, 8M urea gel. It was then incubated with 10 uM unlabeled C$_5$ under standard reaction conditions for 0 to 60 minutes. The product designated $C_6$ comigrated with labeled $C_6$ marker (not shown). (D) Isolated covalent intermediate as in (C) was incubated under site-specific hydrolysis conditions (20 mM $MgCl_2$, 50 mM CHES, pH 9.0) at 42° C. for 0 to 60 minutes. Positions of labeled mono- and dinucleotide markers are indicated. In the 10- and 30-minute lanes of (A) and the 10-, 30-, and 60-minute lanes of (C), band compression (reduced difference in electrophoretic mobility) is seen between $C_6$ and $C_7$ and to a lesser extent between $C_7$ and $C_8$. This is due to the absence of a 5' phosphate. Thus, the charge-to-mass ratio is increasing with chain length, whereas with 5'-phosphorylated oligonucleotides the charge-to-mass ratio is independent of chain length. When such products were phosphorylated by treatment with polynucleotide kinase and ATP, the distribution was converted to the normal spacing as in Fig. 1 [Zaug, A., et al. (unpublished data)].

Figure 8:
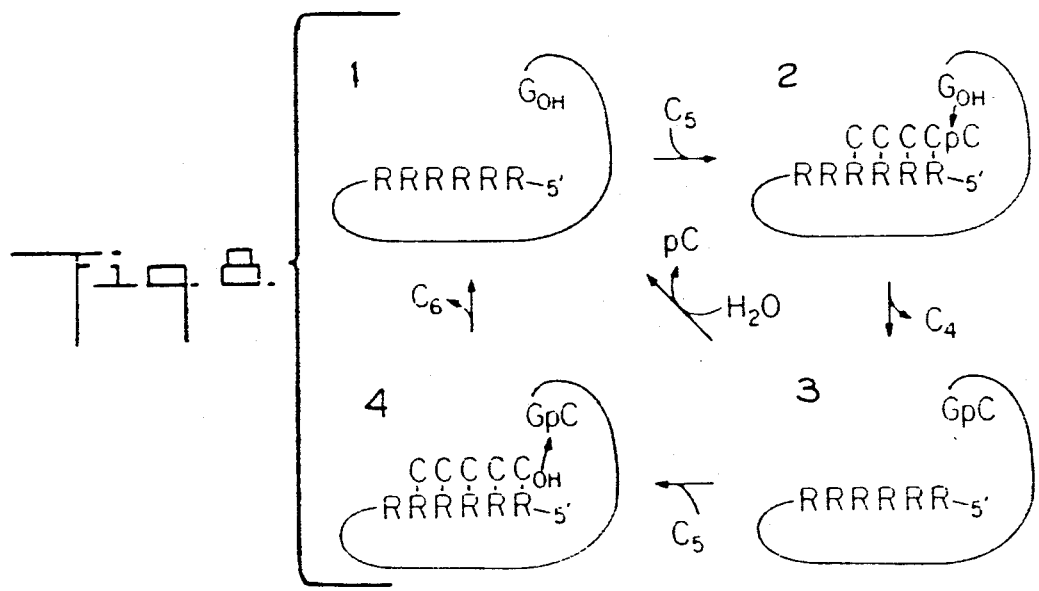
FIG. 8 is a model for enzymatic mechanism of L-19 IVS RNA acting as a ribonucleotidyl transferase.

FIG. 8 Model for the enzymatic mechanism of the L-19 IVS RNA. The RNA catalyzes cleavage and rejoining of oligo(C) by the pathway 1 - 2 - 3 - 4 - 1. The L-19 IVS RNA enzyme (1) is shown with the oligopyrimidine binding site (RRRRRR, six purines) near its 5' end and $G^{414}$ with a free 3'-hydroxyl group at its 3' end. The complex folded core structure of the molecule (Davies, R. W., et al., (1982) Nature (London) 300:719; Waring, R. B., et al. (1983) J. Mol. Biol. 167:595; Michel, F., et al. (1983) EMBO J. 2:33; Cech, T. R., et al. (1983) Proc. Nat'l. Acad. Sci. U.S.A. 80:3903; Inoue, T., et al. (1985) ibid 82:648) is simply represented by a curved line. The enzyme binds its substrate ($C_5$) by Watson-Crick base-pairing to form the noncovalent enzyme-substrate complex (2). Nucleophilic attack by $G^{414}$ leads to formation of the covalent intermediate (3). With the pentanucleotide $C_5$ as substrate, the covalent intermediate is usually loaded with a single nucleotide, as shown; with substrates of longer chain length, an oligonucleotide can be attached to the 3' end of $G^{414}$. If $C_5$ binds to the intermediate (3) in the manner shown in (4), transesterification can occur to give the new product $C_6$ and regenerate the enzyme (1). Note that all four reactions in this pathway are reversible. When acting as a ribonuclease, the L-19 IVS RNA follows the pathway 1 - 2 - 3 - 1. The covalent intermediate (3) undergoes hydrolysis, releasing the nucleotide or oligonucleotide attached to its 3' end (in this case pC) and regenerating the enzyme (1).

Figure 9A:
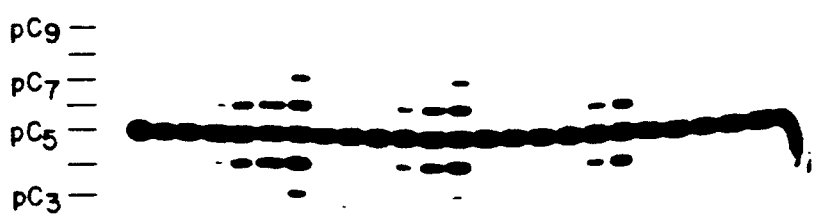
FIG. 9A, 9B, and 9C show the competitive inhibition of $pC_5$ reaction by $dC_5$.
Figure 9B:
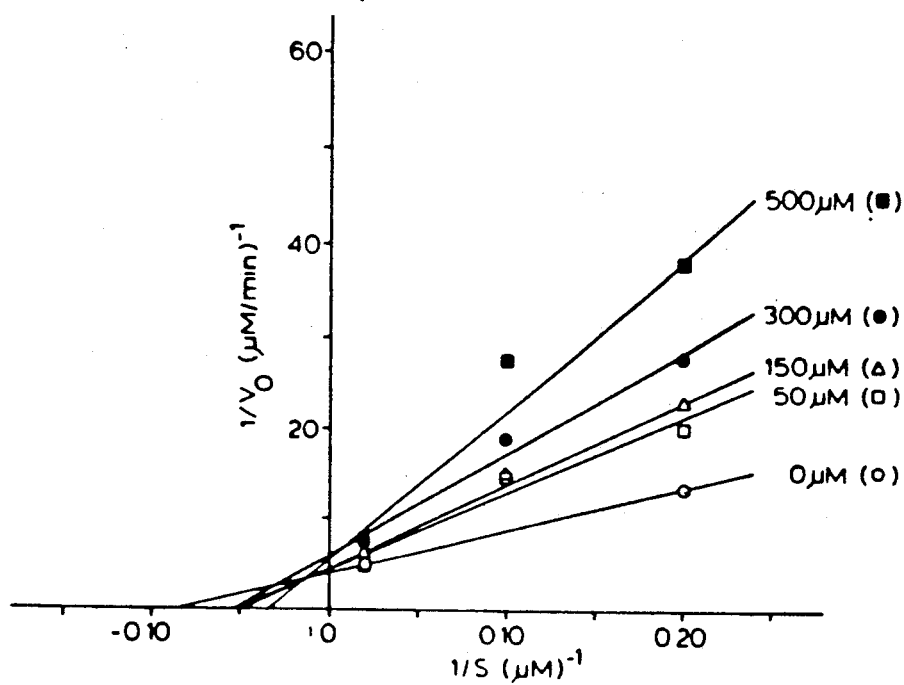
Figure 9C:
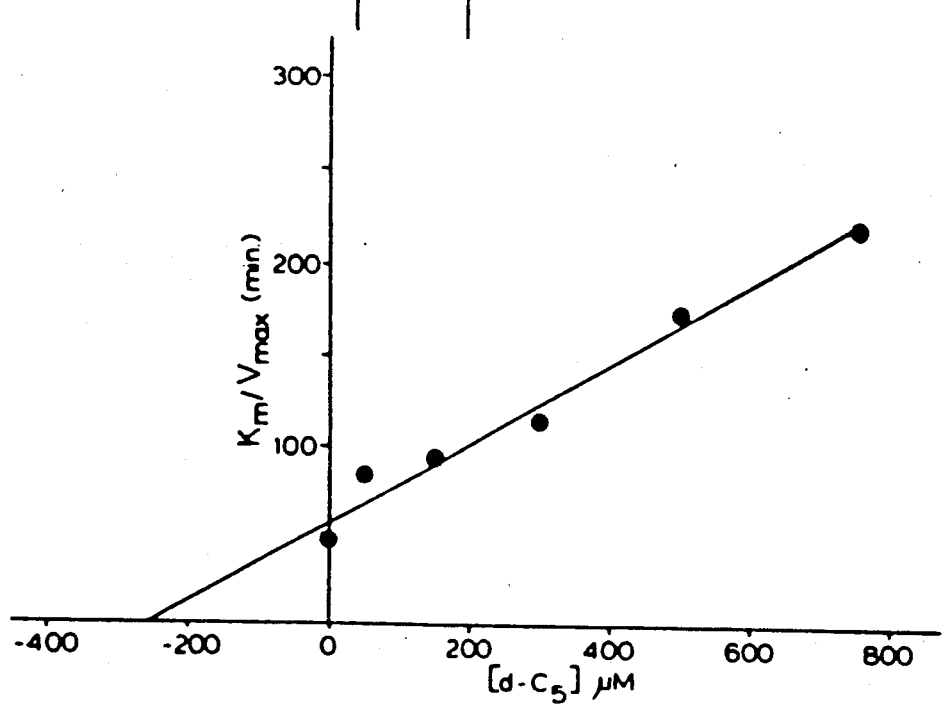

FIG. 9. Competitive inhibition of the $pC_5$ reaction by d-$C_5$ (A) 5 uM p*$C_5$, shown unreacted in lane 0, was incubated with 0.16 uM L-19 IVS RNA under standard reaction conditions. Reactions were done in the absence of d-$C_5$ or in the presence of 50 uM, 500 uM, or 1000 uM d-$C_5$ as indicated. (B) Lineweaver-Burk plots of the rate of conversion of $pC_5$ to $pC_4 + pC_3$ in the presence of (o) 0 uM, (open square) 50 uM, (open triangle) 150 uM, (closed circle) 300 uM, or (closed square) 500 uM unlabeled d-$C_5$. The analysis was limited to the smaller products because their production is affected only by the first transesterification reaction (FIG. 8). Although d-$C_5$ is inactive in the first transesterification reaction, it has some activity as a substrate in the second transesterification reaction (Zaug, A., et al. unpublished data) and therefore could affect the production of chains of length greater than 5. (C) $K_m/V_{max}$, determined from the slopes of the lines in (B), is plotted against the inhibitor concentration. The x-intercept gives the negative of $K_i$; $K_i = 260$ uM.

Figure 10:
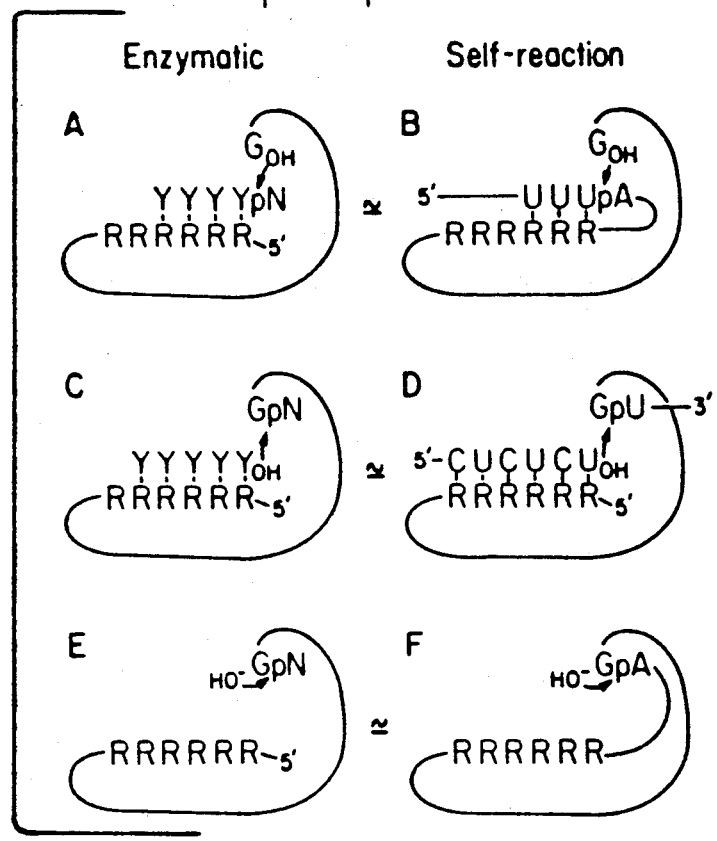
FIG. 10 shows the relation of reactions catalyzed by the L-19 IVS RNA to self-splicing and related IVS RNA-mediated reactions.

FIG. 10 Relation of reactions catalyzed by the L-19 IVS RNA to self-splicing and the related IVS RNA-mediated reactions. Formation of the covalent enzyme-substrate intermediate (A) is analogous to IVS RNA autocyclization (B). Resolution of the enzyme-substrate intermediate (C) is analogous to exon ligation (D) or the reversal of cyclization (Sullivan, F. X. and Cech, T. R. (1985) Cell 42:639). Hydrolysis of the enzyme-substrate intermediate (E) is analogous to site-specific hydrolysis of the circular IVS RNA (F) or the pre-rRNA (Inoue, T., et al. (1986) J. Mol. Biol. 189:143-165).

FIG. 11 The L-19 IVS RNA catalyzes the dephosphorylation of oligo(cytidylic acid) 3'-phosphate. (A) L-19 IVS RNA (0.16 uM) was incubated with p*$C_5$ (10 uM), p*$A_6$ (10 uM), $C_5$p*Cp(about 2 nM), $A_6$p*Cp (about 3 nM) in 20 mM $MgCl_2$ and 50 mM Tris-HCl, pH 7.5, at 42° C. for the times indicated. Reaction products were separated by electrophoresis in a 20% polyacrylamide-7 M urea sequencing gel, an autoradiogram of which is shown. (B) L-19 IVS RNA (0.2 uM) was incubated with $C_5$p* (about 2 nM) as above. The phosphoenzyme E-p* is the L-19 IVS RNA with a 3'-terminal phosphate monoester. Gel electrophoresis and autoradiography as in (A). Only a portion of the 5-min sample was loaded on the gel.

FIG. 12 Effect of pH on the phospho transfer and nucleotidyl transfer reactions. (A) Lane 1, untreated $C_5$p*Cp; lanes 2-11, $C_5$p*Cp (15 nM) incubated with excess L-19 IVS RNA (500 nM) in 20 mM $MgCl_2$ and 50 mM buffer (NaOAc for pH 4.0 and 5.0, Tris-HCl for pH 7.5, CHES for pH 9.0 and 10.0); lane 12, $C_5$p*Cp treated with calf intestinal phosphatase to provide a marker for $C_5$p*C-OH; lane 13, untreated p*$C_5$; lanes 14-23, p*$C_5$ (15 nM) incubated with excess L-19 IVS RNA (500 nM) as in lanes 2-11. Reactions proceeded at 42° C. for the indicated times, after which they were stopped by the addition of an equal volume of urea sample buffer containing 50 mM EDTA. (B) $C_5$p*Cp (about 2 nM) was incubated with L-19 IVS RNA (0.2 uM) at pH 5.0 for the times indicated. (C) Data similar to those shown in (B) except with 15 nM $C_5$p*Cp were quantitated by liquid scintillation counting of the sliced gel. Semilogarithmic plots, which were linear for the first three or four time points, were used to determine $t_{\frac{1}{2}}$. The observed first-order rate constant ($k_{obsd}$) was calculated as $(\ln 2)/t_{\frac{1}{2}}$. NaOAc buffer was used for pH 4.0 and 5.0, MES for pH 5.5 and 6.0, and Tris-HCl for pH 7 (estimate based on a single point that showed about 50% reaction).

Figure 13:
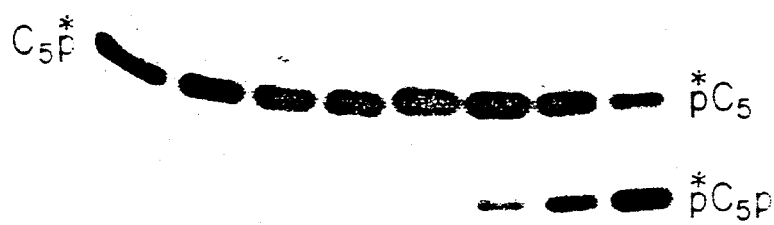
FIG. 13 shows that the phosphorylation of L-19 IVS RNA ribozyme is reversible.

FIG. 13. Phosphorylation of the enzyme is reversible. L-19 IVS RNA (0.2 uM) was phosphorylated by incubation with 2.5 uM unlabeled $C_5$p for min at 42° C. at pH 5.0. A trace amount of (A) $C_5$p* (1.2 nM) or (B)p*$C_5$(20 nM) was then added to the unlabeled E-p, and incubation was continued for the times shown.

FIG. 14. The L-19 IVS RNA acts catalytically as a phosphotransferase. (A) Decreasing concentrations of $C_5$p* were incubated for 30 min with 0.32 uM L-19 IVS RNA and 100 uM unlabeled UCU-OH. The specific radioactivity of $C_5$p* was adjusted by addition of unlabeled $C_5$p* to keep the amount of radioactivity constant among samples. The small amount of intermediate band seen in some reactions is presumed to be UCUCp formed by attack of UCU on an E-pCp covalent intermediate. (-lane) $C_5$p* prior to incubation. (B) $C_5$p* (2.5 uM) incubated with 0.16 uM L-19 IVS RNA and 200 uM unlabeled UCU-OH. (C) Quantitation of data shown in (B), including labeled E-p, which ran near the top of the gel. In all cases, incubation was in 20 mM MgCl$_2$ and 50 mM MES, pH 6.0, at 42° C.

FIG. 15. Single active site model for the activity of the L-19 IVS RNA on phosphate diester and phosphate monoester substrates. (A) Reversible nucleotidylation of the L-19 IVS RNA, proposed to be the key step in the poly(C) polymerase reaction (Zaug & Cech, (1986) Science (Wash. D.C. 231:470-475. (B) Reversible phosphorylation of the L-19 IVS RNA, which allows the enzyme to act as a phosphotransferase. In both cases, the oligo(C) substrate base pairs to the oligo(Pyrimidine) binding site (six R's) to form a noncovalent complex. The binding site is nucleotides 22-27 of the IVS RNA and has the sequence GGAGGG (M. D. Been and T. R. Cech, (1986) Cell 47:206-216). Nucleophilic attack by the 3'-hydroxyl of the active site guanosine, G$^{414}$, leads to formation of E-pC (A) or E-p (B) and the release of C$_5$. The complex folded core structure of the IVS is depicted as a simple curved line.

Figure 16:
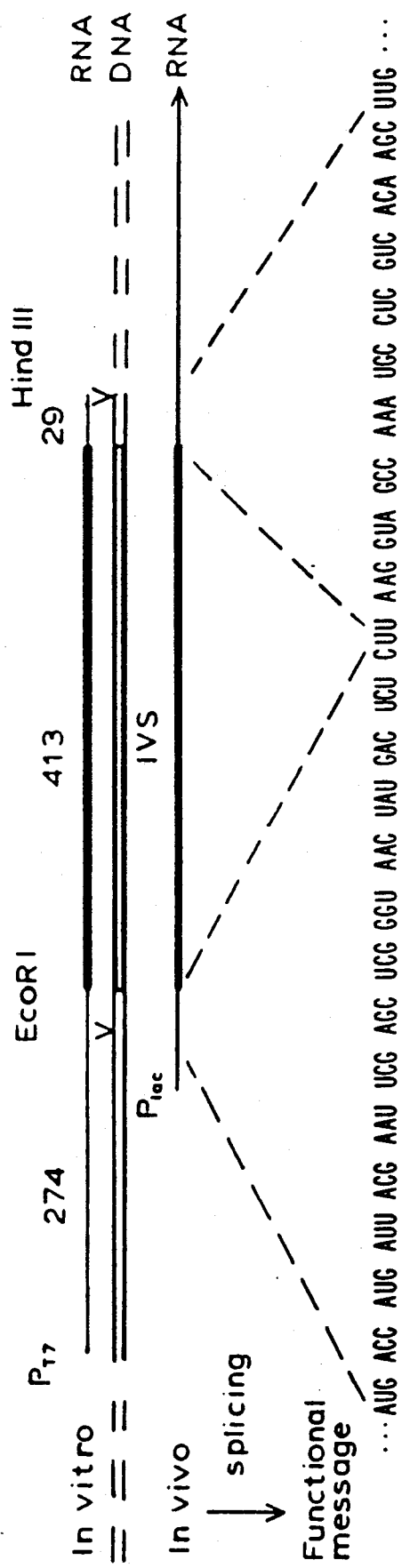
FIG. 16 shows the plasmid construction which produces the L-21 IVS RNA.

FIG. 16 Plasmid pBGST7 contains a fragment with the IVS inserted into the multicloning site of a small pUC$_{18}$ derivative which in turn contains a phage T7 promoter. The double line represents the plasmid DNA with the IVS. The relative positions of the promoters are indicated. The positions of the EcoRI and Hind III site are indicated by the arrowheads. The upper line represents the in vitro transcript made from purified plasmid DNA with phage T7 RNA polymerase. The numbers above it refer to the length, in nucleotides, of the exons and IVS. The lower line represents the in vivo transcript of the 5' end of lacZ'. The IVS (heavy line) contains stop codons in all three reading frames, so a functional alpha fragment can only be produced if the IVS is excised and the exons are joined by splicing in *E. coli*.

FIG. 17 Increased specificity of cleavage in the presence of urea or formamide. (a) An oligonucleotide substrate (GGCCCUCUA$_5$) of length 13, $^{32}$P labeled at its 5' end, was incubated with the wild-type (wt L-19 IVS-$_{beta}$RNA or the 24C variant, both prepared as described by Zaug et al. Nature (1986). Diagrams show the proposed base-paired complexes between the substrate (top strand) and the active site of the ribozyme (bottom strand). Reactions contain 0.12 uM substrate, 0.05uM ribozyme, 0.5 mM GTP, 10 mM NaCl, 10 mM MgCl$_2$,50 mM Tris-Hcl, pH 7.5, and the indicated concentration of urea. Incubation was at 50° C. for 15 or 60 min as indicated. Samples were analyzed by electrophoresis in a 20% polyacrylamide/7 M urea gel, an autoradiogram of which is shown. (b) An oligonucleotide substrate (GGCCGCUA$_5$) of length 12 was incubated with the wild-type L-19 IVS$_{beta}$RNA or the 24C variant. Conditions as described in (a), except with 1.0 uM substrate and 0.10 uM ribozyme. (c) Same substrate and reaction conditions as in (b), except formamide was used instead of urea. (2.5 M formamide is 10% v/v). Cleavage by the 24C variant ribozyme surpassed cleavage by the wt ribozyme between 1.0 and 2.0 M formamide.

Figure 17A:
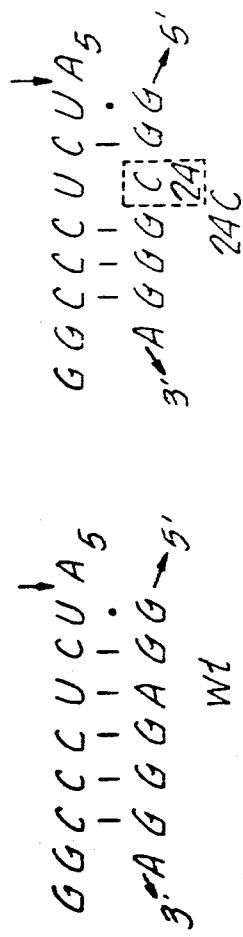
Figure 18:
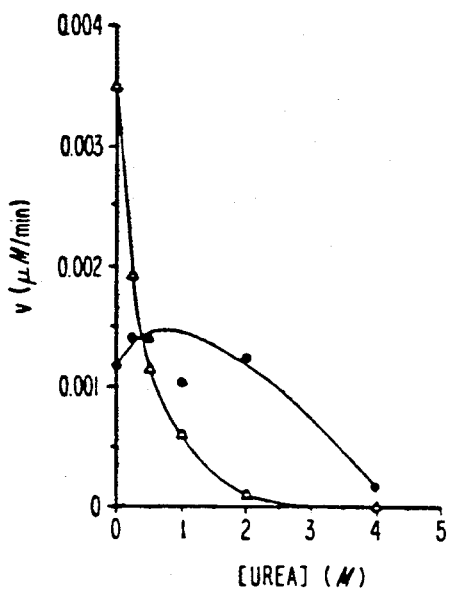
FIG. 18 shows mismatch sensitivity to urea.

FIG. 18 Cleavage of oligonucleotide substrate that forms a mismatched ribozyme-substrate complex is very sensitive to urea. Data from 15-min points of FIG. 17a were quantitated by liquid scintillation counting of the sliced gel. ●, wt ribozyme. ▲, 24C variant ribozyme (mismatched complex).

Figure 19:
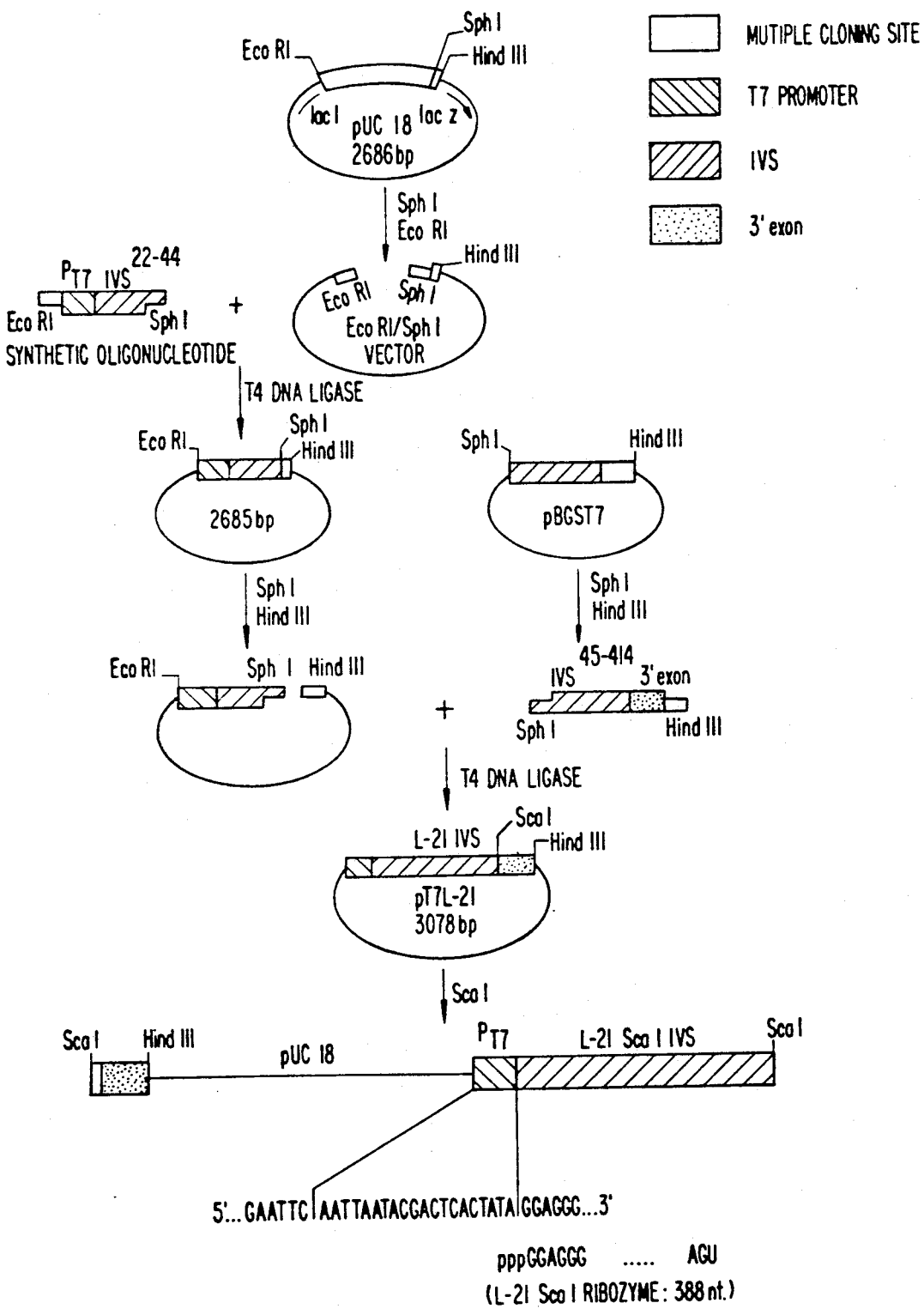
FIG. 19 shows constriction of pTL-21 plasmid.

FIG. 19 Construction of pT7L-21, a plasmid that facilitates synthesis of the wild-type ribozyme (L - 21 ScaI RNA). The pUC$_{18}$ vector was prepared by removing the SphI/EcoRI fragment from the multiple cloning site. A synthetic DNA fragment containing an EcoRI end with a 5' overhang, a promoter for bacteriophage T$_7$ RNA polymerase (Dunn & Studier, (1983) J. Mol. Biol. 166:477-535), and bases 22-44 of the *Tetrahymena thermophila* rRNA IVS (including the SphI end with its 3' overhang) was inserted into the vector. This plasmid was cloned and sequenced and then cleaved with SphI and HindIII. The 395 bp SphI/HindIII fragment of pGST7 (Been & Cech, (1986) Cell (Cambridge, Mass.) 47:207-216), containing bases 45-414 of the IVS plus 25 bases of the 3' exon, was inserted to give pT7L-21. pT7L-21 is linearized with ScaI restriction endonuclease, truncating the template in the IVS five nucleotides upstream from the 3' splice site. Transcription with purified T$_7$ RNA polymerase in vitro then gives the L - 21 ScaI RNA, which contains nucleotides 22-409 of the IVS.

Figure 20:
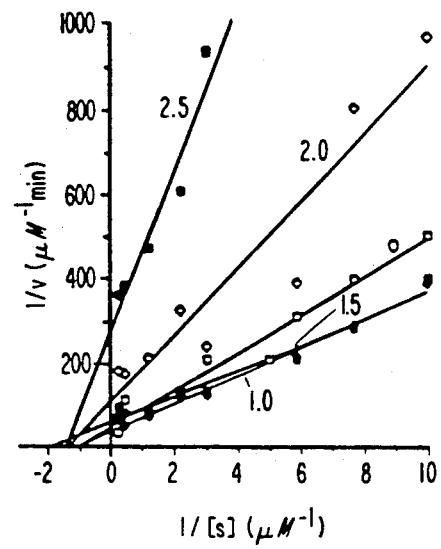
FIG. 20 show urea effect.

FIG. 20 Effect of urea concentration on the rate of cleavage of the GGCCCGCUA$_5$ substrate by L - 21 ScaI RNA. Ribozyme concentration was 0.01 uM; oligonucleotide substrate concentration ranged from 0.10 to 3.78 uM. Urea concentrations (M) are indicated.

Figure 21:
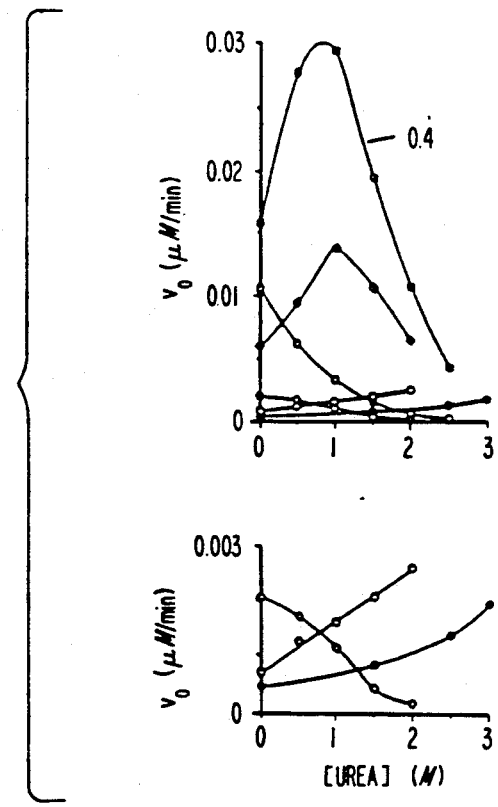
FIG. 21 shows urea effect using L - 21 RNA.

FIG. 21 Effect of urea concentration on the rate of cleavage of oligonucleotide substrates by the L - 21 ScaI RNA. Oligonucleotide substrates contained the recognition sequences CCCCCU (■), CCCGCU (♦), CCCUCU (●), CUCCCU (□), CUCGCU (◊), and CUCUCU (○). In each case, the recognition sequence was preceded by two G residues and followed by five A residues. Reactions contained 0.80 uM oligonucleotide and 0.01 uM L - 21 ScaI RNA. All velocities are initial velocities except for the CCCCCU-containing substrate, where cleavage proceeded so rapidly that some of the velocities are based on data points where a large fraction of the substrate was cleaved; in this case, initial velocity is underestimated.

FIGS. 22-31 show the effect of urea, NH$_4$Ac or Mg on the rate profiles of ribozymes TTC, TTA and TGT for cleavage of matched and mismatched substrates.

DESCRIPTION

The Tetrahymena rRNA intervening sequence (IVS) is a catalytic RNA molecule or ribozyme. It mediates RNA self-splicing, accomplishing its own excision from the large ribosomal RNA precursor, and subsequently converts itself to a circular form (Kruger, K., et al. (1982) Cell 31:147-157; Zaug, A. J., et al. (1983) Nature 301:578-583). In these reactions, the splice sites and cyclization sites can be viewed as intramolecular substrates for an activity that resides within the IVS RNA (Zaug, A. J., et al. (1984) Science 224:574-578). This is not a true enzymatic reaction however since the RNA is not regenerated in its original form at the end of the self-splicing reaction. The IVS RNA when in its linear form is referred to as L IVS RNA.

This view has been validated by studies of the L-19 IVS RNA, a linear form of the IVS which is missing the first 19 nucleotides. Because it lacks the cyclization sites, the L-19 IVS RNA cannot undergo intramolecular reactions (Zaug, A. J., et al. (1984) Science 224:574-578). It still retains activity, however, and can catalyze cleavage-ligation reactions on other RNA molecules (Zaug, A. J. and Cech, T. R. (1986) Science 231:470-475). When provided with oligo(cytidylic acid) as a substrate, the L-19 IVS RNA acts as an enzyme with nucleotidyltransferase [poly(C) polymerase] and phosphodiesterase (ribonuclease) activities (Zaug, A. J. and Cech, T. R. (1986) Science 231:470–475). With 3′-phosphorylated oligo(C) substrates, the same ribozyme acts as a phosphotransferase and an acid phosphatase (Zaug, A. J. and Cech, T. R. (1986) Biochemistry 25:4478–4482). A key mechanistic feature of all four of these reactions is the formation of a covalent enzyme-substrate intermediate in which a nucleotide or phosphate is esterified through the 3′-O of $G^{414}$, the 3′ terminal guanosine of the IVS RNA. In addition, we describe herein a fifth enzymatic activity concerning the endoribonuclease activity of the L-19 IVS RNA on other RNA molecules.

Following self-splicing of the Tetrahymena rRNA precursor, the excised IVS RNA (Abbreviations: IVS, intervening sequence or intron; L-19 IVS RNA (read "L minus 19"), a 395-nt RNA missing the first 19 nt of the L IVS RNA (the direct product of pre-ribosomal RNA splicing); p*, $^{32}$P within an oligonucleotide, that is $C_5p^*C$ is $CpCpCpCpC^{32}pC$ and $p^*C_5$ is $^{32}pCpCpCpCpC$; d-$C_5$, deoxy$C_5$) undergoes a series of RNA-mediated cyclization and site-specific hydrolysis reactions. The final product, the L-19 IVS RNA, is a linear molecule that does not have the first 19 nucleotides of the original excised IVS RNA (Zaug, A. J., et al., Science 224:574 (1984). We interpreted the lack of further reaction of the L-19 species as an indication that all potential reaction sites on the molecule that could reach its active site (that is, intramolecular substrates) had been consumed; and we argued that the activity was probably unperturbed (Zaug, A. J., et al., Science 224:574 (1984) (L IVS RNA is linear IVS RNA). We have now tested this by adding oligonucleotide substrates to the L-19 IVS RNA. We find that each IVS RNA molecule can catalyze the cleavage and rejoining of many oligonucleotides. Thus, the L-19 IVS RNA is a true enzyme. Although the enzyme can act on RNA molecules of large size and complex sequence, we have found that studies with simple oligoribonucleotides like pC$_5$ (pentacytidylic acid) have been most valuable in revealing the minimum substrate requirements and reaction mechanism of this enzyme.

Nucleotidyltransferase or RNA Polymerase Activity

When the shortened form of the self-splicing ribosomal RNA (rRNA) intervening sequence of Tetrahymena thermophila acts as a nucleotidyl transferase, it catalyzes the cleavage and rejoining of oligonucleotide substrates in a sequence-dependent manner with $K_m=42$ uM and $k_{cat}=2$ min$-1$. The reaction mechanism resembles that of rRNA precursor self-splicing. With pentacytidylic acid as the substrate, successive cleavage and rejoining reactions lead to the synthesis of polycytidylic acid. When the active site is changed from the natural nucleotide sequence GGAGGG to the sequence GAAAAG, oligouridylic acid is polymerized to polyuridylic acid [Been and Cech, Cell 47:207 (1986)]. Thus, the RNA molecule can act as an RNA polymerase, differing from the protein enzyme in that it uses an internal rather than an external template. Thus various heteropolymers would be constructed by variant RNA enzyme forms. This predicts the formation for example of messenger RNA molecules for particular peptides or proteins. This messenger could be synthesized with or without introns. At about pH 9, the same RNA enzyme has activity as a sequence-specific ribonuclease.

With $C_5$ as substrate, the L-19 IVS RNA makes poly(C) with chain lengths of 30 nucleotides and longer, acting as an RNA polymerase or nucleotidyl transferase. Thus longer oligonucleotides (polynucleotides) can be formed from short oligonucleotide starting material. The number of P-0 bonds is unchanged in the process. In the synthesis of poly(C) on a poly(dG) template by RNA polymerase, one CTP is cleaved for each residue polymerized. Thus, the RNA polymerase reaction is also conservative with respect to the number of P-O bonds in the system. The L-19 IVS RNA can therefore be considered to be a poly(C) polymerase that uses $C_4pC$ instead of pppC as a substrate. It incorporates pC units at the 3′ end of the growing chain and releases $C_4$; the $C_4$ is analogous to the pyrophosphate released by RNA polymerase. Synthesis is directed by a template, but the template is internal to the RNA enzyme. It may be possible to physically separate the template portion from the catalytic portion of the RNA enzyme with retention of activity. If so, the RNA enzyme could conceivably act as a primordial RNA replicase, catalyzing both its own replication and that of other RNA molecules (T. R. Cech, (1986) Proc. Nat'l. Acad. Sci. USA 83:4360–4363.

The L-19 IVS RNA catalyzes the cleavage-ligation of pC$_5$ with $K_m=42$ uM, $k_{cat}=2$ min$^{-1}$, $k_{cat}/K_m=1\times10^3$ sec$-1$ M$^{-1}$. The $K_m$ is typical of that of protein enzymes. The $k_{cat}$ and $k_{cat}/K_m$ are lower than those of many protein enzymes. However, $k_{cat}$ is well within the range of values for proteins that recognize specific nucleic acid sequences and catalyze chain cleavage or initiation of polymerization. For example, Eco RI restriction endonuclease cleaves its recognition sequence in various DNA substrates, including a specific 8-bp DNA fragment, with $k_{cat}=1$ min$^{-1}$ to 18 min$^{-1}$ (Greene, P. J., et al. (1975) J. Mol. Biol. 99:237; Modrich, et al. (1976) J. Biol. Chem. 251:5866; Wells, R. D., et al. (1981) Enzymes 14:157; Brennan, M. B., et al. in preparation; and Terry, B., et al. in preparation). The $k_{cat}$ is also similar to that of the RNA enzyme ribonuclease P, which cleaves the precursor to tRNA with $k_{cat}=2$ min$^{-1}$ (Guerrier-Takada, C., et al. (1983) Cell 35:849; Marsh, T. L., et al. in Sequence Specificity in Transcription and Translation, R. Calendar and L. Gold Eds., UCLA Symposium on Molecular and Cellular Biology (Plenum, New York, in press)).

Another way to gauge the catalytic effectiveness of the L-19 IVS RNA is to compare the rate of the catalyzed reaction to the basal chemical rate. A transesterification reaction between two free oligonucleotides has never been observed, and hence the uncatalyzed rate is unknown. On the other hand, the rate of hydrolysis of simple phosphate diesters has been studied (Kumamoto, J., et al. (1956) J. Am. Chem. Soc. 78:4858; P. C. Haake et al. ibid. (1961) 83:1102; Kirby, A. J., et al. (1970) J. Chem. Soc. Ser. B., p. 1165; Bunton, C. A., et al. (1969) J. Org. Chem. 34:767)). The second-order rate constant for alkaline hydrolysis of the labile phosphodiester bond in the circular IVSRNA (Zaug, A. J., et al. (1985) Biochemistry 24:6211) is 12 orders of magnitude higher than that of dimethyl phosphate (Kumamoto, J., et al. (1956) Supra) and ten orders of magnitude higher than that expected for a normal phosphodiester bond in RNA (The rate of nucleophilic attack by hydroxide ion on phosphate esters is sensitive to the pK$_a$ of the conjugate acid of the leaving group. A phosphate in RNA should be more reactive than dimethyl phosphate, because pK$_a=12.5$ for a nucleoside ribose and pK$_1=15.5$ for methanol [values at 25° C. from P.O.P. T'so, Basic Principles in Nucleic Acid Chemistry (Academic Press, New York, (1974), vol. I, pp. 462-463 and P. Ballinger and F. A. Long, J. Am. Chem. Soc. 82:795 (1960), respectively). On the basis of the kinetic data available for the alkaline hydrolysis of phosphate diesters (Kumamoto, J., et al. (1956) J. Am. Chem. Soc. 78:4858; Haake, P. C. (1961) et al. ibid. 83:1102; Kirby, A. J., et al. (1970) J. Chem. Soc. Ser. B., p. 1165; Bunton, C. A., et al. (1969) J. Org. Chem. 34:767), the slope of a graph of the logarithm of the rate constant for hydrolysis as a function of $pK_a$ can be roughly estimated as 0.6. Thus, RNA is expected to be more reactive than dimethyl phosphate by a factor of $10^{0.6 (15.5-12.5)} = 10^{1.8}$. The estimate for RNA pertains to direct attack by $OH^-$ on the phosphate, resulting in 3'-hydroxyl and 5'-phosphate termini. Cleavage of RNA by $OH^-$-catalyzed transphosphorylation, producing a 2',3'-cyclic phosphate, is a much more rapid (intramolecular) reaction but is not relevant to the reactions of the L-19 IVS RNA). On the basis of the data of FIG. 7D, the covalent enzyme-substrate complex undergoes hydrolysis at approximately the same rate as the equivalent bond in the circular IVS RNA. Thus, we estimate that the L-19 IVS RNA in its ribonuclease mode enhances the rate of hydrolysis of its substrate about $10^{10}$ times.

The RNA moiety of ribonuclease P, the enzyme responsible for cleaving transfer RNA (tRNA) precursors to generate the mature 5' end of the tRNA, is an example of an RNA enzyme molecule. (Guerrier-Takada, C., et al., (1983) Cell 35:849; Guerrier-Takada, C., et al. (1984) Science 223:285; Marsh, T. L., et al. in Sequence Specificity in Transcription and Translation, R. Calendar and L. Gold Eds., UCLA Symposium on Molecular and Cellular Biology (Plenum, New York, in press); Marsh, T. L., et al. (1985) Science 229:79). However, this enzyme catalyzes only a specific tRNA reaction without general RNA activity. The specificity is such that a variety of single base changes in the t-RNA portion of the pre-tRNA substrate prevent the enzyme from cleaving the substrate.

Dephosphorylation Activity

We have also found that the same enzyme has activity toward phosphate monoesters. The 3'-phosphate of $C_5p$ or $C_6p$ is transferred to the 3'-terminal guanosine of the enzyme. The pH dependence of the reaction (optimum at pH 5) indicates that the enzyme has activity toward the dianion and much greater activity toward the monoanion form of the 3'-phosphate of the substrate. Phosphorylation of the enzyme is reversible by $C_5$-OH and other oligo(pyrimidines) such as UCU-OH. Thus, the RNA enzyme acts as a phosphotransferase, transferring the 3'-terminal phosphate of $C_5p$ to UCU-OH with multiple turnover. At pH 4 and 5, the phosphoenzyme undergoes slow hydrolysis to yield inorganic phosphate. Thus, the enzyme has acid phosphatase activity. These are the two aspects of its dephosphorylase activity. The RNA enzyme dephosphorylates oligonucleotide substrates with high sequence specificity, which distinguishes it from known protein enzymes.

The L-19 IVS RNA has transphosphorylation activity toward 3'-phosphorylated oligo(C) substrates. The properties of the transphosphorylation reaction indicate that it is taking place in the same active site as the poly(C) polymerase and ribonuclease reactions (FIG. 15). The properties include the specificity of the reactions for oligo(C) substrates, the production of oligo(C) products with 3'-hydroxyl termini, and the formation of similar covalent enzyme-substrate complexes. The presumptive intermediate is a phosphoenzyme, E-p, in the case of the phosphotransferase reaction and a nucleotidyl enzyme, E-pC or E-(pC)$_n$, in the case of the poly(C) polymerase and ribonuclease reactions (Zaug & Cech, (1986) Science (Wash., D.C. 231:470-475). In both cases the presumptive covalent intermediate involves a phosphate ester linkage through the 3'-O of G414 of the L-19 IVS RNA (Zaug and Cech, unpublished results).

The transphosphorylation reaction is readily reversible. The phosphate can be transferred from the enzyme to an acceptor with a 3'-hydroxyl group, such as $C_5$ or UCU. With $C_5p$ and UCU as cosubstrates, the L-19 IVS RNA can catalyze the reaction $C_5p$ + UCU-OH → $C_5$-OH + UCUp. The proposed pathway is

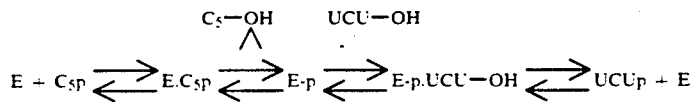

Thus, the L-19 IVS RNA has transphosphorylation activity resembling that of Escherichia coli alkaline phosphatase (Reid & Wilson, (1971) Enzymes (3rd Ed.) 4:373-415); Coleman & Gettins, (1983) Adv. Enzymol. Relat. Area Mol. Biol., 55:381), acid phosphatase, and a variety of other phosphotransferases that form covalent enzyme-substrate intermediates (Knowles, (1980) Ann. Rev. Biochem. 49:877). In addition, the L-19 IVS RNA phosphoenzyme can transfer its phosphate to water at pH 4 and 5, indicating it has acid phosphatase activity.

As the pH is lowered from 7.5 to 5.0, the rate of the transphosphorylation reaction increases substantially. In this same pH range, the 3'-phosphate of $C_5p$ is converted to a monoanion [$pK_a$ approximately 6.0, based on the value for cytidine 3'-phosphate from Ts'o [(1974) Basic Principles in Nucleic Acid Chemistry vol. 1, pp. 462 Academic, N.Y.]. Protonation of a phosphate monoester makes it possible for it to react like a diester (Benkovic & Schray, (1973) Enzymes (3rd Ed.) 8:235). Thus, it seems reasonable that an enzyme known to react with diesters could use the same mechanism to react with monoester monoanions. The acidic pH requirement for hydrolysis of the phosphoenzyme can be similarly explained if the reaction occurs by attack of water on the phosphate monoester monoanion. The pH independence of transphosphorylation between pH 7.5 and 9.0 strongly suggests that the monoester dianion is also reactive, albeit at a rate less than 5% that of the monoester monoanion. The reactivity of the monoester dianion is surprising and perhaps indicates that the enzyme provides electrophilic assistance to the departure of the leaving group with a proton or metal ion.

At alkaline pH the phosphodiester bond following G414 is labile in the circular IVS RNA (Zaug et al., 1984 Science (Wash., D.C. 224:574), in the pre-rRNA (Inoue et al., 1986, J. Mol. Biol. 189:143), and in E-pC (Zaug, A. J., and Cech, T., 1986, Science (Wash., D.C.) 231:470-475), whereas the phosphomonoester bond following G414 is stable in E-p. Specific hydrolysis of the phosphodiester bonds involves attack of hydroxide ion (Zaug, A. J. et al., (1985) Biochemistry 24:6211). It is not surprising that attack of hydroxide ion on the phosphate monoester dianion of E-p might be prohibited due to electrostatic repulsion (Kirby & Younas, (1970) J. Chem. Soc. B, 1165).

At pH 5 the phosphoenzyme undergoes very slow hydrolysis but readily transfers its phospho group to $C_5$-OH. The rate of the hydrolysis reaction is 2-3 orders of magnitude slower than that of the phospho transfer reaction, even though H2O is present at 55 M and the oligonucleotide at less than 1 uM. Thus, $C_5$-OH is a better acceptor than $H_2O$ by a factor exceeding $10^{10}$. [Such a large factor is not unusual for phosphotransferases; for example, Ray et al. (1976) Biochemistry 15:4006 report that phosphoglucomutase transfers a phosphate to the C-6 hydroxyl of glucose 1-phosphate at a rate $3 \times 10^{10}$ times greater than that of transfer to $H_2O$.] The difference in rate is much too large to be explained by the greater nucleophilicity of the 3'-hydroxyl of $C_5$-OH than $H_2O$, which could perhaps account for a factor of 10 (Lohrmann & Orgel (1978) Tetrahedron 34:853; Kirby & Varvoglis, (1967) J. Am. Chem. Soc. 89:415–423). Most of the difference in rate probably reflects the ability of the enzyme to utilize the binding energy from its interaction with non-reacting portions of $C_5$-OH (Jencks, W. P., 1975. Adv. Enzymol. Relat. Areas Md. Biol. 43:219). For example, specific binding interactions could precisely position the 3'-hydroxyl of $C_5$-OH for displacement of the phosphate from the enzyme, but would not be available to facilitate the addition of water. Furthermore, the catalytic apparatus may not be fully assembled until the acceptor oligonucleotide is in place and water is absent (Koshland, (1963) Cold Spring Harbor Symp. Quant. Biol. 28:473; Knowles, (1980) Ann. Rev. Biochem. 49:877).

Figure 15A:
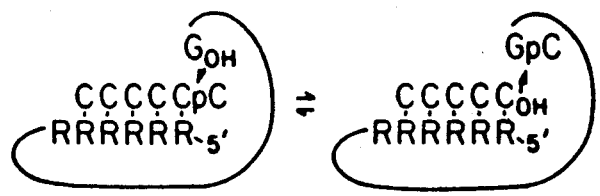
FIG. 15A and 15B show the single active site model for the activity of L-19 IVS RNA on phosphate diester and phosphate monoester substrates.
Figure 15B:
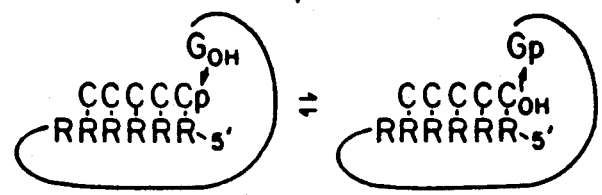

We are only beginning to understand how the L-19 IVS RNA catalyzes phospho transfer. The overall transfer reaction is undoubtedly facilitated by the formation of a covalent bond between the enzyme and the phosphate of the substrate. Such covalent catalysis is common in enzyme-catalyzed group transfer reactions (Jencks, (1969) Catalysis in Chemistry and Enzymology McGraw-Hill, New York; Walsh, (1979) Enzymatic Reaction Mechanisms W. H. Freeman, San Francisco). Binding sites within the IVS RNA for the oligo(pyrimidine) substrate (Zaug & Cech, (1986) Science (Wash., D.C. 231:470–475) and for the nucleophilic G residue at its own 3' end (N. K. Tanner and T. R. Cech, unpublished results) contribute to the catalysis of the transfer reactions. These binding interactions presumably place the 3'-hydroxyl group of G414 in an optimal orientation for nucleophilic attack on the terminal phosphate of $C_5p$ (FIG. 15B) or on an internal phosphate of $C_5$-OH (FIG. 15A). We suspect that catalysis might also involve a specific role for $Mg^{2+}$ [Steffens et al., (1973) J. Am. Chem. Soc. 95:936 and (1975) Biochemistry 14:2431; Anderson et al., (1977) J. Am. Chem. Soc. 99:2652; see also Zaug et al. (1985) Biochemistry 24:6211 and Guerrier-Takada et al. (1986) Biochemistry 25:1509] and general acid-base catalysis [see Cech and Bass (1986) Ann. Rev. Biochem. 55:599–629], but we have no direct evidence for such mechanisms. Applicants are not specifically bound by only those mechanisms discussed herein.

One unanswered question concerns the extremely low extent of nucleotidyl transfer with the $C_5p$ substrate at neutral pH. Since $C_5$-OH is readily attacked at the phosphate following the fourth C to produce E-pC, why is $C_5p$ not attacked at the equivalent phosphate to produce E-pCp? Perhaps the terminal phosphate of $C_5p$ is coordinated to Mg(II) or serves as a hydrogen bond acceptor, resulting in a preferred mode of binding different from that of $C_5$-OH.

Finding an enzyme that has both phosphodiesterase and phosphomonoesterase activity is unusual but not unprecedented. Exonuclease III (Richardson & Kornberg, (1964) J. Biol. Chem. 239:242-250), P1 nuclease, and mung bean nuclease (Shishido & Ando, 1982 in Nucleases (Linn, S. M. & Roberts, R. J. Eds) pp. 155-185, Cold Spring Harbor Laboratory, Cold Spring Harbor, N.Y.) all have 3'-phosphatase activity.

The L-19 IVS RNA is unique among known enzymes in its ability to remove 3'-phosphates from RNA with high substrate specificity. E. coli and mammalian alkaline phosphatases are nonspecific. These enzymes remove 5'-, 3'-, and 2'-phosphates from RNA with little regard for the base sequence of the molecule (Garen & Levinthal, (1960) Biochem. Biophys. Acta. 38:470; Harkness, (1968) Arch. Biochem. Biophys. 126:513). Polynucleotide kinase has 3'-phosphatase, 2'-phosphatase, and cyclic 2',3'-phosphatase activity (Cameron & Uhlenbeck, (1977) Biochemistry 16:5120; Weber, (1985) Ph.D. Thesis, University of Illinois). Substrates as diverse as $U_5p$, $A_6Cp$, and pCp are readily dephosphorylated, and where careful kinetic measurements have been made, the rates of dephosphorylation of different RNA substrates seldom vary by more than a factor of 2 (Weber, (1985) Supra). P1 nuclease and mung bean nuclease have limited preference for certain nucleoside 3'-monophosphates (Shishido & Ando, (1982) Supra). The L-19 IVS RNA, on the other hand, transfers the 3'-phosphate of RNA to a donor molecule with high substrate specificity; $C_5p$ and $C_6p$ are substrates, whereas pCp and $A_6pCp$ are not. This length and sequence specificity is explained by the requirement that the substance must bind to the enzyme by Watson-Crick base pairing to the guanosine-rich active site (FIG. 15). If this model is correct, it should be possible to alter the sequence specificity of the phosphotransferase by site-specific mutagenesis of the active site.

A series of sequence-specific 3'-phosphate dephosphorylating enzymes would provide a useful tool for RNA biochemistry and recombinant RNA manipulations. However, the RNA enzyme described here has cleavage-ligation activity as well as the dephosphorylation activity. Unless these activities can be separated, the usefulness of the enzyme as a reagent for dephosphorylation of RNA is limited.

Endoribonuclease or "RNA Restriction Endonuclease" Activity

We describe here a fifth enzymatic activity of the Tetrahymena ribozyme. It cleaves other RNA molecules at sequences that resemble the 5' splice site of the rRNA precursor. Cleavage is concomitant with addition of a free guanosine nucleotide to the 5' end of the downstream RNA fragment; thus, one product can be readily end-labeled during the reaction. The reaction is analogous to the first step of pre-rRNA self-splicing (FIG. 1). Cleavage does not require nucleotide $G^{414}$ of the ribozyme; thus, unlike the first four activities, it does not involve formation of a covalent enzyme-substrate intermediate. Thus there exists as a result of the work of the invention sequence-specific endoribonucleases, protein-free i.e. able to act in the absence of protein, and composed of RNA, which are enzymatically active on other RNA molecules. These RNA ribozymes act on exogenous RNA. Thus the enzyme or ribozyme is composed of RNA and the substrate is RNA (or mixed RNA-DNA polymers).

Figure 3A:
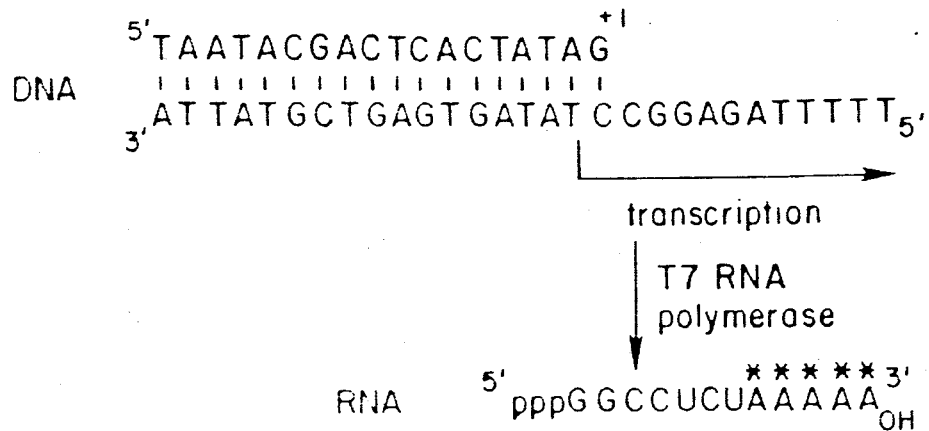
FIG. 3A, 3B, and 3C compare different substrate activity of three variant forms of L-19 IVS ribozyme in 2.5M urea.
Figure 3B:
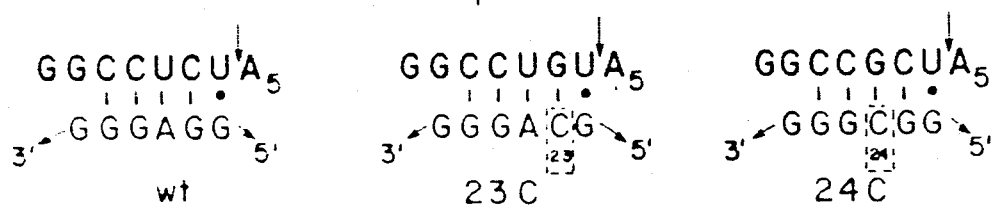
Figure 3C:
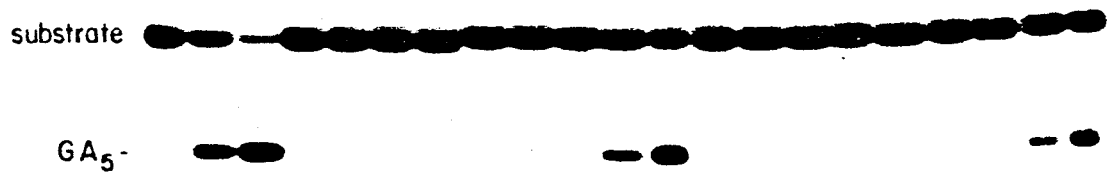

The ribozyme has high specificity for cleavage after the nucleotide sequence CUCU; under stringent conditions it can discriminate against sites that have a 3-out-of-4 match to this recognition sequence. For example, in a solution containing 2.5 M urea the ribozyme cleaves after CUCU while ignoring the related sequences CUGU and CGCU (FIG. 3c). The sequence specificity approaches that of the DNA restriction endonucleases (Nathans, D. and Smith, H. O. (1975) Annu. Rev. Biochem. 44:273-293). We further show that site-specific mutations in the active site of the IVS RNA, the so-called internal guide sequence (Davies, R. W., et al. (1982) Nature 300:719-724; Waring, R. B., et al. (1986) Nature 321:133-139) or 5' exon-binding site (inoue, T., et al. (1985) Cell 43:431-437; Garriga, G., et al. (1986) Nature 322:86-89; Been, M. D. and Cech, T. R., (1986) Cell 47, 207-216), alter the sequence specificity of the ribozyme in a predictable manner. In its endoribonuclease mode, the L-19 IVS RNA recognizes four or more nucleotides in choosing a reaction site. Protein ribonucleases that are active on single-stranded RNA substrates have specificity only at the mononucleotide level (for example, ribonuclease $T_1$ cleaves after guanosine). Thus the L-19 has more base-sequence specificity for single-stranded RNA than any known protein ribonuclease, and may approach the specificity of some of the DNA restriction endonucleases. An attractive feature of this new RNA enribonuclease is that its substrate specificity can be completely and predictably changed by altering the sequence of the internal binding site.

The endoribonuclease reaction is analogous to the first step of pre-rRNA self-splicing (FIG. 1). Both the enzymatic and the self-splicing reactions make use of the same two binding sites, an oligopyrimidine-binding site and a guanosine-binding site, to achieve specificity and to contribute to catalysis. The oligopyrimidine-binding site is also known as the 5' guide sequence (Waring, R. B., et al. (1986) Nature 321:133-139) or the 5' exon-binding site (Inoue, T., et al. (1985) Cell 43:431, Garriga, G., et al. (1986) Nature 322:86-89, Been, M. D. and Cech, T. R., *Cell* (1986) 47, 207-216). Its role in self-splicing has been conclusively demonstrated by the analysis of single-base mutations and second-site suppressor mutations (Waring, R. B., et al. (1986) Supra; Been, M. D. and Cech, T. R., (1986) Supra; Perea, J. and Jacq, C., (1985) EMBO, J. 4:3281). The role of these same nucleotides in the endoribonuclease reaction is demonstrated by the change in substrate specificity of the mutant enzymes (FIG. 3), the altered specificity being predictable by the rules of Watson-Crick base pairing. The guanosine-binding site involved in self-splicing has not been localized to a particular set of nucleotides, but its general features have been described (Bass, B. L. and Cech, T. R., (1984) Nature 308:820; (1986) Biochemistry 25:4473). The endoribonuclease activity appears to make use of the same guanosine-binding site by the following criteria: in both cases guanosine is as active as GTP, whereas UTP, CTP, ATP and dGTP have little if any activity. In addition, the $K_m$ of 44 uM for GTP shown is in reasonable agreement to the value of $32 \pm 8$ uM determined for self-splicing under somewhat different reaction conditions (Bass, B. L. and Cech, T. R., Biochemistry (1986) Supra).

Tee endoribonuclease activity of the L-19 IVS RNA does not require its 3'-terminal guanosine ($G^{414}$). In this respect it differs from the nucleotidyl transfer, phospho transfer and hydrolytic activities of the same enzyme. In those reactions $G^{414}$ participates in a covalent enzyme-substrate complex that appears to be an obligatory reaction intermediate (Zaug, A. J. and Cech, T. R. (1986) Science 231:470-475; Zaug, A. J. and Cech, T. R. (1986) Biochemistry 25:4478). Thus, the L-19 IVS RNA is not restricted to reaction mechanisms involving formation of a covalent enzyme-substrate intermediate. It an also catalyze bisubstrate reactions by a single-displacement mechanism. Ribonuclease P, an RNA enzyme that catalyzes cleavage by hydrolysis rather than by transesterification, also appears to act without formation of a covalent intermediate (Marsh, T. L., et al. (1985) Science 229:79-81; Guerrier-Takeda, C., et al. (1986) Biochemistry 25:1509).

The L-19 IVS RNA endoribonuclease activity reported here appears to require single-stranded RNA substrates. Based on work recently reported by Szostak ((1986) Nature 322:83-86), it seems possible that a smaller version of the Tetrahymena IVS RNA missing its 5' exon-binding site may have an endoribonuclease activity that requires a base-paired substrate. The substrate tested by Szostak ((1986) Nature Supra) was an RNA fragment containing the end of the 5' exon paired with the 5' exon-binding site. However, this RNA "substrate" also included a substantial portion of the IVS RNA, so it remains to be established whether the ribozyme has endoribonuclease activity with double-stranded RNA substrates in general.

Potential usefulness of sequence-specific RNA endoribonucleases. Sequence-specific endoribonucleases might have many of the same applications for the study of RNA that DNA restriction endonucleases have for the study of DNA (Nathans, D. and Smith, H.0., (1975) Ann. Rev. Biochem. 44:273). For example, the pattern of restriction fragments could be used to establish sequence relationships between two related RNAs, and large RNAs could be specifically cleaved to fragments of a size more useful for study. The 4-nucleotide specificity of the ribozyme is ideal for cleavage of RNAs of unknown sequence; an RNA of random sequence would have an average of 1 cleavage site every 256 bases. In addition, the automatic end-labelling of one fragment during ribozyme cleavage is a practical advantage.

Development of the ribozymes as useful tools for molecular biology has begun. The efficiency of cleavage of large RNA substrates needs to be increased so that complete digests rather than partial digests can be obtained. The effects of denaturants such as urea and formamide must be further explored; they appear to increase the sequence specificity of cleavage, and at the same time they should melt structure in the substrate to maximize the availability of target sequences. Finally, mutagenesis of the active site of the ribozyme by those skilled in the art can be accomplished to ascertain all possible permutations of the 256 possible tetranucleotide cleavage enzymes.

RNA sequence recognition. Protein ribonucleases can cleave RNA substrates with high specificity by recognizing a combination of RNA structure and sequence, with the emphasis on structure (e.g., RNase III (Robertson, H. D. (1982) Cell 30:669) and RNase M5

(Stahl, D. A., et al. (1980) Proc. Natl. Acad. Sci. USA 77:5644). Known proteins that cleave single-stranded RNA substrates, on the other hand, have specificity only at the mononucleotide or dinucleotide level (e.g., RNase T$_1$ cleaves after guanosines [Egami, F., et al. (1980) Molec Biol. Biochem. Biophys. 32:250-277]. Thus, the L-19 IVS RNA has considerably more base-sequence specificity for cleaving single-stranded RNA than any known protein ribonuclease.

Variant Ribozymes (or other versions of the ribozyme that retain activity)

Earlier work on sequence requirements for self-splicing (Price, J. V., et al. (1985) Nucleic Acid. Res. 13:1871) show that sequence requirements can be examined as shown therein by insertions and deletions to obtain other self-splicing IVS RNA's. In like manner, we could alter the L-19 IVS RNA to obtain an array of RNA sequence-specific endoribonuclease molecules. Thus three regions were found by Price et al. to be necessary for IVS self-splicing. Similar experiments would reveal necessary portions of L-19 IVS RNA for endoribonuclease activity. Burke, J. M., et al. (1986) Cell 45:167-176 show the role of conserved elements for the IVS self-splicing sequence; that work shows a further use of mutagenesis experiments to alter the highly conserved sequences to alter activity thereof. Just so, in like manner, the activity of the L-19 IVS RNA can be altered with accompanying alteration in activity to effect an array of endoribonucleases.

Cech, T. R., et al. have recently found a yet smaller piece of the L-19 IVS RNA which contains full enzymatic activity and comprises nucleotides 19-331 of the RNA. It is also found that the 21-331 piece is fully active. Plasmids have been constructed to produce the L-19 and L-21 IVS RNA strands directly. Here the promoter is moved to the 19 position or 21 position and the DNA coding for the restriction site is at the 331 position instead of the 414 site.

Been, M. D. and Cech, T. R. ((1986) Cell 47:207) show alteration in the specificity of the polymerase activity to effect polymerase activity with respect to oligo U using site-specific mutagenesis. Thus those skilled in the art can readily use the above to obtain other active L-19 IVS RNA enzymes.

Waring, R. B. and Davies, (1984) Gene 28:277 show a class of IVS RNA molecules with similar structure. This work is similar to that of Cech, T. R., et al. (1983) Proc. Natl. Acad. Sci. USA 80:3903 showing a class of fungal mitochondrial RNA IVS molecules. Some of these other IVS molecules have been found to be self-splicing. (Cech, T. R., et al. (1981) Cell 27:487; Kruger, K., et al. (1982) ibid. 31:147; Garriga, G., et al. (1984) ibid 39:631; Van der Horst, G., et al. (1985) ibid 40:759; Chu, F. K., et al. (1985) J. Biol. Chem. 260:10680; Peebles, C. L., et al. Cell in press; Van der Veen, R., et al., ibid. in press) Thus a series, or many series or class, or family of endoribonucleases from the same or other natural sources can be based on the work of the invention. Those skilled in the art will be able to search out other RNA enzymes from various natural sources.

The following RNA sequence elements can be considered to provide the minimum active site for ribozyme activity, based on (Cech, et al., PNAS (1983) and Waring & Davies Supra). Elements A and B interact with each other, as do 9L and 2. In many positions of the sequence, more than 1 base is allowed; the observed substitutions are shown by printing a letter directly below the base for which it can substitute. For example, at position 1 in sequence element A, the nucleotides A and U are observed, A being more common.

```
         A (also called P)                    B (also called Q)

optional
                                                        |
  1 2 3 4 5 6 7 8 9 10
5'-A UGCUGGAAA                            5'-AAUCA(C)GCAGG
  U    GAAAG U                               U  CUU  C    C
       G 9L (also called R)                   2 (also called S)

N = any base
5'-UCAGA GACUA NA                         AAGAU AUAGUC
   U    AC                                U G
        C
``` these pair namely GACUA on left and UAGUC on right as underlined:
compensatory base changes
are allowed - see Burke, et al.
(1986) Supra The linear sequence of non-template DNA coding for L IVS RNA is shown below. Coding for the L-19 IVS RNA "ribozyme" begins at the site indicated by the arrow and extends to the end (G$^{414}$). Of course, in RNA the T's are U's.

```
                  L-19
                  ┌─>       |           |              |
GAAATAGCAATATTTACCT TTGGAGGGAAAAGTTATCAGGCATGCACCTGGTA    53
                 / | \ \
                22 23 24 25

|           |           |              |           |
GCTAGTCTTTAAACCAATAGATTGCATCGGTTTAAAAGGCAAGACCGTCAAA    105

|           |           |              |           |
TTGCGGGAAAGGGGTCAACAGCCGTTCAGTACCAAGTCTCAGGGGAAACTTT    157

|           |           |              |           |
GAGATGGCCTTGCAAAGGGTATGGTAATAAGCTGACGGACATGGTCCTAACC    209

|           |           |              |           |
ACGCAGCCAAGTCCTAAGTCAACAGATCTTCTGTTGATATGGATGCAGTTCA    261
```

```
                |            |              |            |
CAGACTAAATGTCGGTCGGGGAAGA    T  GTATTCTTCTCATAAGATATAGT       310

|         |           |          |           |          |
CGGACCTCTCCTTAATGGGAGCTAGCGGATGAAGTGATGCAACACTGGAGCC            362

|             |            |            |          |
GCTGGGAACTAATTTGTATGCGAAAGTATATTGATTAGTTTTGGAGTACTCG            414
```

In the discussion of L-19 IVS RNA, the region of the active site sequence discussed with respect to activity and variants is:

```
U  U  G  G  A  G  G  G
20 21 22 23 24 25 26 27
```

The first ribonucleotide for the L-19 IVS RNA at the 5'OH end is the equivalent of the nucleotide 20 of the intact L IVS RNA. As regards positions 23, 24, 25 etc., these are positions 23, 24, 25 of the L VIS RNA (as if the first 19 positions were present).

Since dC$_5$ binds to the L-19 IVS RNA (see above), it is likely that the endoribonucleases will work on mixed polymers of RNA and DNA. For example, L-19 IVS RNA will bind the DNA portion while the RNA enzyme works on the RNA piece of the mixed polymer. Alteration of the binding site to bind the other nucleotides will result in an array of mixed polymer activity in a series of such endoribonucleases.

Abbreviations: IVS, intervening sequence; L-19 IVS RNA (read "L minus 19"), a 395-nucleotide linear RNA missing the first 19 nucleotides of the IVS; CHES,2-(cyclohexylamino)ethanesulfonic acid; EDTA, ethylenediaminetetraacetic acid; MES, 2-(N-Morpholino)-ethanesulfonic acid; Tris, tris(hydroxymethyl)aminomethane; p*, $^{32}$P within an oligonucleotide (for example, C$_5$p* is CpCpCpCpC[$^{32}$P]-pCp).

Enzyme Preparation. L-19 IVS RNA can be synthesized and purified as described by Zaug and Cech (1986) Science (Wash., D.C.) 231:470–475 (see FIG. 5 for detailed description). In brief, RNA was transcribed from pSPTT1A3 with bacteriophage SP6 RNA polymerase in vitro. (Alternatively RNA can be transcribed from pT$_7$-TT1A3 or from any of the plasmids in the pBG series with bacteriophage T$_7$ RNA polymerase in vitro). Transcripts were further incubated to promote self-splicing and cyclization of the IVS RNA. The RNA was subsequently incubated in MgCl$_2$ at pH 9.0 (site-specific hydrolysis conditions) to convert circular IVS RNA to L-19 IVS RNA. The L-19 IVS RNA was purified by polyacrylamide gel electrophoresis and Sephadex G-50 chromatography. Enzyme concentration was determined by spectrophotometry assuming a molar extinction coefficient at 260 nm of $3.26 \times 10^6$ M$^{-1}$cm$^{-1}$.

Active plasmids in use are as follows:
pSPTT1A3, pT$_7$-TT1A3, pBGST$_7$, pBG/-2G:23C, pBG/23C, pBG/-3G:24C, pBG/24C, pBG/-4G:25C, pBG/25C, and pBG/23A$_4$ and pT$_7$L-21. The PBG plasmid series is described in Been, M. and Cech, T. R. (1986) Cell 407:207. For example, the pBG/3G:24C and the pBG/24C plasmids produce the L-19 IVS RNA 24C variant which cleaves RNA after the CGCU 4 base sequence. These plasmids are on deposit and available at the Department of Chemistry and Biochemistry, University of Colorado, Boulder, Colo. 80309-0215. Examples of these including pBG ST$_7$ (ATCC 40288), pT$_7$-TT1A3 (ATCC 40290) and pBG/-3G:24C (ATCC 40289) have been deposited with the American Type Culture Collection (ATCC) 12301 Parklawn Drive, Rockville Md. 20301 on Nov. 25, 1986. The plasmid pT$_7$L-21 makes the L-21 IVS RNA wherein the first 21 bases are deleted. This plasmid (ATCC 40291) was also placed on deposit at the ATCC on Dec. 2, 1986.

Preparation of Substrates. C$_5$p*Cp and A$_6$p*Cp were prepared from C$_5$-OH and A$_6$-OH, respectively, with T$_4$ RNA ligase (New England Nuclear), p*Cp, and ATP. Products were purified by 20% polyacrylamide-7 M urea gel electrophoresis and Sephadex G-25 chromatography. C$_5$p* was prepared from C$_5$p*Cp by treatment with calf intestinal phosphatase and beta-elimination (Winter & Brownlee, 1978 Nucleic Acid. Res. 5:3129). Unlabeled C$_5$p was prepared in a similar manner with unlabeled pCp as donor in the ligase reaction. Concentration was determined by spectrophotometry using a molar extinction coefficient at 270 nm of $30 \times 10^3$ M$^{-1}$cm$^{-1}$.

Preparation of E-p*. Unlabeled L-19 IVS RNA (16 pmol) was incubated with 5.2 pmol of C$_5$p* in 50 mM NaOAc, pH 5.0, and 20 mM MgCl$_2$ at 42° C. for 10 min. The reaction was stopped by the addition of EDTA to 40 mM. The E-p* was purified from unreacted C$_5$p* by column chromatography on Sephadex G-100-120, which was equilibrated in 0.01 M Tris-HCl, pH 7.5, 0.25 M NaCl, and 0.001 M EDTA. The fractions that contained E-p* complex were pooled and precipitated with 3 volumes of ethanol. The dried precipitate was then dissolved in H$_2$O.

Standard Nucleotidyl Transferase Reaction Conditions

The oligoribonucleotide substrate (for example 10-100 uM pC$_5$) is incubated with ribozyme (for example 0.1-2.0 uM L-19 IVS RNA) at 42° C. in 20 mM Mgcl$_2$ and 50 mM Tris, pH 7.5 for 1 hour.

Standard Transphosphorylase Conditions

The 3'-phosphorylated RNA substrate (for example 2.5 uM C$_5$p) is incubated with ribozyme (for example 0.1 uM L-19 IVS RNA) and an acceptor oligonucleotide (for example, 200 uM UpCpU) at 42° C. in 20 mM MgCl$_2$ and 50 mM MES, pH 6.0 for 3 hours.

Standard Acid Phosphotase Conditions

The 3' phosphorylated RNA substrate (for example 2.5 uM C$_5$p) incubated in equimolar concentration of ribozyme (for example 2.5 uM L-19 IVS RNA) at 42° C. in 20 mM MgCl$_2$ and 50 mm NaC$_2$H$_3$O$_2$ (Na acetate), pH 5.0 for 24 hours.

Standard Endoribonuclease Reactions

Substrate RNA is pretreated with glyoxal according to the procedure of Carmichael and McMaster (1980) Meth in Enzymol. 65:380-391 and then ethanol precipitated and the precipitate pelleted by centrifugation in an eppendorf centrifuge. The pellet is dried and the RNA re-suspended in water. The glyoxylated substrate RNA (0.2 uM) is incubated with ribozyme (for example L-19 IVS-beta RNA, 0.2 uM) at 50° C. in 10 mM $MgCl_2$, 10 mM NaCl, 50 mM Tris-HCl pH 7.5, 0.5 mM GTP, 2.5M Urea for 1 hour.

Stopping Reactions and Analyzing Products

In all cases reactions are stopped by the addition of EDTA to a final concentration of 25 mM. Products can be analyzed by electrophoresis in a 20% polyacrylamide, 7.0 M Urea gel (standard sequencing gel). If $^{32}$P-labelled RNA substrates are used, products can be localized by autoradiography.

The following Examples and the standard conditions above serve to illustrate, but not to limit the invention.

EXAMPLE I

Sequence-specific cleavage of large RNAs

The L-19 IVS RNA enzyme was prepared by incubation of pre-rRNA under conditions that promote self-splicing, cyclization, and site-specific hydrolysis. (Zaug, A. J., et al. (1984) Science 224:574; Zaug, A. J., et al. (1986) Science 231:470). The 3'-terminal guanosine ($G^{414}$) was then removed from the L-19 IVS RNA by periodate oxidation followed by beta-elimination (Winter, G., et al. (1978) Nucleic Acids Res. 5:3129–3139). As expected, the resulting ribozyme (L-19 IVS-beta) has greatly reduced activity as a nucleotidyl-transferase, assayed using [$^{32}$P]-p(C)$_5$ as a substrate. When GTP was added, however, the ribozyme was able to cleave p(C)$_5$ as well as large RNA molecules. For example, the 504 nt pAK105 transcript (Mount, S. M., et al. (1983) Cell 33:509-518), a fragment of mouse beta-globin pre-mRNA containing the first intron, was cleaved to give major fragments of 148, 360 and 464 nt, as well as some minor fragments (FIG. 2a). As shown below, the 360 and 148 nt fragments can be explained as the 5' and 3' products of cleavage at position 360. The 464 nt fragment is the 3' product of cleavage at position 44, the 5' 44 nt fragment being to small to be observed. The absence of a major amount of a 316 nt RNA, the expected product of cleavage at both position 44 and 360, is indicative of partial digestion with few molecules cleaved more than once.

Cleavage required magnesium ion (optimum at 10-20 mM $MgCl_2$) and was essentially independent of monovalent cation in the range 0-200 mM NaCl. The pH optimum was in the range of 7.5-8.0, and the temperature optimum was approximately 50° C. Although the beta-eliminated L-19 IVS RNA was competent to catalyze the cleavage reaction, removal of $G^{414}$ from the ribozyme was not required for cleavage activity. The enzyme worked at the same rate whether or not $G^{414}$ had been removed. We explain the activity of the intact L-19 IVS RNA by the postulate that, at saturating concentrations of GTP, the attack by GTP on the substrate competes very effectively with attack by $G^{414}$.

We note the IVS RNA and L-19 IVS RNA are protein-free. The L-19 IVS RNA is therefore a protein-free RNA enzyme (or ribozyme). L-19 IVS RNA and the like also function as enzymes in the absence of proteins. This applies to exogenous as well as endogenous protein. This is evidenced by retention of activity when subjected to protease activity, boiling or sodium dodecyl sulfate. Any RNA polymerase protein from the transcription system used to produce IVS RNA is removed by phenol extraction. The ability to make the IVS RNA in a totally defined system in vitro and remove the RNA polymerase by phenol extraction is further evidence of the protein-free nature of the reaction.

EXAMPLE II

Labelled cleavage products

When [alpha-$^{32}$P]GTP was included in the reaction of pAK105 RNA as in Example I above, the 148 and 464 nt cleavage products were labeled (FIG. 2b). Direct sequencing of these labeled RNA fragments (e.g., FIG. 2c) showed that cleavage and GTP-addition occur at nucleotides 44 and 360 in the sequence, such that the downstream cleavage products are 5'-GTP labeled. The bonds formed by GTP addition are sensitive to RNase $T_1$, confirming that the GTP was covalently added through its 3'-O by a normal 3'-5' phosphodiester bond. Reaction of the 841 nt $pT_{7-1}$ (Xmn 1) RNA (essentially $pBR^{322}$ sequences) produced 4 major labeled fragments. These were sequenced in the same manner. $pT_{7-1}$ RNA with an additional 122 nt at its 3' end, produced by transcription of $pT_{7-1}$ DNA that had been cleaved at the Sca I site, showed the expected increase in molecular weight of the labeled products. In all of the reactions, including those in which substrate RNA was omitted, the L-19 IVS RNA became labeled, perhaps by the guanosine-exchange reaction proposed elsewhere (Zaug, A. J., et al. (1985) Science 229:1060–1064; Price, J. V., et al. (1987) J. Mol. Biol. in press). The sites of self-labeling were heterogeneous.

EXAMPLE III

Specificity Assessment

The sequence near the 5' end of each end-labeled product (See Example II above) was compared to the known sequence of the RNA to identify the nucleotides preceding the site of cleavage. The results are summarized in Table 1. Both the major and the minor cleavage sites are preceded by four pyrimidines, the consensus sequence being CUCU. This is exactly the tetranucleotide sequence expected to be an optimal target for the ribozyme. The importance of nucleotides at positions -5 and -6 relative to the cleavage site is not yet clear, although the absence of G residues may be significant. There is no apparent sequence preference downstream from the cleavage site, with all four nucleotides represented at position +1.

In assessing specificity, it is also necessary to consider which potential sites in the RNA were not cleaved by the ribozyme. For the pAK105 RNA, there was only one CUCU site at which cleavage was not observed. (Cleavage at this site would have produced a labeled 378 nt RNA.) On the other hand, a great many sites that match CUCU in 3 out of 4 positions were not cleaved. These include 17 CUMU sequences (where M≠C) and 7 CNCU sequences (where N≠U). In $pT_{7-1}$ RNA, cleavage was observed at both the CUCU sequences in the RNA, but at only one of the 15 UUUU sequences present. Thus, the ribozyme has a strong preference for cleavage after the tetranucleotide CUCU.

EXAMPLE IV

Cleavage within regions of base-paired RNA secondary structure

M1 RNA, the RNA subunit of *E. coli* RNase P (Reed, R. E., et al. (1982) Cell 30:627-636), was not cleaved by L-19 IVS RNA-beta under standard reaction conditions (FIG. 2b). M1 RNA contains the sequence UCCUCU, which should be an excellent target site. However, this sequence is involved in a stable hairpin stem (Guerrier-Takada, C., et al. (1984) Biochemistry 23:6327-6334; Pace, N. R., et al. (1985) Orig. of Life 16:97-116), which presumably makes it unavailable as a substrate. We have found that denaturation of M1 RNA with glyoxal allowed efficient cleavage of this site by L-19 IVS RNA, in support of the interpretation that RNA secondary structure can inhibit cleavage. The glyoxal procedure used for denaturation is according to Carmichael, G. G., et al. (1980) Meth. in Enzymol. 65:380-391.

EXAMPLE V

Active-site mutations alter substrate specificity

The substrate specificity was next studied in a defined system where we could be certain that secondary structure in the substrate RNA was not affecting the cleavage reaction. Oligoribonucleotide substrates were synthesized by the phage T7 RNA polymerase transcription method developed by Uhlenbeck and co-workers (Lowary, P., et al. (1986) NATO ASI Series, vol. 110, 69-76) (FIG. 3a). One substrate contained a perfect match to the tetranucleotide consensus sequence. Two other substrates had single-base changes giving a 3-out-of-4 match to the consensus.

These substrates were tested with the wild-type L-19 IVS RNA and with two altered ribozymes (Been, M. D. and Cech, T. R., (1986) Cell 47,207-216). The two variants have single-base changes in the 5' exon-binding site that alter the sequence specificity of the first step in pre-rRNA self-splicing (Been, M. D., et al. Supra). The 23C variant (G converted to C at position 23 of the L-19 IV RNA) is expected to recognize CUGU substrates, and the 24C (A converted to C at position 24) variant should recognize CGCU (FIG. 3b). In the course of these studies, we found that the inclusion of 2.5M urea or 15% formamide in the reactions greatly increased the specificity, allowing each ribozyme to differentiate substrates with a single base change in the recognition sequence. Our operating model is that these denaturants destabilized the base-pairing between the substrate and the active site nucleotides of the ribozyme, thereby discriminating against mismatched complexes. The results of treatment of the 3 substrates with each of the 3 ribozymes in the presence of 2.5 M urea are shown in FIG. 3c. Each substrate is cleaved exclusively by the ribozyme that is capable of making a perfectly base-paired enzyme-substrate complex (FIG. 3b). Thus it is contemplated the active site can be manipulated to recognize any base sequence so far that is XYZU, where X, Y and Z can be any of the four bases A,U,C,G and the nucleotides in the four base sequence can be the same or different.

When variant ribozymes were incubated with the 504 nt pAK105 RNA, each ribozyme gave a different pattern of cleavage products. One major cleavage site has been mapped for three variant ribozymes, including a 25C variant (G converted to C at position 25). The sites cleaved by the 23C, 24C and 25C ribozymes are preceded by CCCUGU, UCUGCU, and CUGUCU, respectively; the underlining indicates the base that would form a G·C base pair with the mutated nucleotide in the variant ribozyme. Each of these sequences can form 6 continuous base-pairs with the active site nucleotides of the variant ribozyme. While more cleavage sites must be sequenced before specificity can be properly assessed, these initial results are promising.

EXAMPLE VI

Cleavage is catalytic

The time course of cleavage of the oligonucleotide substrate GGCCCUCU*AAAAA (where the asterisk designates the cleavage site) by the wild-type ribozyme is shown in FIG. 4a. The reaction of 2.5 uM substrate with 0.2 uM ribozyme is 66% complete in 90 minutes. Thus, it is readily apparent that the ribozyme is acting catalytically.

The reaction rate was determined at a series of substrate concentrations. The kinetics are adequately described by the Michaelis-Menten rate law. The dependence of the rate on GTP concentration is shown in the form of a Lineweaver-Burk plot in FIG. 4b. The $K_m$ for GTP is 44 uM. The dependence of the rate on RNA substance concentration at saturating GTP concentration is shown in FIG. 4C. The $K_m$ for this oligoribonucleotide substrate is 0.8 uM, and $k_{cat}$ is 0.13 min$^{-1}$. Thus under $V_{max}$ conditions the enzyme turns over about 8 times per hour.

EXAMPLE VII

In the absence of urea and formamide, single-base changes in the substrate RNA 3 nucleotides preceding the cleavage site of the RNA ribozyme, giving a mismatched substrate-ribozyme complex, enhance the rate of endoribonuclease cleavage. Mismatched substrates show up to a 100-fold increase in $k_{cat}$ and, in some cases, in $k_{cat}/K_m$. A mismatch introduced by changing a nucleotide in the active site of the ribozyme has a similar effect. Addition of 2.5 M urea or 3.8 M formamide or decreasing the divalent metal ion concentration from 10 to 2 mM reverses the substrate specificity, allowing the ribozyme to discriminate against the mismatched substrate. The effect of urea is to decrease $k_{cat}/K_m$ for cleavage of the mismatched substrate; $K_m$ is not significantly affected at 0-2.5 M urea. Thus, progressive destabilization of ribozyme-substrate pairing by mismatches or by addition of a denaturant such as urea first increases the rate of cleavage to an optimum value and then decreases the rate.

The ribozyme and variants with altered sequence specificity provide a set of sequence-specific endoribonucleases that may be useful reagents for a variety of studies of the molecular biology of RNA.

Materials. Unlabeled nucleoside triphosphates were purchased from P-L Biochemicals, labeled nucleoside triphosphates from New England Nuclear, calf intestinal phosphatase from New England Nuclear, T$_4$ polynucleotide kinase from United States Biochemicals, and restriction endonucleases from New England Biolabs. T$_7$ RNA polymerase was isolated from *Escherichia coli* strain BL21, containing the plasmid pAR1219 (Davanloo et al., (1984) Proc. Natl. Acad. Sci. USA 81:2035-2039).

L - 21 Sca I RNA Preparation. Plasmid pT$_7$L-21 was cut with ScaI restriction endonuclease, extracted with phenol and chloroform, ethanol precipitated, and then resuspended in H₂O to 1 ug/uL. Transcription was done in 2 mL of 40 mM Tris-HCl, pH 7.5, 12 mM MgCl₂, 10 mM DTT, 4 mM spermidine, 1 mM each nucleoside triphosphate, 10 ug/mL linearized plasmid, and 200 units of T7 RNA polymerase/ug of DNA. Incubation was for 1 h at 37° C. Products were ethanol precipitated and purified by electrophoresis in a 4% polyacrylamide/8 M urea gel. The L - 21 ScaI RNA was visualized by UV shadowing, excised, and eluted overnight at 4° C. in 250 mM NaCl, 10 mM Tris-HCl, pH 7.5, and 1 mM EDTA. The gel was removed by centrifugation. The RNA was ethanol precipitated and chromatographed on a Sephadex G-50 column equilibrated in 250 mM NaCl, 10 mM Tris-HCl, pH 7.5, and 1 mM EDTA. Fractions that contained RNA were pooled and ethanol precipitated. The precipitate was washed with 70% ethanol, dried, and resuspended in H₂O. L - 21 ScaI RNA concentration was determined by spectrophotometry. The extinction coefficient, ($E_{260}$ nm = $3.2 \times 10^6$ M$^{-1}$ cm$^{-1}$, was determined by taking a sample of L - 21 ScaI RNA ($A_{260}$ nm = 0.534), hydrolyzing to completion with a mixture of ribonuclease $T_1$, $T_2$, and A, remeasuring the absorbance ($A_{260}$ nm = 0.753), and multiplying the ratio of these absorbances by the extinction coefficient calculated for a mixture of free nucleotides in the proportion that they occur in the L - 21 ScaI RNA.

Synthesis of Oligoribonucleotide Substrates. Oligoribonucleotides were produced by transcription of synthetic DNA templates as described by Lowary et al. NATO ASI ser, ser A 110:69-76 (1986) and Milligan et al. (1987) Nucleic Acids Res. 15:8783. Transcription solutions (2 mL) contained 12 mM MgCl₂, 40 mM Tris-HCl, pH 7.5, 10 mM DTT, 4mM spermidine, 2 mM each nucleoside triphosphate, 1.5 uM promoter top strand DNA, 1.5 uM promoter template bottom strand DNA, and 100,000 units/mL T7 RNA polymerase. (The top and bottom strand deoxyoligonucleotides were synthesized on an Applied Biosystems 380B DNA synthesizer, deprotected, ethanol precipitated, and used without further purification). Incubations were done for 2 h at 37° C. Products were ethanol precipitated and purified by electrophoresis on 20% polyacrylamide/7 M urea gels. Purification proceeded as described above for L - 21 ScaI RNA, except that chromatography was on a Sephadex G-25 column.

Labeling of Oligoribonucleotides. Purified oligonucleotide (100 pmol) was incubated with 8 units of calf intestinal phosphatase in 100 uL of H₂O at 37° C. for 1 h. The solution was extracted with phenol and ether and evaporated to dryness. 5' end labeling was accomplished using T₄ polynucleotide kinase and [γ-³²P]ATP. Labeled RNA was purified by electrophoresis on a 20% polyacrylamide/7 M urea sequencing gel, visualized by autoradiography, excised, and eluted as described above.

Initial Velocity Determination. Reactions (30 uL) contained 0.01 uM L - 21 ScaI RNA, 500 uM GTP, 10 mM MgCl₂, 50 mM Tris-HCl, pH 7.5, and a mixture of unlabeled and 5' end-labeled substrate varying in concentration from 0.1 to 4.0 uM. Reactions were initiated by addition of the MgCl₂ and proceeded at 50° C. Portions (3 uL) were removed at times ranging from 1 to 120 min and added to a stop mixture that contained 100 mM EDTA. Samples were subjected to electrophoresis on a 20% polyacrylamide/7 M urea gel. Bands were visualized by autoradiography, cut from the gel, and counted in toluene-based fluor in a Beckman LS7000 scintillation counter. Initial velocities were determined as described by Bass and Cech (1984) Nature (London) 308:820.

Increased Specificity of Cleavage in the Presence of Urea and Formamide. An oligoribonucleotide substrate containing the recognition sequence CUCU was incubated either with the wild-type L - 19 IVS$_{beta}$ RNA or with the 24C variant ribozyme. As shown in FIG. 17a, both ribozymes cleaved the substrate at the same site. It had previously been shown that the cleavage site immediately follows the recognition sequence (Zaug et al., (1986) Nature (London) 324:429). In the absence of urea, the rate of cleavage was actually faster with the variant ribozyme than with the wild-type ribozyme, despite the fact that the variant cannot form a matched ribozyme-substrate complex. As the concentration of urea was increased, the rate of cleavage by the 24C variant ribozyme steadily decreased, while the rate of cleavage by the wild-type ribozyme stayed approximately constant in the range 0-2 M urea. Thus, around 2 M urea there was optimal discrimination between the substrates that form matched and mismatched ribozyme-substrate complexes (FIGS. 17 and 18).

Figure 17B:
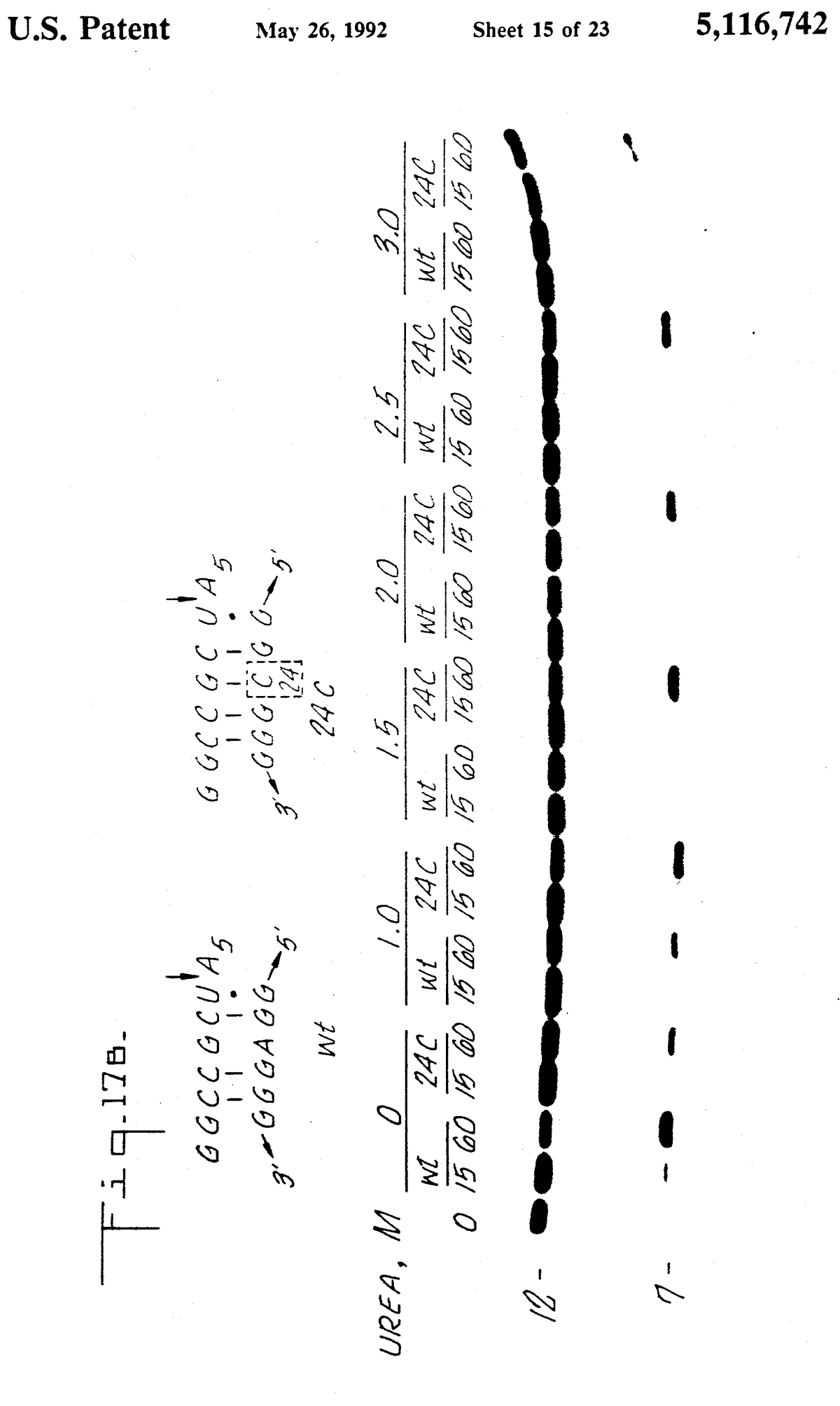

An oligoribonucleotide substrate containing a CGCU sequence was similarly incubated with the two ribozymes. In this case the wild-type ribozyme was expected to give a mismatched ribozyme-substrate complex, while the 24C variant ribozyme matched the substrate perfectly. As shown in FIG. 17b, the rate of cleavage by the wild-type ribozyme decreased steadily with increasing urea concentration, while the rate of cleavage by the 24C variant actually increased and then remained constant up to 3 M urea, the highest concentration tested. Good discrimination between the matched and mismatched complexes was obtained in the broad range of 1.5-3.0 M urea.

Figure 17C:
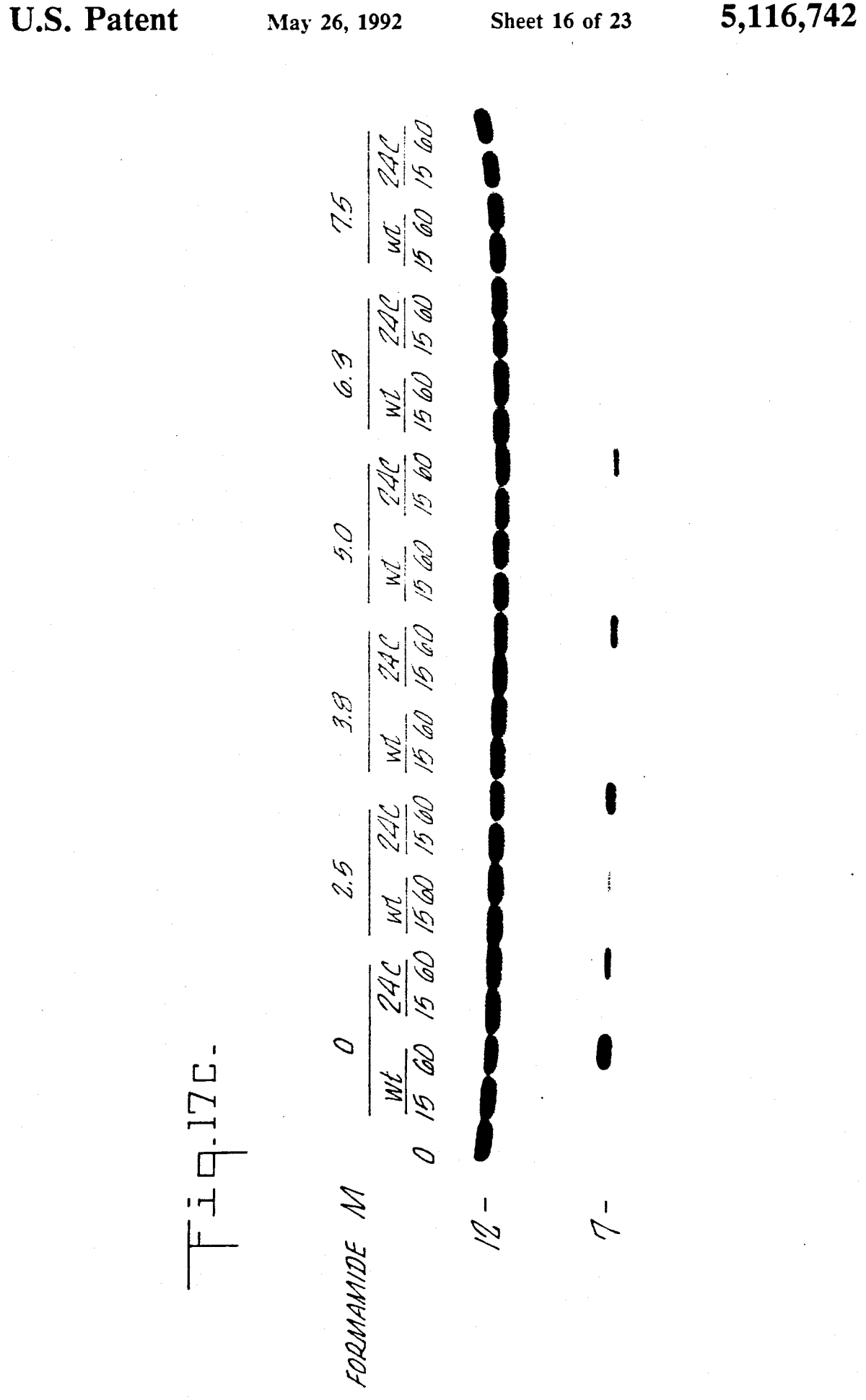

A different RNA denaturant, formamide, also affected the specificity of the cleavage of the CGCU-containing substrate. As shown in FIG. 17c, the rate of cleavage by the wild-type ribozyme decreased with increasing formamide concentration, while the rate of cleavage by the 24C variant increased and then decreased at concentrations > 5M formamide. Optimum cleavage by the 24 C variant was achieved at 2-4M. Thus, the dependence of cleavage rate on denaturant concentration for both enzymes was similar with the two denaturants, 2.5M formamide having an effect equivalent to that of 1.5 M urea. The releative effects of formamide and urea are consistent with their acting to destabilize an RNA duplex. Studies with DNA have shown that 2.5 M formamide (40% v/v) is approximately as destabilizing as 2.1 M urea (Lerman et al., (1984) Annu. Rev. Biophy. Bioeng. 13:399); it is expected that the effect would be somewhat different for RNA-RNA duplexes [see discussion by Casey and Davidson (1977) Nucleic Acids. Res. 4:1539].

Synthesis of Ribozyme by Direct Transcription. The L - 19 IVS$_{beta}$ RNA used as the ribozyme in the experiments described above was made by in vitro transcription of pre-rRNA followed by a cascade of self-reactions mediated by the folded structure of the IVS: splicing, cyclization of the excised IVS, and site-specific hydrolysis at the cyclization junction (Zaug et al., (1984) Science 224:574). The L - 19 IVS RNA was then purified from the ligated exons and other reaction products, and its 3'-terminal guanosine was removed by periodate oxidation and beta-elimination to give L - 19 IVS$_{beta}$ RNA. To facilitate the synthesis of large amounts of ribozyme, a plasmid was constructed (FIG. 19) such that the initial product of transcription would be the active ribozyme itself, with no further self-processing required. A phage T7 promoter was juxtaposed to the DNA encoding nucleotide 22 of the IVS, so that the active-site GGAGGG sequence comprises nucleotides 1-6 of the transcript. Truncation of the plasmid with ScaI restriction endonuclease and transcription with purified phage T7 RNA polymerase (Davanloo et al., 1984 Supra) gives the L - 21 ScaI RNA.

Transcription of linear DNA templates by T7 RNA polymerase frequently produces RNA with one or more extra nucleotides at its 3' end beyond those specified by the template (Lowary et al., 1986; Milligan et al., 1987). The 3' end of the L - 21 ScaI RNA was analyzed by 3' end labeling with [$^{32}$P]pCp and RNA ligase, followed by complete digestion with RNase T2 and analysis of the nucleoside 3'-phosphate products by thin-layer chromatography. THe label was distributed as follows: 47% C, 32% U, 9% G, 12% A. (The last templated nucleotide was predicted to be a U). Thus, while the L - 21 ScaI RNA appears to be homogeneous when analyzed by electrophoresis in a 4% polyacrylamide gel, it has a heterogeneous 3' end.

The L - 21 ScaI RNA differs from the L - 19 IVS$_{beta}$ RNA by being 2 nucleotides shorter at its 5' end and approximately 3-4 nucleotides shorter at its 3' end. The activity of these two ribozymes is similar. For example, with a GGCCCUCUA$_5$ substrate under standard reaction conditions, the L - 21 ScaI RNA has $k_{cat}/K_m = 0.2$ min$^{-1}$ uM$^{-1}$ (Table 3) compared to values of $k_{cat}/K_m$ in the range of 0.05-0.16 min$^{-1}$ uM$^{-1}$ for the L - 19 IVS$_{beta}$ RNA (FIG. 4b,c of Zaug et al. (1986).]

Kinetic Analysis of Oligoribonucleotide Cleavage in the Absence of Urea. We have shown that, in the absence of urea, certain substrates are cleaved more rapidly by a ribozyme that forms a mismatched ribozyme-substrate complex than by a ribozyme that has perfect complementarity to the substrate (FIG. 17). We now show that the same sort of enhanced cleavage is observed when the mismatch is introduced by varying the sequence of the substrates while leaving the ribozyme constant.

We prepared the series of substrates *pGGCCCNCU↓A$_5$, where *p indicates the radiolabeled phosphate and N=C,A,G, and U, and incubated them with L - 21 ScaI RNA in the presence of 0.5 mM GTP. For N=A,G, and U, the only labeled product was an octanucleotide, the size expected for cleavage at the vertical arrow. For N=C, initial cleavage occurred at the same site; later in the reaction, the octanucleotide was further cleaved to a heptanucleotide, indicating secondary cleavage following the five C residues. The $k_{cat}$ for cleavage varied over a 100-fold range as N was changed: C>A≈G>>U (Table 3). The $K_m$ values showed much less variability. The matched substrate (N=U) and the other pyrimidine-containing substrate (N=C) have slightly lower $K_m$'s than the two substrates that would be expected to form purine-purine mismatches with the ribozyme. We also studied the series of substrates *pGGCUCNCL↓A$_5$, where N=C,A,G, and U. In all cases, cleavage occurred predominantly at the position indicated by the arrow. The $k_{cat}$ for cleavage varied over a 50-fold range as N was changed; the order C>A≈G>U was the same as with the *pGGCCCNCUA$_5$ series (Table 3). $K_m$ varied in the order C>A>G>>U, similar to $k_{cat}$.

It is useful to compare each substrate that has a C at position −5 (first four rows of Table 3) with the corresponding substrate that has a U at position −5 (last four rows of Table 3). THe $k_{cat}$ of each GGCCCNCUA$_5$ substrate is always similar to that of the corresponding GGCUCNCUA$_5$ substrate; most of the comparisons show less than a 2-fold difference, which is not considered significant. The $K_m$'s of the two substrates with N=U (i.e., a matched nucleotide in position −3) were not significantly different. In each case where there was a mismatched nucleotide at position-3 (N=C, A, or G), the $K_m$ was significantly lower with a C at position −5 than with a U at position −5. According to our model (FIG. 1), a C at position −5 would form a G-C base pair with the ribozyme, while a U would form a G-U wobble base pair.

Kinetic Analysis of Cleavage in the Presence of Urea. The effect of urea on cleavage was studied in some detail with *pGGCCCGCUA$_5$, a substrate whose cleavage by wild-type ribozyme was expected to be strongly inhibited by higher concentrations of urea (FIG. 17b). As shown in FIG. 20 and Table 4, low concentrations of urea slightly enhanced the cleavage of L - 21 ScaI RNA, while 2.0 and 2.5 M urea inhibited cleavage as expected. The effects were almost entirely due to changes in $k_{cat}$, $K_m$ staying constant at 0.5±0.2 uM. This is not the result expected if $K_m$ simply represented the dissociation constant of the ribozyme-substrate complex; in that case, increasing the concentration of urea would be expected to increase the $K_m$.

The effect of urea of the initial velocity of six different oligoribonucleotide substrates was determined (FIG. 21). A relatively high substrate concentration was chosen so that the velocity measurements would approximate V$_{max}$. (The substrate concentration was below $K_m$ for two of the substrates,

so cleavage rates for these substrates underestimate V$_{max}$.) The substrates can be divided into three groups on the basis of the response of their cleavage rate to urea. The substrates

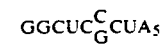

(mismatched at position −3 and wobble base paired at position −5) showed steady reduction in cleavage with increasing urea concentration. The substrates

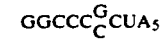

(mismatched at position −3 and G-C base paired at position −5) showed an increased rate of cleavage at low urea concentrations followed by a decrease at 1 M urea. The substrates

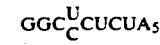

(matched at position −3 and either G-U or G-C base paired at position −5) showed increased rate of cleavage with increasing urea concentration over the entire range tested. The best matched of these two substrates, GGCCCUCUA$_5$, showed little change in cleavage rate between 0 and 1.5 M urea, consistent with the previous results with the same substrate and the L - 19 IVS$_{beta}$ ribozyme (FIG. 18, closed circles).

Cleavage in Ribozyme Excess. To test whether the enhanced cleavage of mismatched substrates persisted under single-turnover conditons, GGCCCGCUA$_5$ and GGCCCUCUA$_5$ (0.05 uM) were treated with a 20-fold molar excess of L - 21 ScaI RNA (1.00 uM) in the absence of urea. Cleavage of the mismatched substrate was more rapid than cleavage of the matched substrate. Although cleavage of the mismatched substrate occurred too quickly to obtain a reliable rate, the rate was at least 8 times faster than that of the matched substrate. A 23-fold rate difference was predicted from the k$_{cat}$ and K$_m$ values of the Table 3, using the equation v$_o$=k$_{cat}$[E$_o$][S$_o$]/(K$_m$+[E$_o$]) for reaction in enzyme excess. Thus, the results of this experiment gave no indication of a previously unrecognized rate-limiting step involving product dissociation. The results do not, however, rule out the possibility that some of the rate difference between matched and mismatched substrates might be due to a differential rate of product release.

Cleavage as a Function of Divalent Cation Concentration. Urea and formamide, both of which destabilize RNA duplexes, allow the ribozyme to discriminate against mismatched substrates. To test the generality of this correlatron, we examined cleavage of matched (GGCCCUCUA$_5$) and mismatched (GGCCCGCUA$_5$) substrates by the L - 21 ScaI RNA as a function of decreasing Mg$^{2+}$ concentration. Experiments were done in the presence of urea. The initial rate of cleavage of the mismatched substrate exceeded that of the matched substrate at 10 and 5 mM MgCl$_2$, but specificity was reversed at 2 mM MgCl$_2$. Neither substrate was cleaved at 1 mM MgCl$_2$. Another set of reactions was performed in the presence of 1 mM CaCl$_2$, which lowers the magnesium ion requirement. In this case, the initial rate of cleavage of the mismatched substrate exceeded that of the matched substrate at 10 and 5 mM MgCl$_2$ and specificity was reversed at 2 and 1 mM MgCl$_2$. Thus, lowering the divalent cation concentration, another method of destabilizing RNA duplexes, also allows the ribozyme to discriminate against mismatched substrates.

Previously we have emphasized the importance of base pairing between the ribozyme and its substrate for both substrate specificity and catalysis (Zaug & Cech, (1986) Science 231:470 and Biochemistry 25:4478; Been & Cech, Cell 1986; Zaug et al., Nature 1986). The current finding that a mismatch in the ribozyme-substrate complex can enhance the cleavage rate by a much as 100-fold seems at first glance to contradict the importance of ribozyme-substrate base pairing. It is therefore useful to review the evidence that initially led us to the base pairing model of FIG. 1. First, there is the clear mechanistic similarity between ribozyme-catalyzed cleavage and RNA self-splicing. In the case of self-splicing, base pairing between the CUCUCU sequence at the 3' end of the 5' exon and the 5' exon binding site GGAGGG within the IVS is proven by comparative sequence analysis (Davies et al., Nature 300:719 1982; Michel & Dujon, EMBO J. 2:33-38 (1983)) and by the analysis of single-base mutations and second-site supressor mutations (Waring et al., Nature 321:133 (1986); Been & Cech, Cell 1986). Second, ribozymic cleavage of large RNA molecules as well as oligoribonucleotide substrates occurs only at sequences that are closely related to CUCUCU↓N, cleavage occurring at the position of the arrow. For example, a 504-nucleotide mouse beta-globin pre-mRNA transcript is cleaved by the L - 19 IVS$_{beta}$ RNA at two major sites, each preceded by CUCU, and an 841-nucleotide pBR$^{322}$ transcript is cleaved at four major sites, two preceded by CUCU, one by CCUU, and one by UUUU (Zaug et al.,Nature, 1986). Finally, active-site mutations alter the substrate specificity in a manner predictable by the rules of Watson-Crick base pairing when reactions are carried out in 2.5 M urea (Zaug et al., Nature, 1986). We must now modify the base-pairing model for the mechanism of oligonucleotide cleavage in the following manner: formation of a base-paired duplex between the ribozyme and its substrate is necessary for reaction, but a mismatched duplex can be better than a perfect duplex.

To facilitate discussion of the data, it is useful to consider a simple reaction scheme:

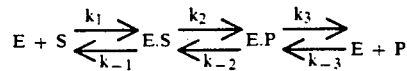

where E is the ribozyme, S is the oligonucleotide substrate, and the products P include both the 5' half of the cleaved substrate and the guanylylated 3' half. (The guanosine substrate is present in vast excess; its binding is not explicitly shown). If K$_m$ ≈ k$_{-1}$/k$_1$, the dissociation constant for E-S, then changes in the substrate at position −3 relative to the cleavage site which result in a mismatched ribozyme-substrate complex should increase K$_m$. The expected trend is seen in rows 5–8 of Table 3. The substrate predicted to form the most stable ribozyme-substrate complex (ΔG° = −7.8 kcal/mol) has the lowest K$_m$, and the three substrates with weaker binding (-3.6 kcal/mol) have considerably higher K$_m$'s. Quantitatively, however, the variation in K$_m$ is much less than expected from the differences in ΔG°; the effect of a mismatch seems to be buffered by other interactions between ribozyme and substrate [cf. Sugimoto et al. Biochemistry, 27:6384, (1988)]. Furthermore, ±or the substrates in rows 1–4 of Table 3, K$_m$ is not significantly affected by mismatches.

Models for the Effect of Mismatches on the Cleavage Rate. During the course of the experiments described here, three models were considered to explain the increased k$_{cat}$ of mismatched substrates. Some tests of the models were performed. (1) Nonproductive Binding. The CUCU-containing substrates would be predicted to have more nonproductive modes of binding to the G-rich active site than CGCU- or CACU-containing substrates; this might explain the reduced k$_{cat}$ of the former. This model was tested by synthesis of the two CCCU-containing substrates, which were expected to have at least as many nonproductive binding modes as CUCU-containing substrates. The high k$_{cat}$ of the CCCU-containing substrates (Table 3) was opposite to the expectation for non-productive binding. Furthermore, nonproductive binding can reduce k$_{cat}$ and K$_m$ but not k$_{cat}$/K$_m$ (Fersht, Enzyme Structure and Mechanism 2nd Ed. Freeman, New York, 1985). If the k$_{cat}$ values of the CUCU-containing substrates are 10–100 fold low due to nonproductive binding, then their K$_m$'s in the absence of nonproductive binding would have to be 10–100-fold larger than the measured K$_m$'s. This seems most unlikely, because the CUCU-containing substrates are the ones that match the active site the best. It remains quite possible that some of the $K_m$ values are reduced because of nonproductive binding. For example, the $C_5$ portion of the $GGCCCCUA_5$ substrate could have multiple nonproductive modes of binding to the G-rich active site of the ribozyme.

(2) Rate-Limiting Product Release. If product release were rate limiting, $k_{cat}$ could be the rate constant for dissociation of the ribozyme-product complex ($k_3$) instead of representing the rate constant for the chemical step ($k_2$). Mismatched substrates would also form mismatched ribozyme-product complexes, thereby increasing $k_{cat}$. This model was tested by performing cleavage with excess ribozyme; with each ribozyme participating in a single turnover, product release is not expected to contribute to $k_{cat}$. The continued faster cleavage of the mismatched substrate observed in ribozyme excess does not support this model.

(3) Mismatches Destabilize E-S. In terms of transition-state theory, mismatches could increase $k_{cat}$ by destabilizing the ground state of E-S without destabilizing the transition state (E-S‡) for the rate-limiting step (Fersht, 1985). Such would leave $k_{cat}/K_m$ unchanged, in accordance with the data in rows 4–8 of Table 3. If a mismatch also stabilized E-S‡, $k_{cat}/K_m$ would increase as observed in rows 1–3 of Table 3. The enhanced cleavage of matched substrates afforded by denaturants such as urea and formamide could be explained if they also destabilized E-S. Inhibition of cleavage of mismatched substrates by the denaturants might be explained if destabilization of the transition-state E-S‡ became dominant.

How could mismatches destabilize E-S and have a different effect on E-S‡? The nucleotides preceding the reactive phosphate could in be bound to the ribozyme in E-S‡ in a manner different from that in the E-S complex. As an extreme possibility, the substrate might become unpaired from the internal template in E-S‡. Note the E-S‡ is the transition state for the rate-limiting step; the data do not distinguish between a rate-limiting chemical step and rate-limiting conformational change in E-S preceding the chemical step.

We propose that optimal cleaves requires a finely tuned degree of stability of the ribozyme-substrate complex. This idea is attractive because it explains the cleavage data in the absence and presence of urea. According to the model, substrates that bind the tightest

$\Delta G° = -10.9$ and $-7.8$ kcal/mol) have the lowest reaction rate in the absence of urea; addition of urea destabilizes their binding and increases their reaction rate (FIG. 21 and Table 3). The next class of substrates

$\Delta G° = -6.7$ kcal/mol) binds with slightly more than optimal stability; addition of 1 M urea gives the maximum reaction rate, while further addition of urea decreases the reaction rate because E-S is destabilized. The final class of substrates

$\Delta G° = -3.6$ kcal/mol) binds too poorly to give an opt reaction rate, so further destabilization caused by addition of urea further lowers the reaction rate. It will be informative to see if mismatches at position $-4$ affect cleavage rates as predicted by the model.

Implications for Self-Splicing. In the self-splicing reaction, guanosine addition occurs in the sequence CUCUCU ↓ A₃ at the position of the arrow. Single-base changes at positions $-1$, $-2$, $-3$, and $-4$ relative to the cleavage site all decrease the rate of splicing (Been et al., Cold Spring Harbor Symp. Quant. Biol. 52:147–157 (1987). In particular, pre-rRNA containing CUCUCU is much more reactive in self-splicing than pre-rRNA containing CUCGCU (Been & Cech, Cell (1986). In the catalytic cleavage of oligonucleotides by L - 21 ScaI RNA, the specificity is reversed, a substrate containing CUCGCU being much more reactive than one containing CUCUCU (except at ≧1 M urea). The enzymatic system tolerates a limited amount of mismatch in the substrate-active-site complex better than the self-splicing system. Perhaps some of the exon or intron sequences removed when the self-splicing pre-rRNA is converted into the L - 21 ScaI RNA enhance the specificity of splice site selection.

Use of Ribozymes for Sequence-Specific cleavage of RNA. The present work has implications for the use of ribozymes as tools for the sequence-specific cleavage of RNA. We see the importance of nucleotides at positions $-5$ and $-6$ from the cleavage site. It is now clear that the substitution of a C for U at position $-5$ has a minimal effect on $k_{cat}$ but can have a very large effect on the $K_m$ of the cleavage reaction (Table 3). Second, and much more fundamentally, certain mismatched sequences are efficiently cleaved even in the presence of urea. Most dramatic is $GGCCCCCU \downarrow A_5$; although its cleavage is strongly inhibited by urea, it is such a good substrate that it is still cleaved more rapidly than the cognate sequences

in 2–2.5 M urea. A similar mismatched sequence (CCCL ↓ ) has been found to be a major site of cleavage of a 602-nucleotide SV40 transcript by the L - 21 ScaI RNA. It seems likely that discrimination against mismatched substrates can be further improved by increasing the urea concentration to 3 M or by decreasing the magnesium ion concentration to 2 mM. Unless reaction conditions are carefully specified, however, ribozyme cleavage of RNA molecules will generally occur at a family of sites that includes the sequence that matches the ribozyme active site as well related sequences that contain one or two mismatched nucleotides.

This incorporates by reference the work in Zaug, Arthur J., et al. Biochemistry (1988) 27:8924.

EXAMPLE VIII

The active site of pBGST7 has been mutagenized (see Example XV below) to produce new ribozymes with altered specificity. Six of these have been synthesized and characterized.

These mutants can be produced from the plasmid producing the L - 19 or L - 21 wild type ribozymes wherein the active sites are mutagenized as shown in Table 5.

The internal guide sequence of the IVS can be mutagenized to construct these variants (Been and Cech (1986) Cell 47:207-216. The RNA can be transcribed and prepared using similar procedures as for the wild-type ribozyme.

Each of the six new ribozymes recognizes and cleaves at the new substrate sequence predictable by the rules established in our previous work (Zaug, Been & Cech, Nature 1986). The conditions for reactivity of some of these new ribozymes vary from conditions used for the wild-type ribozyme. While the wild-type ribozyme has a $Mg^{++}$ concentration optimum around 2 mM, several of our variant ribozymes are more reactive at higher $Mg^{++}$ concentrations (up to 100 mM).

The summary of wild-type and new ribozymes is found in Table 5. We used 2.5 M urea to increase the fidelity of cleavage site selection with the wild-type ribozyme. This condition works well for some but not all of our variants. The reactivities of ribozymes TTA and TTC decrease substantially with increasing urea. The use of high concentrations of salts such as ammonium acetate ($NH_4Ac$) is found to aid fidelity in these cases. Other salts including $NH_4Cl$, $LiCl$, $CaCl_2$ and spermidine can substituted for $NH_4Ac$.

Figure 22:
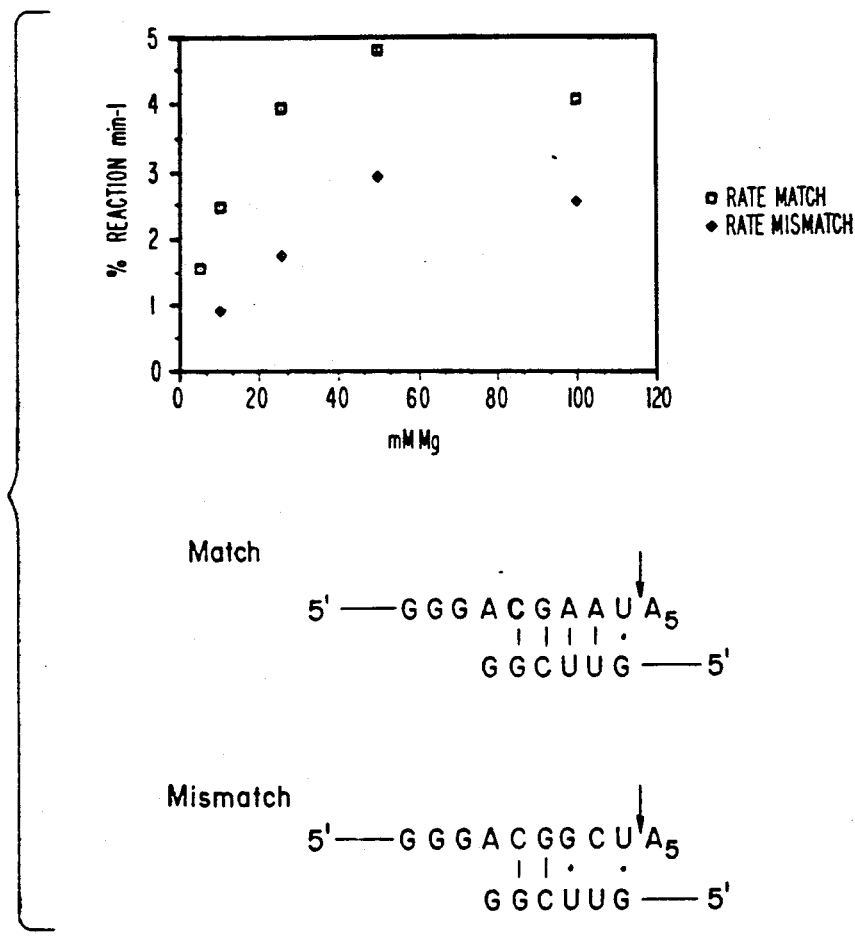
Figure 23:
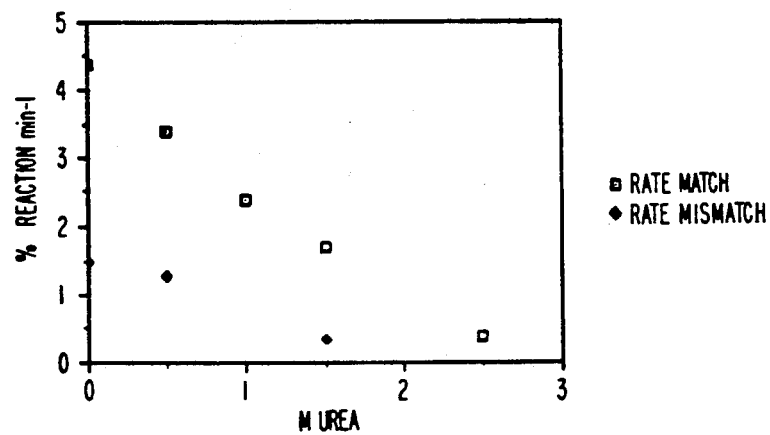
Figure 24:
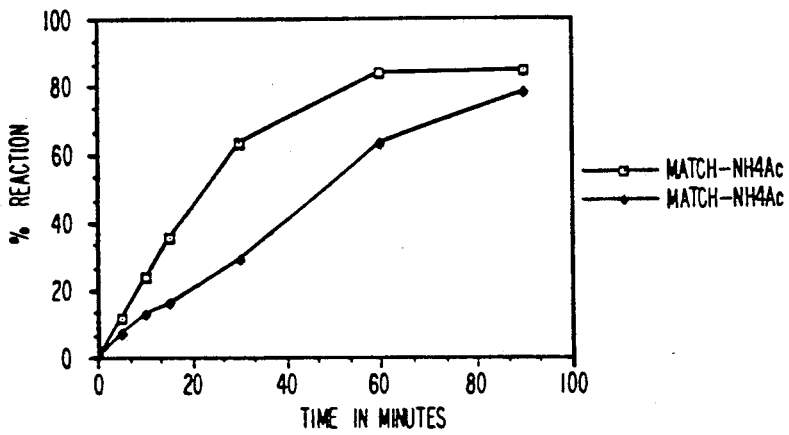
Figure 25:
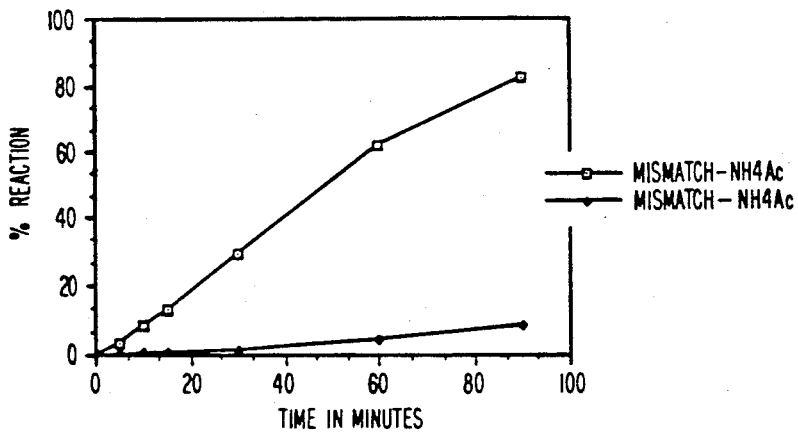
Figure 27:
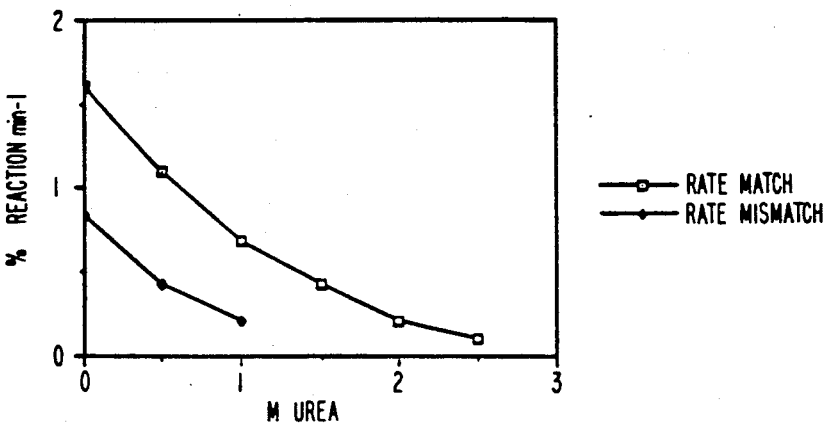
Figure 28:
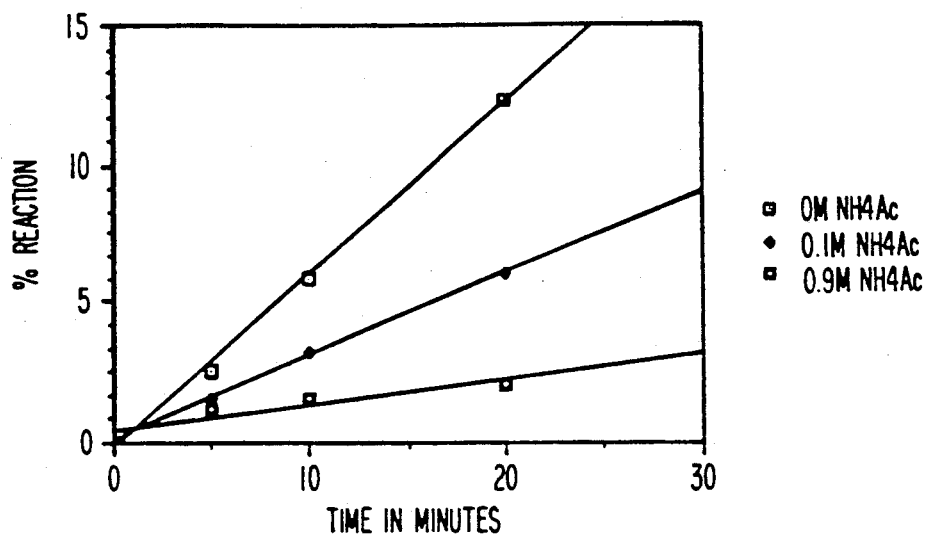
Figure 29:
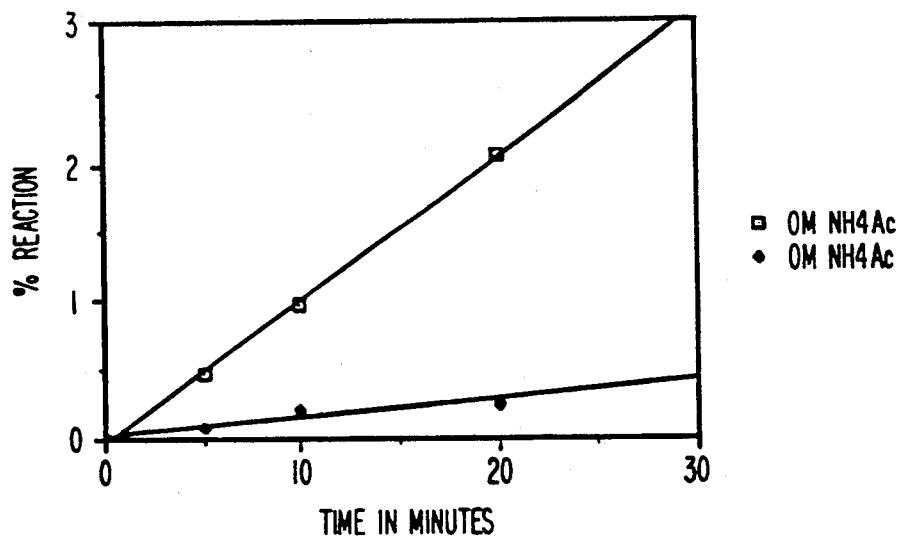
Figure 30:
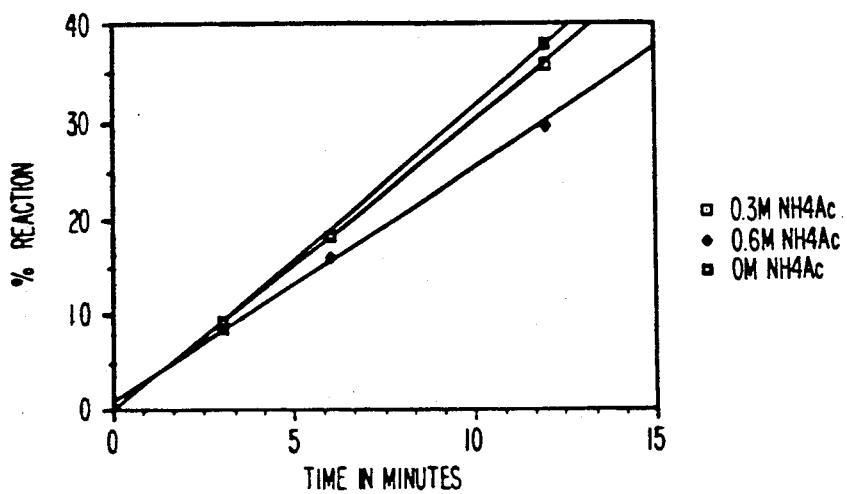
Figure 31:
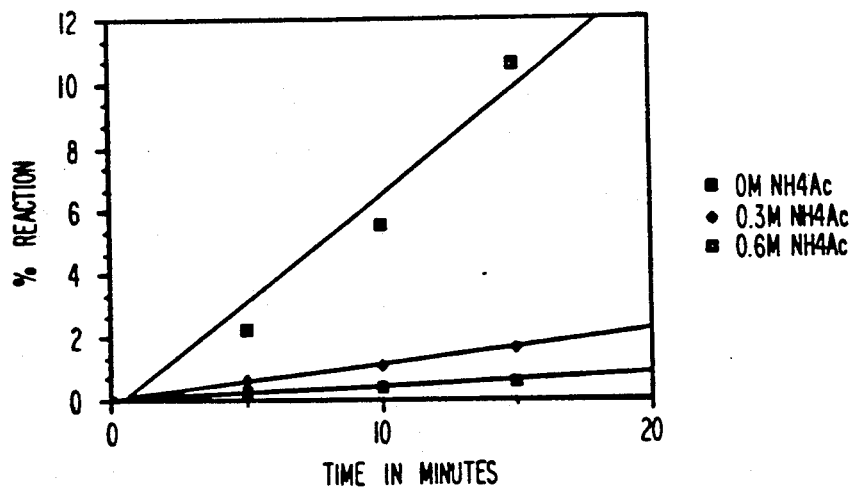

These points are illustrated in FIGS. 22-31. Ribozyme TTC has poor specificity at a variety of $MgCl_2$ concentrations if salt and urea are absent (FIG. 22). This ribozyme has better specificity at 1.5M urea, but it loses activity with the matched substrate under this condition (FIG. 23). Salt (in this case $NH_4Ac$) has only a slight effect on cleavage of the matched substrate (FIG. 24), but substantially reduces cleavage of the mismatched substrate (FIG. 25), thereby increasing specificity. The same points are illustrated for ribozyme TTA in FIGS. 26-29. $NH_4Ac$ also serves to increase the specificity of ribozyme TGT (FIGS. 30-31).

EXAMPLE IX

Figures 5A, 5B:
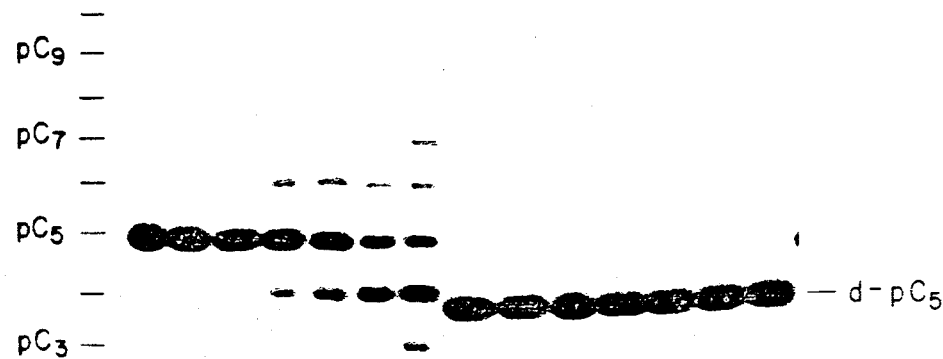
FIG. 5A-5G show the cleavage and reforming of oligoribonucleotide substrates by L-19 IVS RNA.
Figures 5C, 5D:
Figures 5E, 5F, 5G:
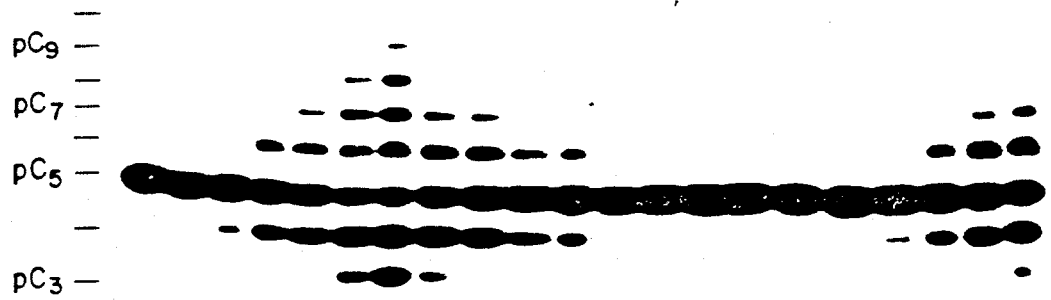

The L-19 IVS RNA catalyzes the cleavage and rejoining of oligonucleotides:

Unlabeled L-19 IVS RNA was incubated with 5'-$^{32}$P-labeled $pC_5$ in a solution containing 20 mM $MgCl_2$, 50 mM tris-HCl, pH 7.5. The $pC_5$ was progressively converted to oligocytidylic acid with both longer and shorter chain length than the starting material (FIG. 5A). The longer products extended to at least $pC_{30}$, as judged by a longer exposure of an autoradiogram such as that shown in FIG. 5A. The shorter products were exclusively $pC_4$ and $pC_3$. Incubation of $pC_5$ in the absence of the L-19 IVS RNA gave no reaction (FIG. 5C).

Phosphatase treatment of a 60-minute reaction mixture resulted in the complete conversion of the $^{32}$P radioactivity to inorganic phosphate, as judged by polyethyleneimine thin-layer chromatography (TLC) in 1M sodium formate, pH 3.5 (Zaug, A., et al. unpublished data). Thus, the 5'-terminal phosphate of the substrate does not become internalized during the reaction, and the substrate is being extended on its 3' end to form the larger oligonucleotides. When $C_5p^*C$ was used as the substrate and the products were treated with ribonuclease $T_2$ or ribonuclease A, the $^{32}$P radioactivity was totally converted to $Cp^*$ (Zaug, A., et al. unpublished data). Thus, the linkages being formed in the reaction were exclusively 3',5'-phosphodiester bonds. The products of the $C_5p^*C$ reaction were totally resistant to phosphatase treatment.

The reaction was specific for ribonucleotides, no reaction taking place with d-$pC_5$ (FIG. 1B) or d-$pA_5$ (Zaug, A., et al. unpublished data). Among the oligoribonucleotides, $pU_6$ was a much poorer substrate than $pC_5$ or $pC_6$ (FIG. 5D), and $pA_6$ gave no reaction (Zaug, A., and Cech, T. R., (1986), Biochemistry 25:4478).

No reaction occurred when magnesium chloride was omitted. The enzyme activity was approximately constant in the range 5 to 40 mM $MgCl_2$ (Zaug, A., et al. unpublished data). The 20 mM concentration was routinely used to circumvent the potential effect of chelation of $Mg^{2+}$ by high concentrations of oligonucleotide substrates.

The L-19 IVS RNA is regenerated after each reaction, such that each enzyme molecule can react with many substrate molecules. For example, quantitation of the data shown in FIG. 5G revealed that 16 pmol of enzyme converted 1080 pmol of $pC_5$ to products in 60 minutes. Such numbers underestimate the turnover number of the enzyme; because the initial products are predominantly $C_6$ and $C_4$, it is likely that the production of chains of length greater than six or less than four involves two or more catalytic cycles. Quantitation of the amount of radioactivity in each product also provides some indication of the reaction mechanism. At early reaction times, the amount of radioactivity (a measure of numbers of chains) in products larger than $pC_5$ is approximately equal to that found in $pC_4$ plus $pC_3$, consistent with a mechanism in which the total number of phosphodiester bonds is conserved in each reaction. As the reaction proceeds, however, the radioactivity distribution shifts toward the smaller products. This is most likely due to a competing hydrolysis reaction also catalyzed by the L-19 IVS RNA, as described below.

The rate of conversion of 30 uM $pC_5$ to products increases linearly with L-19 IVS RNA enzyme concentration in the range 0.06 to 1.00 uM (Zaug, A., et al. unpublished data). At a fixed enzyme concentration (FIG. 5, E to G), there is a hyperbolic relation between the reaction rate and the concentration of $pC_5$. The data are fit by the Michaelis-Menten rate law in FIG. 6. The resulting kinetic parameters are $K_m = 42$ uM and $k_{cat} = 1.7$ min$^{-1}$.

The stability of the enzyme was determined by preliminary incubation at 42° C for 1 hour in the presence $o \pm Mg^{2+}$ (standard reaction conditions) or for 18 hours under the same conditions but without $Mg^{2+}$. In both cases, the incubated enzyme had activity indistinguishable from that of untreated enzyme tested in parallel, and no degradation $o \pm$ the enzyme was observed on polyacrylamide gel electrophoresis (Zaug, A., et al. unpublished data). Thus, the L-19 IVS RNA is not a good substrate. The enzyme is also stable during storage at $-20°$ C. for periods of months. The specific activity of the enzyme is consistent between preparations.

EXAMPLE X

Covalent intermediate. When $C_5p^*$ was used as a substrate, radioactivity became covalently attached to the L-19 IVS RNA (FIG. 7A) (The radioactive phosphate was bonded covalently to the L-19 IVS RNA as judged by the following criteria: it remained associated when the complex was isolated and subjected to a second round of denaturing gel electrophoresis; it was released in the form of a mononucleotide upon RNase $T_2$ treatment; and it was released in the form of a series of unidentified oligonucleotides upon RNase $T_1$ treatment (A. Zaug and T. Cech, unpublished data). These results are consistent with a series of covalent enzyme-substrate complexes in which various portions of $C_5p^*C$ are linked to the L-19 IVS RNA via a normal 3'-5'-phosphodiester bond. This observation, combined with our previous knowledge of the mechanism of IVS RNA cyclization (Zaug, A. J., et al., (1984) Science 224:574; Sullivan and Cech, T. R., (1985) Cell 42:639; Zaug, A. J., et al. (1983) Nature (London) 301:578), Been, M. and Cech, T. R. (1985) Nucleic Acids Res. 13:8389), led to a model for the reaction mechanism involving a covalent enzyme-substrate intermediate (FIG. 8).

This reaction pathway is supported by analysis of reactions in which a trace amount of $p^*C_5$ was incubated with a large molar excess of L-19 IVS RNA. The cleavage reaction occurred with high efficiency, as judged by the production of $p^*C_4$ and $p^*C_3$, but there was very little synthesis of products larger than the starting material (FIG. 7B; compare to FIG. 5A). These data are easily interpreted in terms of the proposed reaction pathway. The first step, formation of the covalent intermediate with release of the 5'-terminal fragment of the oligonucleotide, is occurring normally. The first step consumes all the substrate, leaving insufficient $C_5$ to drive the second transesterification reaction.

The model shown in FIG. 8 was tested by isolating the covalent enzyme-substrate complex prepared by reaction with $C_5p^*C$ and incubating it with unlabeled $C_5$. A portion of the radioactivity was converted to oligonucleotides with the electrophoretic mobility of $C_6$, $C_7$, $C_8$, and higher oligomers (FIG. 7C). In a confirmatory experiment, the covalent complex was prepared with unlabeled $C_5$ and reacted with $p^*C_5$. Radioactivity was again converted to a series of higher molecular weight oligonucleotides (Zaug, A., et al. unpublished data). In both types of experiments the data are readily explained if the covalent complex is a mixture of L-19 IVS RNA's terminating in . . . GpC, . . . GpCpC, . . . GpCpCpC, and so on. Because they can react with $C_5$ to complete the catalytic cycle, these covalent enzyme-substrate complexes are presumptive intermediates in the reaction (FIG. 8). A more detailed analysis of the rate of their formation and resolution is needed to evaluate whether or not they are kinetically competent to be intermediates. We can make no firm conclusion about that portion of the enzyme-substrate complex that did not react with $C_5$. This unreactive RNA could be a covalent intermediate that was denatured during isolation such that it lost reactivity, or it could represent a small amount of a different enzyme-substrate complex that was nonproductive and therefore accumulated during the reaction.

The $G^{414}$ linkage in the C IVS RNA, the $G^{414}$-$U^{20}$ linkage in the C' IVS RNA, and the $G^{414}$-$U^{415}$ linkage in the pre-rRNA are unusual phosphodiester bonds in that they are extremely labile to alkaline hydrolysis, leaving 5' phosphate and 3'-hydroxyl termini (Zaug, A. J. et al, (1984) Science 224:574 and Inoue, T., et al. (1986) J. Mol. Biol. 189,143-165). We therefore tested the lability of the $G^{414}$-C linkage in the covalent enzyme-substrate intermediate by incubation at pH 9.0 in a $Mg^{2+}$-containing buffer. This treatment resulted in the release of products that comigrated with pC and pCpC markers and larger products that were presumably higher oligomers of pC (FIG. 7D). Thin-layer chromatography was used to confirm the identity of the major products (Zaug, A., et al. unpublished data). In those molecules that released pC, the release was essentially complete in 5 minutes. Approximately half of the covalent complex was resistant to the pH 9.0 treatment. Once again, we can make no firm conclusion about the molecules that did not react. The lability of the $G^{414}$-C bond forms the basis for the L-19 IVS RNA acting as a ribonuclease (FIG. 8) by a mechanism that is distinct from that of the endoribonuclease described in Examples I through VI.

A competitive inhibitor. Deoxy $C_5$, which is not a substrate for L-19 IVS RNA-catalyzed cleavage, inhibits the cleavage of $pC_5$ (FIG. 9A). Analysis of the rate of the conversion of $pC_5$ to $pC_4$ and $pC_3$ as a function of d-$C_5$ concentration is summarized in FIG. 9B and C. The data indicate that d-$C_5$ is a true competitive inhibitor with the inhibition constant $K_i = 260$ uM. At 500 uM, d-$A_5$ inhibits the reaction only 16 percent as much as d-$C_5$. Thus, inhibition by d-$C_5$ is not some general effect of introducing a deoxyoligonucleotide into the system but depends on sequence.

The formation of the covalent enzyme-substrate intermediate (EpC) can be represented as

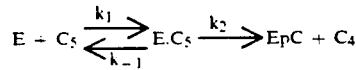

If $k_{-1} \gg k_2$, then $K_m = k_{-1}/k_1$, the dissociation constant for the noncovalent $E \cdot C_5$ complex. The observation the the $K_i$ for d-$C_5$ is within an order of magnitude of the $K_m$ for $C_5$ can then be interpreted in terms of d-$C_5$ and $C_5$ having similar binding constants for interaction with the active site on the enzyme. This fits well with the idea that the substrate binds to an oligopurine ($R_5$) sequence in the active site primarily by Watson-Crick base-pairing, in which case the $C_5 \cdot R_5$ duplex and the d-$C_5 \cdot R_5$ duplex should have similar stability.

Enzyme mechanism and its relation to self-splicing. The stoichiometry of the reaction products (equimolar production of oligonucleotides smaller than and larger than the starting material), the lack of an ATP or GTP (adenosine triphosphate; guanosine triphosphate) energy requirement, the involvement of a covalent intermediate, the specificity for oligoC substrates, and the competitive inhibition by d-$C_5$ lead to a model for the enzyme mechanism (FIG. 8). The L-19 IVS RNA is proposed to bind the substrate noncovalently by hydrogen-bonded base-pairing interactions. A transesterification reaction between the 3'-terminal guanosine residue of the enzyme and a phosphate ester of the substrate then produces a covalent enzyme-substrate intermediate.

Transesterification is expected to be highly reversible. If the product $C_4$ rebinds to the enzyme, it can attack the covalent intermediate and reform the starting material, $C_5$. Early in the reaction, however, the concentration of $C_5$ is much greater than the concentration of $C_4$; if $C_5$ binds and attacks the covalent intermediate, $C_6$ is produced (FIG. 8). The net reaction is 2 $C_5$ converted to $C_6 + C_4$. The products are substrates for further reaction, for example, $C_6 + C_5$ is converted to $C_7 + C_4$ and $C_4 + C_5$ is converted to $C_3 + C_6$. The absence of products smaller than $C_3$ is explicable in terms of the loss of binding interactions of $C_3$ relative to $C_4$ ($C_3$ could form only two base pairs in the binding mode that would be productive for cleavage).

The transesterification reactions are conservative with respect to the number of phosphodiester bonds in the system. Thus, RNA ligation can occur without an external energy source as is required by RNA or DNA ligase. Hydrolysis of the covalent intermediate competes with transesterification. The net reaction is $C_5+H_2O$ converted to $C_4+pC$, with the L-19 IVS RNA acting as a ribonuclease.

On the basis of our current understanding of the reaction, the catalytic strategies of the L-19 IVS RNA enzyme appear to be the same as those used by protein enzymes (Jencks, W. P., (1969) Catalysis in Chemistry and Enzymology (McGraw-Hill, New York). First, the RNA enzyme, like protein enzymes, forms a specific noncovalent complex with its oligonucleotide substrate. This interaction is proposed to hold the oligonucleotide substrate at a distance and in an orientation such as to facilitate attack by the 3'-hydroxyl of the terminal guanosine of the enzyme. Second, a covalent enzyme-substrate complex is a presumptive intermediate in the L-19 IVS RNA reaction. Covalent intermediates are prevalent in enzyme-catalyzed group transfer reactions. Third, the phosphodiester bond formed in the covalent intermediate is unusually susceptible to hydrolysis, suggesting that it may be strained or activated to facilitate formation of the pentavalent transition state upon nucleophilic attack (Zaug, A. J., et al. (1985) Biochemistry 24:6211; Zaug, A. J., et al. (1984) Science 224:574). Similarly, protein catalysts are thought to facilitate the formation of the transition state, for example, by providing active site groups that bind the transition state better than the unreacted substrate (Fersht, A., (1985) Enzyme Structure and Mechanism (Freeman, New York, ed. 2); Wells, T. N. C., et al. (1985) Nature (London) 316:656). Thus far there is no evidence that another major category of enzyme catalysis, general acid-base catalysis, occurs in the L-19 IVS RNA reactions, but we think it likely that it will be involved in facilitating the required proton transfers.

Each L-19 IVS RNA-catalyzed transesterification and hydrolysis reaction is analogous to one of the steps in Tetrahymena pre-rRNA self-splicing or one of the related self-reactions (FIG. 10). Thus, the finding of enzymatic activity in a portion of the IVS RNA validates the view that the pre-rRNA carries its own splicing enzyme as an intrinsic part of its polynucleotide chain. It seems likely that the $C_5$ substrate binding site of the L-19 IVS RNA is the oligopyrimidine binding site that directs the choice of the 5' splice site and the various IVS RNA cyclization sites (Sullivan, F. X., et al. (1985) Cell Supra; Been, M., et al. (1985) Nucleic Acid Research Supra; Inoue, T., et al. J. Mol. Biol., Supra; Inoue, T., et al. (1985) Cell 43:431. Although the location of this site within the IVS RNA has not been proved, the best candidate is a portion of the "internal guide sequence" proposed by Davies and co-workers (Davies, R. W., et al. (1982) Nature (London) 300:719; Waring, R. B., et al. (1983) J. Mol. Biol. 167:595). Michel and Dujon (Michel, F., et al. (1983) EMBO J. 2:33) show a similar pairing interaction in their RNA structure model. The putative binding site, GGAGGG, is located at nucleotides 22 to 27 of the intact Tetrahymena IVS RNA and at positions 3 to 8 very near the 5' end of the L-19 IVS RNA. If this is the substrate binding site, site-specific mutation of the sequence should change the substrate specificity of the enzyme in a predictable manner.

EXAMPLE XI

The L-19 IVS RNA Dephosphorylates $C_6p$. When oligo(cytidylic acid) with a 3'-terminal hydroxyl group is incubated with the L-19 IVS RNA enzyme in 20 mM $MgCl_2$, it is converted to oligo(C) with both larger and smaller chain lengths (FIG. 1A) as described previously (Examples VII and VIII and Zaug & Cech, (1986) Science (Wash., D.C.) 231:470–475. The reaction is specific for oligo(C); for example, $pA_6$-OH is unreactive under the same conditions (FIG. 11A).

When oligo(cytidylic acid) with a 3'-terminal phosphate is incubated with excess L-19 IVS RNA in 20 mM $MgCl_2$, the substrate is converted to a product with reduced electrophoretic mobility (FIG. 11A). This abrupt reduction in electrophoretic mobility, equivalent to an increase of approximately three nucleotides on a sequencing ladder, is exactly that obtained by treating the substrate with alkaline phosphatase (not shown in FIG. 11; an example is shown in FIG. 12). Thus, it appeared that the product was $C_6$-OH. When the substrate is internally labeled ($C_5p^*Cp$), the labeled phosphate is retained in the product (FIG. 11A). On the other hand, when the substrate is terminally labeled ($C_5p^*$), the oligonucleotide product is unlabeled and the L-19 IVS RNA becomes labeled (FIG. 11B). These findings confirmed that the reaction involves removal of the 3'-terminal phosphate of the substrate.

Dephosphorylation is specific for the 3'-phosphate of oligo(cytidylic acid). The 5'-phosphate of $pC_5$ is not reactive (FIG. 11A), and neither phosphate is removed from pCp (data not shown). (We estimate that 0.1% reaction would have been detected). Neither $A_6Cp$ (FIG. 11A) nor $pA_6p$ (not shown) is a substrate. (We estimate that 0.1% reaction would have been detected). On the basis of this sample, it appears that there is both a minimum length requirement and a sequence requirements for a substrate and that the requirement are similar to those of the nucleotidyl transfer activity of the L-19 IVS RNA (Zaug & Cech, (1986) Science Supra).

EXAMPLE XII

Formation and Stability of E-p. We next investigated the fate of the phosphate that is removed from $C_5p$ in the presence of L-19 IVS RNA. At neutral pH no inorganic phosphate is formed during the reaction, as judged by thin-layer chromatography of the reaction products (data not shown). When the reaction is conducted in the presence of $C_5p^*$, it becomes clear that the phosphate is transferred to the L-19 RNA (FIG. 11B). Treatment of the phosphorylated L-19 IVS RNA (hereafter called E-p) with alkaline phosphatase leads to quantitative release of the radioactivity in the form of inorganic phosphate. Thus, the dephosphorylation of the substrate is accomplished by transphosphorylation. The structure of E-p has been determined; the phosphate is esterified through the 3'-O of the 3'-terminal guanosine residue (G414) of the RNA (Zaug and Cech, unpublished results).

Figure 12A:
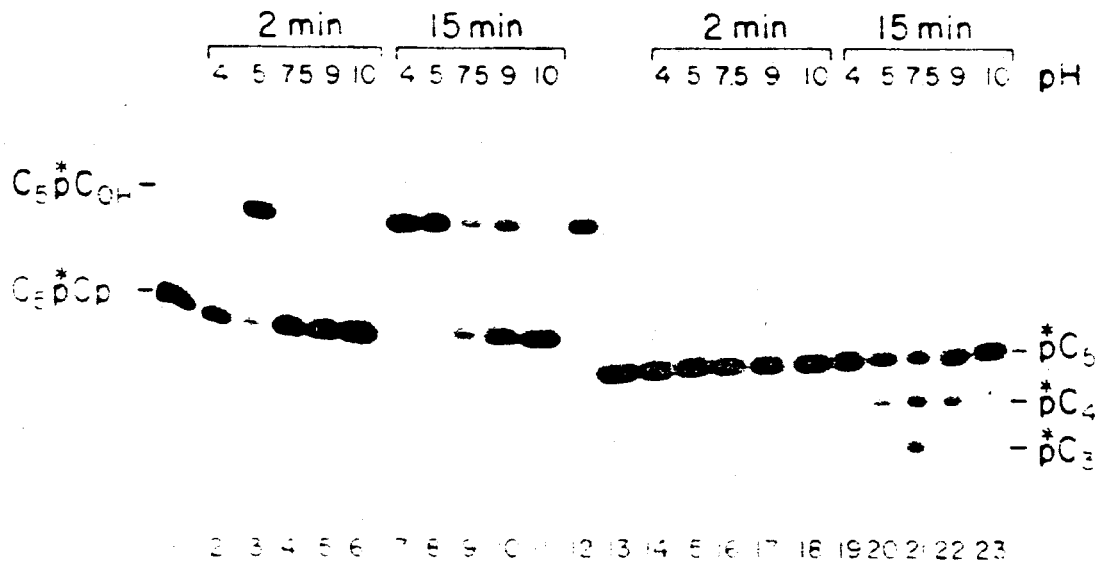
FIG. 12A, 12B, and 12C show the effect of pH on phosphotransfer and nucleotidyl transfer reactions.
Figure 12B:
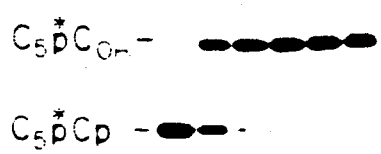
Figure 12C:
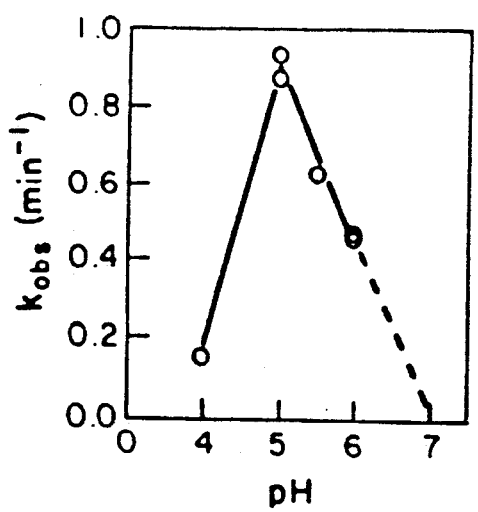

The rate of conversion of $G_5p$ to $C_5$-OH+E-p is pH-dependent with an optimum around pH 5.0. A sample of the data is shown in FIG. 12. The phospho transfer reaction is essentially pH-independent in the range pH 7.5-9 and proceeds at a rate similar to that of the nucleotidyl transfer reaction (FIG. 12A). At pH 5 the phospho transfer reaction is accelerated more than 20-fold, while the nucleotidyl transfer reaction is unaffected. At pH 4, the enzyme still has substantial phospho transfer activity while its nucleotidyl transfer activity is greatly diminished. Since the enzyme is probably starting to denature below pH 5 (Zaug, et al., (1985) Biochemistry 24:6211) the phospho transfer activity profile in this range presumably reflects the inactivation of the enzyme rather than the pH optimum for the transfer step. Data such as those shown in FIG. 12B were quantified, and the resulting rate constants are summarized in FIG. 12C.

The covalent intermediate formed during the reaction of $pC_5$-OH with the L-19 IVS RNA (E-pC) is alkali-labile; at pH 9.0 it undergoes hydrolysis, releasing the nucleotide pC and regenerating the free enzyme (Zaug & Cech, (1986) Science Supra). We therefore investigated the stability of the phosphate monoester in the phosphenzyme E-p. There is no detectable hydrolysis of the phosphate monoester at pH 9.0, conditions in which E-pC treated in parallel gave release of pC, or at any other pH in the range 7.0-9.0.

At acidic pH, on the other hand, the terminal phosphate monoester of E-p underwent slow hydrolysis. When E-p was incubated at pH 5.0, the phosphate was released as $P_i$ at a rate of approximately 10%/h. The rate was slower at pH 4.0 and at pH 6.0 than at pH 5.0. Release of $P_i$ was also observed during the reaction of $C_5p^*$ with L-19 IVS RNA at pH 5.0 at reaction times of 2 and 4h. Thus, the L-19 IVS RNA has acid phosphatase activity. This hydrolytic reaction is so slow, however, that we have not attempted to demonstrate multiple turnover.

EXAMPLE XIII

Phosphorylation of the Enzyme Is Reversible. When unlabeled E-p is incubated with a trace amount of $C_5p^*$, very little reaction takes place (FIG. 13A). In contrast, when the same E-p is incubated with a trace amount of labeled $pC_5$-OH, labeled $pC_5p$ is progressively formed (FIG. 13B). The products normally formed by incubation of $pC_5$-OH with excess L-19 IVS RNA, $pC_4$-OH and $pC_3$-OH (Zaug & Cech, 1986), are not observed. Thus, E-p is inactive as a nucleotidyltransferase but is readily subject to a reverse phosphorylation reaction.

The reversibility of phosphorylation of the L-19 IVS RNA was confirmed by reacting the enzyme with $C_5p^*$ to form E-$p^*$, purifying the E-$p^*$, and incubating it with unlabeled $C_5$-OH. A labeled product corresponding to $C_5p^*$ was produced (data not shown). This approach allowed to rapid screening of a series of nucleotides and oligonucleotides for their ability to reverse the phosphorylation reaction. As shown in Table 2, of the oligonucleotides tested only UCU and $C_4U$ had activity comparable to the of $C_5$. It remains possible that some of the other oligonucleotides have a high $K_m$ and would have detectable activity at a higher concentration.

EXAMPLE XIV

Figure 14A:
FIG. 14A, 14B, and 14C show the L-19 IVS RNA acts catalytically as a phosphotransferase.
Figure 14B:
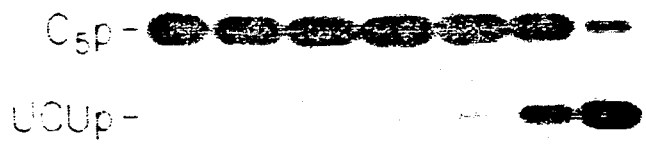
Figure 14C:
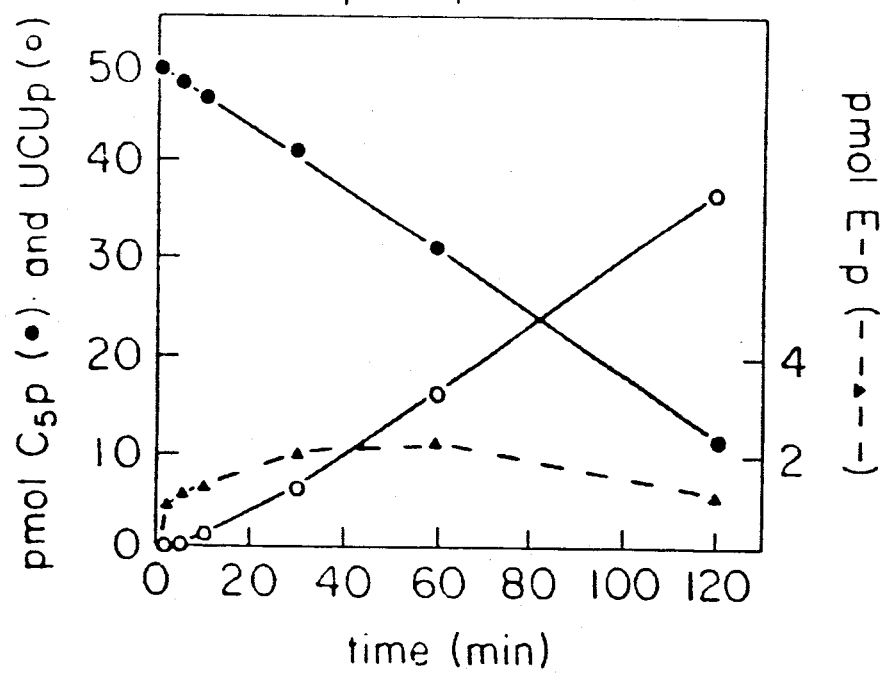

The L-19 IVS RNA Is a Phosphotransferase. The phosphotransfer reactions described thus far were all done in enzyme excess. To prove that the L-19 IVS RNA could act catalytically, it was necessary to show that each enzyme molecule could mediate the dephosphorylation of multiple substrate molecules. This was accomplished by the incubation of L-19 IVS RNA with a molar excess of $C_5p^*$ and an even greater molar excess of unlabeled UCU, to act as a phosphate acceptor. As shown in FIG. 14A, L-19 IVS RNA was capable of transferring the 3'-terminal phosphate from $C_5p$ to UCU. Treatment of the product with RNase $T_2$ and thin-layer chromatography confirmed that the phosphate had been transferred from a C to a U residue. The time course in FIG. 14B was done under conditions of lower enzyme concentration (0.16 uM) and higher acceptor concentration (200 uM) than those used in the experiment of FIG. 14A. Quantitation of the data (FIG. 14C) showed that under these conditions 11 substrate molecules were dephosphorylated per enzyme molecule after 120 min. Phosphorylation of the enzyme precedes substantial product formation, consistent with E-p being an oligatory intermediate in the reaction. At steady state 63% of the enzyme is present as E-p.

EXAMPLE XV

Plasmid Construction pBGST7

Been, Michael D. and Cech, Thomas, R. (1986) Cell 47:207-216 reports the construction of the pBG plasmid series. In general, the plasmid used for these studies (pBGST7) was derived from the cloning vector $pUC_{18}$. The methodology for the following manipulations is described in Maniatis, T., et al. (1982) Molecular Cloning: A Laboratory Manual (Cold Spring Harbor, New York: Cold Spring Harbor). $pUC_{18}$ was partially digested with HaeII and unit length linear molecules were isolated by agarose gel electrophoresis and electroelution. The recovered DNA was treated with $T_4$ DNA polymerase to make blunt ends and then dephosphorylated with calf intestinal phosphatase. $pT_7$-2 (U.S. Biochemical Corp.) was cut with PvuII and HindIII and treated with $T_4$ DNA polymerase, and the fragment containing the phage T7 promoter was isolated by polyacrylamide gel electrophoresis and electroelution. The promoter-containing fragment was ligated into the linearized $pUC_{18}$ and the plasmid transformed into E. coli strain JM83. Individual colonies were picked and miniprep DNA was screened by restriction endonuclease digestion to locate the promoter fragment to the correct HaeII site (position 680 on the map in the New England Biolabs Catalog). The orientation of the T7 promoter was determined by transcribing EcoRI-cut miniprep DNA with T7 RNA polymerase and determining the size of the product. This plasmid (pUT718) was then cut in the multicloning site with KpnI and SphI and treated with T4 DNA polymerase followed by calf intestinal phosphatase. An IVS-containing BamHI DNA fragment was isolated from pJE457 (Price, J. V. and Cech, T. R., (1985) Science 228:719-722) and treated with S1 nuclease, phenol extracted, chloroform extracted, and ethanol precipitated. The S1-treated fragment, containing short deletions at both ends, was ligated into the KpnI/SphI-cut pUT718. E. coli strain JM83 was transformed with the recombinant plasmid and plated on LB agar containing ampicillin and X-gal (5-bromo-4-chloro-3-indolyl-beta-D-galactoside). DNA isolated from blue colonies was assayed by agarose gels electrophoresis for IVS-size inserts. Exon sequences were determined by dideoxy-sequencing the miniprep DNA. Ideally, only plasmids containing IVS and exons that will preserve the reading frame of the laxZ gene fragment should give blue colonies and this will depend on the splicing of the message in E. coli (Waring, R. B., et al., (1985) Cell 40:371-380; Price, J. V. and Cech, T. R., (1985) Science 228:719;14 722). In fact, several plasmids that conferred a light blue color to the colonies had exons for which correct splicing of the IVS should not generate the proper reading frame; these were not investigated further. One that produced a dark blue colony, pBGST7 (FIG. 16), also had the expected reading frame and was used for these studies.

Mutagenesis

Oligonucleotide-directed mutagenesis on plasmid DNA was done essentially as described by Inouye, S. and Inouye M. (1986) In DNA and RNA Synthesis, S. Narang. ed. (New York: Academic Press). in press. pBGST7 DNA was cleaved in the gene coding for ampicillin resistance with XmnI. In a separate reaction, pBGST7 DNA was cut with EcoRI and HindIII, sites that flank the IVS and exon sequences. The vector portion of the plasmid was separated from the IVS-containing fragment by agarose gel electrophoresis and recovered by electroelution. XmnI-cut DNA was mixed with the vector fragment in the presence of the oligonucleotide containing the mismatched base, heated to 95° C. for 5 min. placed at 37° C. for 30 min, then at 4° C. for 30 min and then put on ice. The products were treated with dNTPs and Klenow fragment of DNA pol I at room temperature for 2 hr. E. coli strain JM83 was transformed with the DNA and ampicillin-resistant colonies were picked on the basis of color (white or light blue indicating loss of splicing activity) and the miniprep DNA was sequenced.

The double mutants were made using the plasmid DNA of single mutants and screening for restored beta-galactosidase activity. pBG/-2G:23C was made from pBG/-2G and a second oligonucleotide directed at position 23. pBG/-3G:24C was made starting with pBG/24C and using the oligonucleotide directed at position -3. pBG/-4G:25C was made by generating a circular heteroduplex from pBG/-4G:25C that had been linearized at different positions. Transformation of these heteroduplexes generated blue and light blue colonies, both at a low frequency. The blue colonies were wild-type sequence the light blues double mutant.

pSPTT1A3

The ThaI fragment of Tetrahymena ribosomal RNA gene contains the IVS and small portions of the flanking exons. Hind III linkers were ligated onto the ends of the ThaI fragment and it was inserted into the Hind III site in the polylinker of pSP62 (New England Nuclear), which contains the SP6 promoter. The recombinant plasmid was cloned in E. coli by standard methods.

pT7TT1A3

Construction of pT7TT1A3 was identical to pSPTT1A3 except that the ThaI fragment was cloned into the Hind III site of pT7-2 (U.S. Biochemical Corp.) which contains the T7 promoter.

pT7 L-21 plasmid pBGST7 (described in Been & Cech, (1986) Cell 47:207 was cleaved with restriction endonucleases SphI and Hind III and the small fragment containing the IVS minus its first 44 nucleotides was purified. pUC18 was cleaved with SpH I and Hind III, mixed with the Sph-HIND III fragment from pBGST7 and treated with DNA ligase. E. coli cells were transformed, colonies were picked, plasmid DNA was isolated from individual colonies and sequenced. A plasmid containing the SphI-Hind III fragment of the IVS properly inserted into pUC18 was selected ±or the next step. This plasmid was cleaved with SphI and EcoRI restriction endonucleases and a synthetic oligonucleotide was inserted into the plasmid using DNA ligase. The synthetic oligonucleotide contained one-half of the EcoRI restriction site, the T7 promoter, and nucleotides 22-44 of the Tetrahymena IVS, ending at the SphI site. E coli cells were transformed, colonies were picked, plasmid DNA was isolated from individual colonies and sequenced.

The final plasmid pT7L-21 was found by sequence analysis to contain the T7 promoter properly juxtaposed to nucleotide 22 of the IVS. (See FIG. 16 and 19)

Therefore the method can be used to create defined pieces of RNA. For example, these defined pieces can be 5'-OH or 3'-OH end pieces, or center pieces containing the active site for study and production of varient RNA forms.

TABLE 1

Sites of cleavage of large RNA substrates by the wild-type L-19 IVS$_\beta$ RNA.

| Substrate | Site | Size (nt)* | Sequence† |
|---|---|---|---|
| pAK-105 | 1 | 148 | UCCUCU ↓ GCCUC (−6 to −1) |
| (β-globin pre-mRNA) | 2 | 464 | AACUCU AAGAG |
| pT7-1 (pBR322) | 1 | 145 | UCCCUU UUUUG |
|  | 2 | 556 | CACUCU CAGUA |
|  | 3 | 603 | UAUUUU CUCCU |
|  | 4 | 805 | UCCUCU AGAGU |
| Consensus observed |  |  | U$^C_A$CUCU ↓ N |
| expected‡ |  |  | C$^C_U$CUCU ↓ N |

*Size of the GTP-labeled fragment.
†Sequences are listed in 5' → 3' direction. Arrows indicate sites of cleavage and guanosine addition.
‡The expected consensus sequence is based on the known sequence at the end of the 5' exon (CUCUCU) modified by the possibility that either a C or a U at position -5 might be able to pair with the G in the active site. At position -1, there is some basis for thinking that a C might not be as good as a U (Davies. R. W., et al. (1982) Nature 300: 710-724; Michel. F.. et al. (1983) EMBO J.2: 33-38; Inoue. T., et al. (1986) J. Mol. Biol. 189: 143-165.

TABLE 2

Relative Activity of Different Acceptors in the Transphosphorylation Reaction$^a$

| acceptor | activity | acceptor | activity |
|---|---|---|---|
| UPT | − | UUU | − |
| CTP | − | UCU | ++ |
| UC | − | CCU | +/− |
| CC | − | AU$_3$ | − |
| AA | − | GU$_3$ | − |
| GU | − | C$_4$U | ++ |
| UU | − | C$_5$ | ++ |
| CU | − | U$_6$ | +/− |
| AUU | − | dC$_5$ | − |

$^a$E-p* was incubated with 10 μM oligonucleotide (or mono- or di- nucleotide) in 20 mM MgCl$_2$ and 50 mM Tris-HCl, pH 7.5, at 42° C. for 30 min. Transfer of the phosphate to the oligonucleotide was assayed by sequencing gel electrophoresis and autoradiography. ++, approximately the same activity as C$_5$; +/−, barely detectable activity, estimated as ~1% that of C$_5$; −, no activity detectable under these conditions.

TABLE 3
Kinetic Parameters for Cleavage of Oligonucleotide Substrates by L-21 ScaI RNA[a]

| substrate | mismatch −5 | mismatch −3 | $k_{cat}$ (min⁻¹) | $K_m$ (μM) | $k_{cat}/K_m$ (min⁻¹ μM⁻¹) | ΔG° (kcal/mol)[b] |
|---|---|---|---|---|---|---|
| GGCCCCU↓AAAAA (−5−3) | | C·A | 3.7 | 0.14 | 26 | −6.7 |
| GGCCCACUAAAAA | | A·A | 1.7 | 0.3 | 6 | −6.7 |
| GGCCCGCUAAAAA | | G·A | 1.0 | 0.3 | 3 | −6.7 |
| GGCCCUCUAAAAA | | | 0.04 ± 0.01 | 0.16 ± 0.06 | 0.3 | −10.9 |
| GGCUCCCUAAAAA | U·G | C·A | 7.2 | 6.3 | 1 | −3.6 |
| GGCUCACUAAAAA | U·G | A·A | 1.0 | 3.9 | 0.3 | −3.6 |
| GGCUCGCUAAAAA | U·G | G·A | 0.7 | 1.7 | 0.4 | −3.6 |
| GGCUCUCUAAAAA | U·G | | 0.15 | 0.13 | 1 | −7.8 |

[a]Substrates were incubated with 0.01 μM L-21 ScaI RNA under standard reaction conditions at 50° C. in the absence of urea (see Materials and Methods). For GGCCCUCUA₅ substrate, three complete kinetic analyses were performed with substrate concentrations spanning the range 0.10–4.0 μM. Listed is the mean ± SD of $k_{cat}$ and $K_m$ from the three Lineweaver-Burk plots. In all other cases, $k_{cat}$ and $K_m$ were estimated from rate measurements done at 0.10 and 1.0 μM substrate. While the hierarchy of $k_{cat}$ and $K_m$ values was reproducible between experiments, the actual values varied by as much as 2-fold.
[b]Estimated free energy change for formation of the substrate-ribozyme complex at 50° C., based on thermodynamic parameters derived from studies of oligoribonucleotides (Freier et al., 1986) and corrected to 50° C. using values of ΔH° and ΔS° obtained from D. Turner (personal communication). These parameters assume that all mismatches are equally destabilizing. thermodynamic measurements of the effect of mismatches in DNA indicate that a C·A mismatch is less stable than an A·A or G·A mismatch (Aboul-ela et al., 1985).

TABLE 4
Urea Affects Cleavage of GGCCCGUA₅ Primarily by Changing $k_{cat}$[a]

| [urea] (M) | $K_m$ (μM) | $V_{max}$ (μM min⁻¹) | $k_{cat}$ (min⁻¹) | $k_{cat}/K_m$ (μM⁻¹ min⁻¹) |
|---|---|---|---|---|
| 0 | 0.89 | 0.020 | 2.0 | 2.2 |
| 1.0 | 0.83 | 0.025 | 2.5 | 3.0 |
| 1.5 | 0.50 | 0.016 | 1.6 | 3.2 |
| 2.0 | 0.74 | 0.009 | 0.9 | 1.2 |
| 2.5 | 0.70 | 0.004 | 0.4 | 0.6 |

[a]Data from FIG. 5. Temperature was 50° C.

TABLE 5

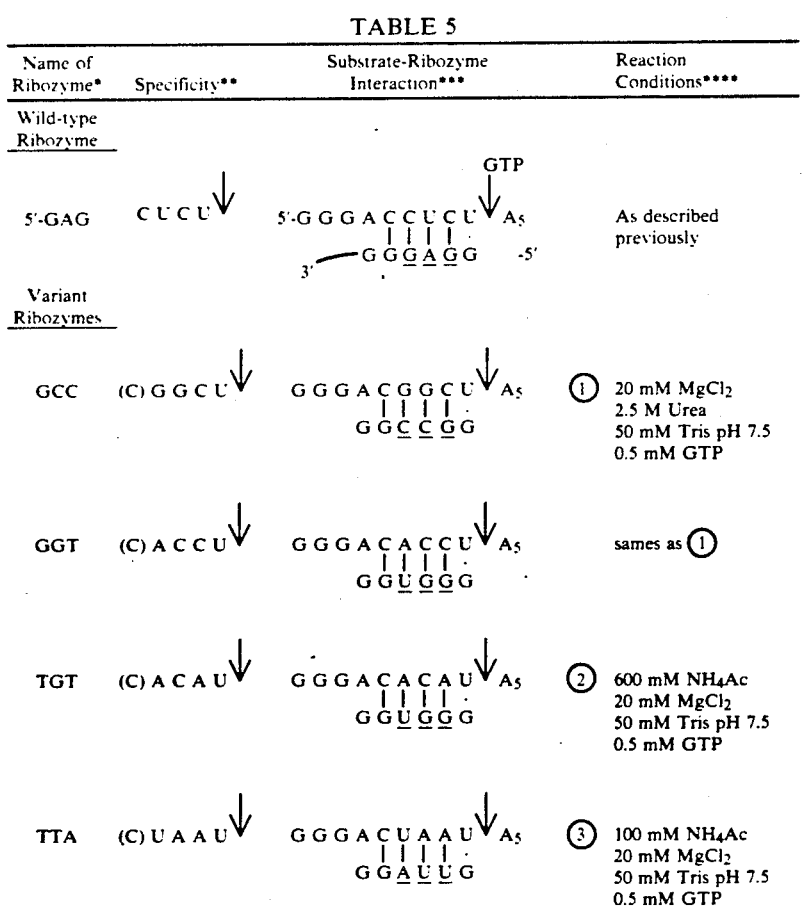

| Name of Ribozyme* | Specificity | Substrate-Ribozyme Interaction* | Reaction Conditions**** |
|---|---|---|---|
| Wild-type Ribozyme | | | |
| 5'-GAG | CUCU↓ | 5'-GGGACCUCU↓A₅ <br> ‖‖‖‖ <br> 3'—GGGAGG-5' (GTP) | As described previously |
| Variant Ribozymes | | | |
| GCC | (C)GGCU↓ | GGGACGGCU↓A₅ <br> ‖‖‖‖ <br> GGCCGG | ① 20 mM MgCl₂ <br> 2.5 M Urea <br> 50 mM Tris pH 7.5 <br> 0.5 mM GTP |
| GGT | (C)ACCU↓ | GGGACACCU↓A₅ <br> ‖‖‖‖ <br> GGUGGG | same as ① |
| TGT | (C)ACAU↓ | GGGACACAU↓A₅ <br> ‖‖‖‖ <br> GGUGGG | ② 600 mM NH₄Ac <br> 20 mM MgCl₂ <br> 50 mM Tris pH 7.5 <br> 0.5 mM GTP |
| TTA | (C)UAAU↓ | GGGACUAAU↓A₅ <br> ‖‖‖‖ <br> GGAUUG | ③ 100 mM NH₄Ac <br> 20 mM MgCl₂ <br> 50 mM Tris pH 7.5 <br> 0.5 mM GTP |

TABLE 5-continued

| Name of Ribozyme* | Specificity** | Substrate-Ribozyme Interaction*** | Reaction Conditions**** |
|---|---|---|---|
| TTC | (C) G A A U ↓ | G G G A C G A A U ↓ A₅<br>         \| \| \| \|<br>        G G C U U G | same as ② |
| AAT | (C) A U U U ↓ | G G G A C A U U U ↓ A₅<br>         \| \| \| \|<br>        G G U A A G | 20 mM MgCl₂<br>50 mM Tris pH 7.5<br>0.5 mM GTP<br>or same as ③ |

*Ribozymes are named according to the active site sequence (2nd, 3rd and 4th positions) as determined by sequence analysis of the plasmid DNA encoding the ribozyme. The first position is always G, so is not included in the name.
**The arrow represents site of GTP addition. The (C) represents a nucleotide whose contribution to cleavage has not been assessed.
***In each diagram, the top strand is the oligoribonucleotide test substrate. The bottom strand represents the portion of the ribozyme sequence which forms part of the active site and determines substrate specificity. The underlined nucleotides are the positions upon which the name of the ribozyme was based. (Note that 5' → 3' is right-to-left on the bottom strand, whereas it is written left-to-right in column 1. Also, a T in DNA becomes a U in RNA.)
****NH4Ac is NH₄C₂H₃O₂

What is claimed:

1. A method for preventing non-complementary cleavage by an enzymatic RNA molecule of a separate RNA molecule, comprising the steps of:
   providing an enzymatic RNA molecule having an RNA substrate-binding site comprising a first nucleotide sequence and an endonuclease activity independent of any protein in vitro, said endonuclease activity being active at or at a location proximal to a second nucleotide sequence in the separate RNA molecule complementary to said first nucleotide sequence, and
   contacting said enzymatic RNA molecule and the separate RNA molecule in the presence of a denaturing agent to allow said endonuclease activity to cause specific cleavage of said separate RNA molecule at or proximal to said second nucleotide sequence but not at any other nucleotide sequence which is not complementary to said first nucleotide sequence.

2. The method of claim 1, wherein said denaturing agent is chosen from urea and formamide.

3. The method of claim 2, wherein said denaturing agent is provided at a concentration between 1.5 and 3.0 Molar.

4. The method of claim 1, wherein said first and second nucleotide sequences comprise between 4 and 6 nucleotides.

5. A method for cleaving a cleavage site in a separate RNA molecule, comprising the steps of:
   providing an enzymatic RNA molecule comprising an RNA substrate-binding site formed from at least four nucleotides, said enzymatic RNA molecule having an endonuclease activity independent of any protein in vitro, said endonuclease activity being active at or at a site proximal to a nucleotide sequence complementary to said at least four nucleotides at the RNA substrate-binding site of said enzymatic molecule,
   providing the separate RNA molecule, wherein said cleavage site in the separate RNA molecule is complementary to said at least four nucleotides at at least two of said four nucleotides; and
   contacting said enzymatic RNA molecule and the separate RNA molecule to allow said endonuclease activity to cleave said separate RNA molecule at or proximal to said cleavage site.

6. The method of claim 5, wherein said separate RNA molecule and said enzymatic RNA molecule are contacted together in the presence of less than 1 Molar denaturant.

7. The method of claim 5 or 6, wherein said separate RNA molecule and said enzymatic RNA molecule are contacted together in the presence of less than 5 millimolar magnesium ion.

8. A method for cleaving a cleavage site in a separate RNA molecule, comprising the steps of:
   providing an enzymatic RNA molecule comprising an RNA substrate-binding site formed from at least five nucleotides, said enzymatic RNA molecule having an endonuclease activity independent of any protein in vitro, said endonuclease activity being active at or at a site proximal to a nucleotide sequence complementary to said at least five nucleotides at the RNA substrate-binding site of said enzymatic molecule,
   providing the separate RNA molecule, wherein said cleavage site in the separate RNA molecule is complementary to said at least five nucleotides at at least two of said five nucleotides; and
   contacting said enzymatic RNA molecule and the separate RNA molecule to allow said endonuclease activity to cleave said separate RNA molecule at or proximal to said cleavage site.

9. A method for cleaving a cleavage site in a separate RNA molecule, comprising the steps of:
   providing an enzymatic RNA molecule comprising an RNA substrate-binding site formed from at least six nucleotides, said enzymatic RNA molecule having an endonuclease activity independent of any protein in vitro, said endonuclease activity being active at or at a site proximal to a nucleotide sequence complementary to said at least six nucleotides at the RNA substrate-binding site of said enzymatic molecule,
   providing the separate RNA molecule, wherein said cleavage site in the separate RNA molecule is complementary to said at least six nucleotides at at least two of said six nucleotides; and
   contacting said enzymatic RNA molecule and the separate RNA molecule to allow said endonuclease activity to cleave said separate RNA molecule at or proximal to said cleavage site.

10. The method of claim 5, 8, or 9, wherein said separate RNA molecule is complementary at at least three of said nucleotides of said RNA substrate-binding site.

11. The method of claim 5, 8, or 9, wherein said separate RNA molecule is complementary at at least four of said nucleotides of said RNA substrate-binding site.

12. The method of claim 8 or 9, wherein said separate RNA molecule is complementary at at least five of said nucleotides of said RNA substrate-binding site.

13. The method of claim 1, wherein said separate RNA molecule is complementary at at least six of said nucleotides of said RNA substrate-binding site.

14. The method of claim 5, 8 or 9 wherein said cleavage site of said separate RNA molecule is completely complementary to said RNA substrate-binding site.

15. The method of claim 5, 8, or 9 wherein said complementary nucleotides are chosen from the base pair combinations A:T, A:U, G:C, and G:U.

16. The method of claim 11 wherein said complementary nucleotides are chosen form the base pair combinations A:T, A:U, G:C, and G:U.

17. The method of claim 12 wherein said complementary nucleotides are chosen from the base pair combinations A:T, A:U, G:C, and G:U.

18. The method of claim 13 wherein said complementary nucleotides are chosen from the base pair combinations A:T, A:U, G:C, and G:U.

19. A DNA vector comprising DNA encoding L-21 ScaI enzymatic RNA, said DNA being constructed and arranged to cause production of the L-21 ScaI enzymatic RNA molecule when contacted with ScaI restriction endonuclease and an RNA polymerase under transcriptional conditions.

20. The vector of claim 19, wherein said DNA comprises a T7 promoter arranged to interact with said RNA polymerase to cause transcription of said L-21 ScaI enzymatic RNA molecule.

21. The vector of claim 20, wherein said DNA is PT7 L-21.

22. The vector of claim 21, wherein said PT7 L-21 is that DNA present as a deposit designated ATCC 40291.

* * * * *

UNITED STATES PATENT AND TRADEMARK OFFICE
CERTIFICATE OF CORRECTION

PATENT NO. : 5,116,742

DATED : May 26, 1992

INVENTOR(S) : CECH, T. et al.

It is certified that error appears in the above-indentified patent and that said Letters Patent is hereby corrected as shown below:

Title page, References: Col. 2, add the following:

"Designer Enzymes for Genetic Engineers, "New Scientist, 1987, vol. [114] 113, No. 1545, p. 35.

[Carriga] Garriga et al.

Precursor of Tetrahymena and the Mechanism of Self-Splicing, "J. Mol. Biol., (1986) 189, p. 143-165.

Perea and Jacq....I[N]ntron of the Yeast.....

Page 3, References:

RNA Restriction Endo[c]nuclease......

Gerda van der Horst...[r]Ribosomal....pp. 759-766, 1985. [4n 3070]

Sharmeen et al.,...pp. 2674-2679, 1988.

Rawn, ...pp. 793-[1]799, 1989.

A. D. M. van Mansfeld....1980. [4n 3085]

Column 8, line 10: pBGST7

UNITED STATES PATENT AND TRADEMARK OFFICE
CERTIFICATE OF CORRECTION

PATENT NO. : 5,116,742
DATED : MAY 26, 1992
INVENTOR(S) : CECH, T. et al.

It is certified that error appears in the above-identified patent and that said Letters Patent is hereby corrected as shown below:

Column 8, Line 39: $Mg^{2+}$

Column 9, Line 51: [min-] $min^-$

Column 10, Line 27: [sec-] $sec^-$

Column 10, Line 68: [pK$_1$=] $pK_a=$

Column 11, Line 33: [1010] $10^{10}$

Column 13, Line 12: [H20] $H_2O$

Column 30, Line 42 [±or] for

Column 31, Line 22: Such destabilization would

Column 32, Line 43: [CCCL] CCCU

Column 34, Line 44: [o±] of

Column 34, Line 49: [o±] of

Column 35, Line 51: the $G^{414}.-A^{16}$

Column 35, Line 65: [ma3or] major

UNITED STATES PATENT AND TRADEMARK OFFICE
CERTIFICATE OF CORRECTION

PATENT NO. : 5,116,742
DATED : May 26, 1992
INVENTOR(S) : Thomas R. Cech, et al.

It is certified that error appears in the above-indentified patent and that said Letters Patent is hereby corrected as shown below:

Column 41, line 68: [ɫɔr]  for

Signed and Sealed this

Ninth Day of August, 1994

Attest:

BRUCE LEHMAN

*Attesting Officer*      *Commissioner of Patents and Trademarks*